(12) United States Patent  
Zergiebel

(10) Patent No.: US 9,987,010 B2
(45) Date of Patent: *Jun. 5, 2018

(54) MULTIPLE MEMBER INTERCONNECT FOR SURGICAL INSTRUMENT AND ABSORBABLE SCREW FASTENER

(71) Applicant: Covidien LP, Mansfield, MA (US)

(72) Inventor: Earl M. Zergiebel, Guilford, CT (US)

(73) Assignee: Covidien LP, Mansfield, MA (US)

( * ) Notice: Subject to any disclaimer, the term of this patent is extended or adjusted under 35 U.S.C. 154(b) by 714 days.

This patent is subject to a terminal disclaimer.

(21) Appl. No.: 14/578,936

(22) Filed: Dec. 22, 2014

(65) Prior Publication Data

US 2015/0150558 A1 Jun. 4, 2015

Related U.S. Application Data

(63) Continuation of application No. 11/801,525, filed on May 10, 2007, now Pat. No. 8,926,637, which is a (Continued)

(51) Int. Cl.
| | |
|---|---|
| *A61B 17/10* | (2006.01) |
| *A61B 17/068* | (2006.01) |
| *A61B 17/064* | (2006.01) |
| *A61B 17/29* | (2006.01) |
| *A61B 90/00* | (2016.01) |

(52) U.S. Cl.
CPC .......... *A61B 17/105* (2013.01); *A61B 17/068* (2013.01); *A61B 2017/0648* (2013.01); *A61B 2017/2923* (2013.01); *A61B 2090/0814* (2016.02)

(58) Field of Classification Search
CPC ..... A61L 31/06; A61B 17/861; A61B 17/864; A61B 17/866; B25B 17/00
See application file for complete search history.

(56) References Cited

U.S. PATENT DOCUMENTS

| 2,033,039 A | 3/1936 | Limpert |
| 2,230,349 A | 2/1941 | Eaton et al. |
| (Continued) | | |

FOREIGN PATENT DOCUMENTS

| DE | 10300787 A1 | 9/2004 |
| DE | 10 2010 015009 A1 | 10/2011 |
| (Continued) | | |

OTHER PUBLICATIONS

Extended European Search Report corresponding to counterpart application EP 14 19 7885.8 dated Apr. 30, 2015; 9pp.

(Continued)

*Primary Examiner* — Gregory Anderson
*Assistant Examiner* — Christina Lauer

(57) ABSTRACT

A absorbable surgical screw fastener is provided which includes a head and a tapered shaft extending distally of the head. Buttress threads are provided about the tapered shaft to secure the fastener in tissue. The fastener includes slots formed in the head and buttress threads. A gap is provided between the buttress threads in the head to secure a prosthetic. There is also provided a surgical instrument having novel lockout structure to prevent inadvertent actuation.

20 Claims, 63 Drawing Sheets

Related U.S. Application Data continuation-in-part of application No. 10/560,879, filed as application No. PCT/US2004/018702 on Jun. 14, 2004, now Pat. No. 7,670,362.

(60) Provisional application No. 60/478,352, filed on Jun. 13, 2003.

(56) References Cited

U.S. PATENT DOCUMENTS

| | | |
|---|---|---|
| 3,596,528 A | 8/1971 | Dittrich et al. |
| 3,874,041 A | 4/1975 | Smith |
| 3,882,756 A | 5/1975 | Sauer et al. |
| 4,013,071 A | 3/1977 | Rosenberg |
| 4,175,555 A | 11/1979 | Herbert |
| 4,252,071 A | 2/1981 | Rathert et al. |
| 4,285,292 A | 8/1981 | Rathert et al. |
| 4,350,491 A | 9/1982 | Steuer |
| 4,432,358 A | 2/1984 | Fixel |
| 4,537,185 A | 8/1985 | Stednitz |
| 4,644,957 A | 2/1987 | Ricciardelli et al. |
| 4,658,825 A | 4/1987 | Hochberg et al. |
| 4,756,653 A | 7/1988 | Berger |
| 4,762,453 A | 8/1988 | DeCaro |
| 4,815,909 A | 3/1989 | Simons |
| 4,873,976 A | 10/1989 | Schreiber |
| 4,884,572 A | 12/1989 | Bays et al. |
| 4,895,148 A | 1/1990 | Bays et al. |
| 4,976,715 A | 12/1990 | Bays et al. |
| 4,994,073 A | 2/1991 | Green |
| 5,053,047 A | 10/1991 | Yoon |
| 5,129,906 A | 7/1992 | Ross et al. |
| 5,203,784 A | 4/1993 | Ross et al. |
| 5,203,787 A | 4/1993 | Noblitt et al. |
| 5,203,864 A | 4/1993 | Phillips |
| 5,217,486 A | 6/1993 | Rice et al. |
| 5,236,563 A | 8/1993 | Loh |
| 5,246,441 A | 9/1993 | Ross et al. |
| 5,258,000 A | 11/1993 | Gianturco |
| 5,258,010 A | 11/1993 | Green et al. |
| 5,263,974 A | 11/1993 | Matsutani et al. |
| 5,290,296 A | 3/1994 | Phillips |
| 5,290,297 A | 3/1994 | Phillips |
| 5,312,023 A | 5/1994 | Green et al. |
| 5,342,397 A | 8/1994 | Guido |
| 5,376,097 A | 12/1994 | Phillips |
| 5,381,943 A | 1/1995 | Allen et al. |
| 5,382,260 A | 1/1995 | Dormandy, Jr. et al. |
| 5,429,641 A | 7/1995 | Gotfried |
| 5,464,144 A | 11/1995 | Guy et al. |
| 5,464,421 A | 11/1995 | Wortrich |
| D366,113 S | 1/1996 | Morgan |
| 5,582,616 A | 12/1996 | Bolduc et al. |
| 5,593,423 A | 1/1997 | Person et al. |
| 5,645,565 A | 7/1997 | Rudd et al. |
| 5,690,676 A | 11/1997 | DiPoto et al. |
| 5,695,497 A | 12/1997 | Stahelin |
| 5,728,116 A | 3/1998 | Rosenman |
| 5,730,744 A | 3/1998 | Justin et al. |
| 5,782,844 A | 7/1998 | Yoon et al. |
| 5,827,291 A | 10/1998 | Fucci et al. |
| 5,830,221 A | 11/1998 | Stein et al. |
| 5,895,396 A | 4/1999 | Day et al. |
| 5,904,685 A | 5/1999 | Walawalkar |
| 5,904,696 A | 5/1999 | Rosenman |
| 5,921,997 A | 7/1999 | Fogelberg et al. |
| 5,961,524 A | 10/1999 | Crombie |
| 5,964,783 A | 10/1999 | Grafton et al. |
| 5,997,552 A * | 12/1999 | Person ............... A61B 17/064 606/139 |
| 6,027,523 A | 2/2000 | Schmieding |
| 6,030,162 A | 2/2000 | Huebner |
| 6,036,701 A | 3/2000 | Rosenman |
| 6,063,112 A | 5/2000 | Sgro |
| 6,066,777 A | 5/2000 | Benchetrit |
| 6,096,060 A | 8/2000 | Fitts et al. |
| 6,146,387 A | 11/2000 | Trott et al. |
| 6,168,598 B1 | 1/2001 | Martello |
| 6,171,330 B1 | 1/2001 | Benchetrit |
| 6,214,031 B1 | 4/2001 | Schmieding et al. |
| 6,221,023 B1 | 4/2001 | Matsuba et al. |
| 6,264,702 B1 | 7/2001 | Ory et al. |
| 6,269,716 B1 | 8/2001 | Amis |
| 6,283,973 B1 | 9/2001 | Hubbard et al. |
| 6,290,702 B1 | 9/2001 | Fucci et al. |
| 6,296,656 B1 | 10/2001 | Bolduc et al. |
| 6,319,270 B1 | 11/2001 | Grafton et al. |
| 6,328,746 B1 | 12/2001 | Gambale |
| 6,343,531 B2 | 2/2002 | Amis |
| 6,391,060 B1 | 5/2002 | Ory et al. |
| 6,406,423 B1 | 6/2002 | Scetbon |
| 6,408,656 B1 | 6/2002 | Ory et al. |
| 6,425,900 B1 | 7/2002 | Knodel et al. |
| 6,443,964 B1 | 9/2002 | Ory et al. |
| 6,447,524 B1 | 9/2002 | Knodel et al. |
| 6,451,032 B1 | 9/2002 | Ory et al. |
| 6,464,706 B1 | 10/2002 | Winters |
| 6,477,923 B2 | 11/2002 | Amis |
| 6,478,727 B2 | 11/2002 | Scetbon |
| 6,488,681 B2 | 12/2002 | Martin et al. |
| 6,503,251 B1 | 1/2003 | Shadduck |
| 6,508,820 B2 | 1/2003 | Bales |
| 6,547,801 B1 | 4/2003 | Dargent et al. |
| 6,551,333 B2 | 4/2003 | Kuhns et al. |
| 6,554,830 B1 | 4/2003 | Chappius |
| 6,554,852 B1 | 4/2003 | Oberlander |
| 6,565,572 B2 | 5/2003 | Chappius |
| 6,565,580 B1 | 5/2003 | Beretta |
| 6,569,188 B2 | 5/2003 | Grafton et al. |
| 6,572,626 B1 | 6/2003 | Knodel et al. |
| 6,575,897 B1 | 6/2003 | Ory et al. |
| 6,575,976 B2 | 6/2003 | Grafton |
| 6,592,593 B1 | 7/2003 | Parodi et al. |
| 6,596,002 B2 | 7/2003 | Therin et al. |
| 6,629,977 B1 | 10/2003 | Wolf |
| 6,635,059 B2 | 10/2003 | Randall et al. |
| 6,648,892 B2 | 11/2003 | Martello |
| 6,666,854 B1 | 12/2003 | Lange |
| 6,669,073 B2 | 12/2003 | Milliman et al. |
| 6,685,629 B2 | 2/2004 | Therin |
| 6,692,506 B1 | 2/2004 | Ory et al. |
| 6,695,855 B1 | 2/2004 | Gaston |
| 6,743,233 B1 | 6/2004 | Baldwin et al. |
| 6,800,081 B2 | 10/2004 | Parodi |
| 6,811,552 B2 | 11/2004 | Weil, Sr. et al. |
| 6,830,573 B2 | 12/2004 | Strong et al. |
| 6,929,661 B2 | 8/2005 | Bolduc et al. |
| 6,953,139 B2 | 10/2005 | Milliman et al. |
| 6,953,463 B2 | 10/2005 | West, Jr. |
| 6,960,217 B2 | 11/2005 | Bolduc |
| 7,001,389 B1 | 2/2006 | Navarro et al. |
| 7,128,754 B2 | 10/2006 | Bolduc |
| 7,135,025 B2 | 11/2006 | Pohjonen et al. |
| 7,147,657 B2 | 12/2006 | Chiang et al. |
| 7,491,232 B2 | 2/2009 | Bolduc et al. |
| 7,544,198 B2 | 6/2009 | Parodi |
| 7,591,842 B2 | 9/2009 | Parodi |
| 7,637,932 B2 | 12/2009 | Bolduc et al. |
| 7,823,267 B2 | 11/2010 | Bolduc |
| 7,828,838 B2 | 11/2010 | Bolduc et al. |
| 7,905,890 B2 | 3/2011 | Whitfield et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,075,570 B2 | 12/2011 | Bolduc et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,292,933 B2 | 10/2012 | Zergiebel |
| 8,323,314 B2 | 12/2012 | Blier |
| 8,328,823 B2 | 12/2012 | Aranyi et al. |
| 8,343,184 B2 | 1/2013 | Blier |
| 8,414,627 B2 | 4/2013 | Corradi et al. |

(56) References Cited

U.S. PATENT DOCUMENTS

| | | |
|---|---|---|
| 8,465,520 B2 | 6/2013 | Blier |
| 8,597,311 B2 | 12/2013 | Criscuolo et al. |
| 8,685,044 B2 | 4/2014 | Bolduc et al. |
| 8,690,897 B2 | 4/2014 | Bolduc |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,920,439 B2 | 12/2014 | Cardinale et al. |
| 8,926,637 B2 * | 1/2015 | Zergiebel ............ A61B 17/068 606/104 |
| 8,968,311 B2 | 3/2015 | Allen, IV et al. |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,274 B2 | 6/2016 | Zergiebel |
| 9,402,623 B2 | 8/2016 | Kayan |
| 9,486,218 B2 | 11/2016 | Criscuolo et al. |
| 9,526,498 B2 | 12/2016 | Reed |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 2001/0007074 A1 | 7/2001 | Strobel et al. |
| 2002/0013590 A1 | 1/2002 | Therin et al. |
| 2002/0111641 A1 | 8/2002 | Peterson et al. |
| 2003/0004395 A1 | 1/2003 | Therin |
| 2003/0009441 A1 | 1/2003 | Holsten et al. |
| 2003/0036676 A1 | 2/2003 | Scetbon |
| 2003/0114839 A1 | 6/2003 | Looper et al. |
| 2003/0158555 A1 | 8/2003 | Sanders et al. |
| 2003/0187465 A1 | 10/2003 | Bailly et al. |
| 2004/0068275 A1 | 4/2004 | Ramshaw et al. |
| 2004/0111089 A1 | 6/2004 | Stevens et al. |
| 2004/0127916 A1 | 7/2004 | Bolduc et al. |
| 2004/0153124 A1 | 8/2004 | Whitman |
| 2004/0181222 A1 | 9/2004 | Culbert et al. |
| 2004/0193217 A1 | 9/2004 | Lubbers et al. |
| 2004/0243139 A1 | 12/2004 | Lewis et al. |
| 2005/0267478 A1 | 12/2005 | Corradi et al. |
| 2006/0100629 A1 | 5/2006 | Lee |
| 2007/0088390 A1 | 4/2007 | Paz et al. |
| 2008/0147113 A1 | 6/2008 | Nobis et al. |
| 2008/0188868 A1 | 8/2008 | Weitzner et al. |
| 2008/0243106 A1 | 10/2008 | Coe et al. |
| 2008/0281336 A1 | 11/2008 | Zergiebel |
| 2008/0312687 A1 | 12/2008 | Blier |
| 2009/0112234 A1 | 4/2009 | Crainich et al. |
| 2009/0188965 A1 | 7/2009 | Levin et al. |
| 2010/0030262 A1 | 2/2010 | McLean et al. |
| 2011/0022065 A1 | 1/2011 | Shipp |
| 2011/0042441 A1 | 2/2011 | Shelton, IV et al. |
| 2011/0060349 A1 | 3/2011 | Cheng et al. |
| 2011/0071578 A1 | 3/2011 | Colesanti et al. |
| 2011/0079627 A1 | 4/2011 | Cardinale et al. |
| 2011/0087240 A1 | 4/2011 | Shipp |
| 2011/0204120 A1 | 8/2011 | Crainich |
| 2011/0295269 A1 | 12/2011 | Swensgard et al. |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2013/0018392 A1 | 1/2013 | Zergiebel |
| 2013/0110088 A1 | 5/2013 | Wenchell |
| 2013/0131700 A1 | 5/2013 | Criscuolo et al. |
| 2013/0197591 A1 | 8/2013 | Corradi et al. |
| 2014/0114329 A1 | 4/2014 | Zergiebel |
| 2014/0121684 A1 | 5/2014 | Criscuolo et al. |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0018847 A1 | 1/2015 | Criscuolo et al. |
| 2015/0032130 A1 | 1/2015 | Russo |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0066971 A1 | 3/2016 | Corradi et al. |
| 2016/0074034 A1 | 3/2016 | Shipp |
| 2016/0135807 A1 | 5/2016 | Zergiebel |
| 2016/0166255 A1 | 6/2016 | Fischvogt |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniffin et al. |
| 2017/0042657 A1 | 2/2017 | Criscuolo et al. |
| 2017/0128068 A1 | 5/2017 | Zhang et al. |
| 2017/0151048 A1 | 6/2017 | Russo |

FOREIGN PATENT DOCUMENTS

| | | |
|---|---|---|
| EP | 0 086 721 A2 | 8/1983 |
| EP | 199037 A2 | 10/1986 |
| EP | 0552050 A2 | 7/1993 |
| EP | 0834280 A1 | 4/1998 |
| EP | 1317904 A1 | 6/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| EP | 2853202 A2 | 4/2015 |
| WO | 9811814 A2 | 3/1998 |
| WO | 00/16701 A1 | 3/2000 |
| WO | 0234140 A2 | 5/2002 |
| WO | 03/020139 A2 | 3/2003 |
| WO | 03034925 A2 | 5/2003 |
| WO | 03103507 A2 | 12/2003 |
| WO | 03/090630 A3 | 4/2004 |
| WO | 2004/112841 A2 | 12/2004 |
| WO | 2005004727 A1 | 1/2005 |
| WO | 2012/064692 A2 | 5/2012 |
| WO | 2013/046115 A1 | 4/2013 |

OTHER PUBLICATIONS

Extended European Search Report corresponding to counterpart application EP 14 18 1900.3 dated Apr. 9, 2015; 7pp.

European Search Report from EP 06 00 8305.2 dated Nov. 20, 2006.

Extended European Search Report from EP 06 01 1501.1 dated Dec. 12, 2006.

European Search Report for corresponding EP 08251652 dated Sep. 2, 2008 (3 pages).

Extended European Search Report corresponding to EP 14 15 9394.7, completed Apr. 16, 2014 and dated Apr. 29, 2014; (8 pp).

Extended European Search Report corresponding to Int'l Application No. EP 14 15 1663.3 dated Jun. 7, 2016.

Extended European Search Report corresponding to counterpart Int'l Appln. No. EP 14 81 7036.8 dated Feb. 2, 2017.

(56) References Cited

OTHER PUBLICATIONS

European Office Action corresponding to counterpart Int'l Appln. No. EP 14 19 7885.8 dated Feb. 7, 2017.
Chinese First Office Action corresponding to counterpart Int'l Appln. No. CN 201410090675 dated Feb. 28, 2017.
Extended European Search Report corresponding to counterpart Int'l Appln. No. EP 16 19 8333.3 dated Mar. 15, 2017.
European Office Action corresponding to counterpart Int'l Appln. No. EP 14 15 1663.3 dated May 10, 2017.
Extended European Search Report corresponding to counterpart Int'l Appln. No. EP 17 15 7259.7 dated May 10, 2017.
Chinese First Office Action corresponding to counterpart Int'l Appln. No. CN 2014103559671 dated Jun. 13, 2017.
Australian Examination Report No. 1 corresponding to counterpart Int'l Appln. No. AU 2014200071 dated Jun. 20, 2017.
Australian Examination Report No. 1 corresponding to counterpart Int'l Appln. No. AU 2014201338 dated Jul. 10, 2017.
Extended European Search Report corresponding to EP 14 15 8946.5, completed Jun. 20, 2014 and dated Jul. 8, 2014; (9 pp).
Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).

\* cited by examiner

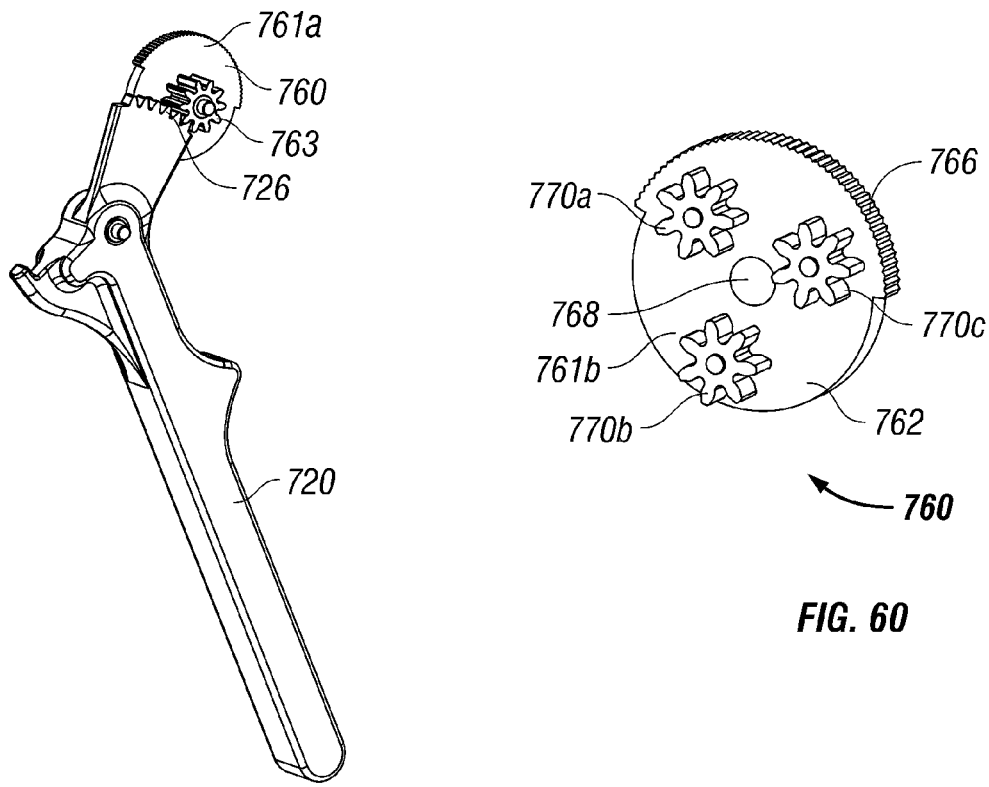
FIG. 59
FIG. 60
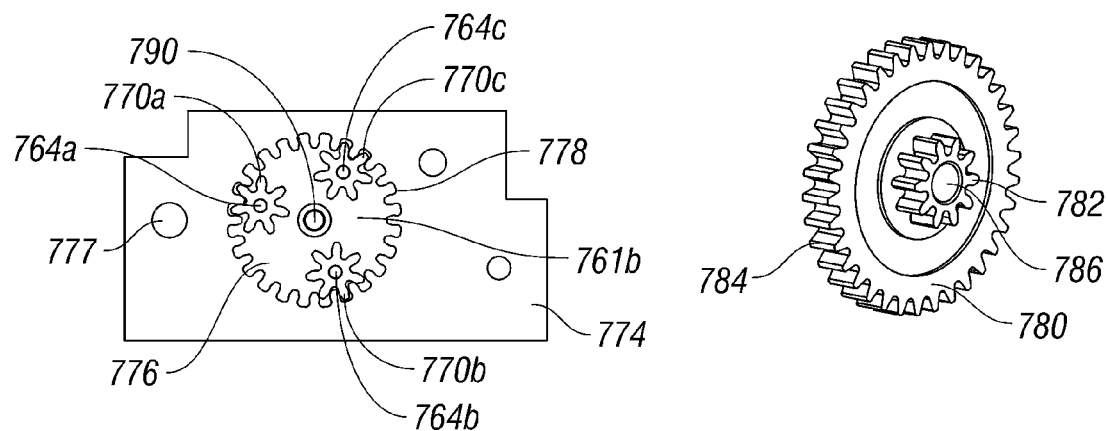
FIG. 60A
FIG. 61

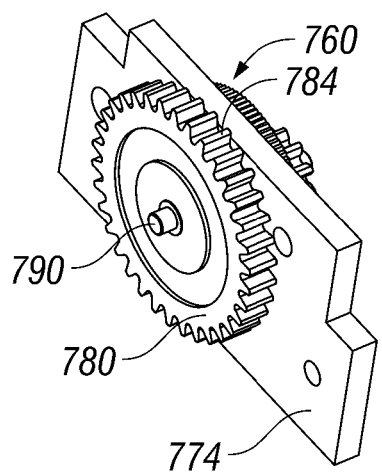 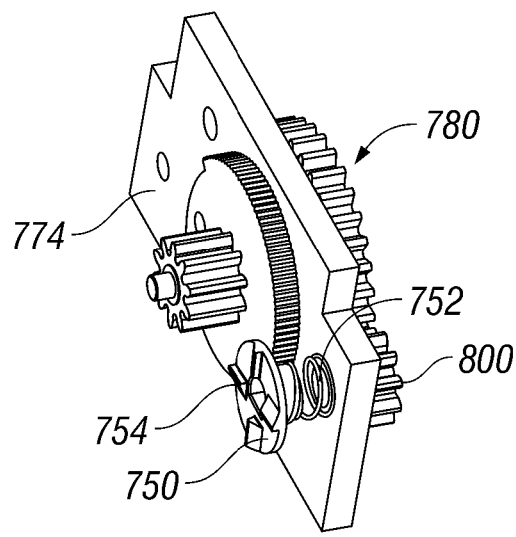
FIG. 62  FIG. 63
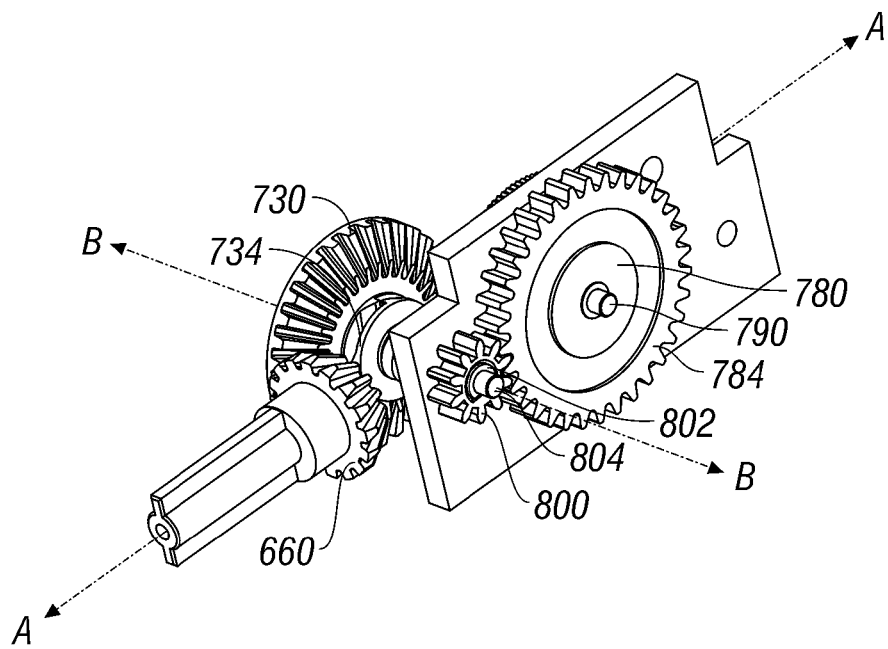
FIG. 64

MULTIPLE MEMBER INTERCONNECT FOR SURGICAL INSTRUMENT AND ABSORBABLE SCREW FASTENER

CROSS-REFERENCE TO RELATED APPLICATIONS

This application is a continuation application claiming the benefit of and priority to U.S. patent application Ser. No. 11/801,525, filed May 10, 2007, now U.S. Pat. No. 8,926,637, which is a continuation-in-part application claiming the benefit of and priority to U.S. patent application Ser. No. 10/560,879, filed May 10, 2006, now U.S. Pat. No. 7,670,362, which is a U.S. National Stage Application of International Patent Application Ser. No. PCT/US2004/018702, filed Jun. 14, 2004, which claims the benefit of and priority to U.S. Provisional Patent Application Ser. No. 60/478,352, filed Jun. 13, 2003, the entire disclosure of each of which is hereby incorporated by reference herein.

BACKGROUND

Technical Field

The present disclosure relates to an absorbable screw fastener and to a multi-fire surgical instrument for inserting the fastener into tissue. More particularly, the present disclosure relates to an absorbable screw fastener and to a multi-fire surgical instrument having a novel interlock system for preventing actuation of the surgical instrument.

Background of Related Art

Various surgical procedures require instruments capable of applying fasteners to tissue to form tissue connections or to secure objects to tissue. For example, during hernia repair procedures it is often desirable to fasten a mesh to body tissue. In certain hernias, such as direct or indirect inguinal hernias, a part of the intestine protrudes through a defect in the support abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

Less invasive surgical procedures are currently available to repair a hernia. In laparoscopic procedures, surgery is performed in the abdomen through a small incision while in endoscopic procedures, surgery is performed through narrow endoscopic tubes or cannulas inserted through small incisions in the body. Laparoscopic and endoscopic procedures generally require long and narrow instruments capable of reaching deep within the body and configured to seal with the incision or tube they are inserted through. Additionally, the instruments are generally capable of being actuated remotely, that is, from outside the body.

Currently, endoscopic techniques for hernia repair utilize fasteners, such as, surgical staples or clips, to secure the mesh to the tissue to provide reinforcement in the repair and structure for encouraging tissue regrowth. The staples or clips are compressed against the tissue and mesh to secure the two together.

One other type of fastener and surgical instrument suited for use in affixing mesh to tissue during procedures such as hernia repair, is a coil fastener having a helically coiled body portion terminating in a tissue penetrating tip. Instruments have been developed to rotate these helically coiled fasteners into tissue. Examples of this type of surgical fasteners and surgical instruments are disclosed in commonly-owned U.S. Pat. No. 5,830,221.

SUMMARY

The presently disclosed surgical screw fastener generally includes a head having a tapered shaft extending distally from the head. A buttressed thread extends along the tapered shaft and terminates in a blunt tip. In one embodiment, a pair of opposed slots are formed in the head. A further pair of opposed slots may also be formed lengthwise through the buttressed threads. The head and tapered shaft define a throughbore for receipt of a mating part of a surgical instrument. The buttressed threads have a flat proximal-facing surface and a conical distal-facing surface. In one embodiment the screw fastener is absorbable. A proximal-most thread of the buttressed thread and a distal-facing surface of the head define a gap for receipt of a prosthetic.

There is also disclosed a surgical instrument having a body and a elongate tubular member extending distally from the body. The elongate tubular member is longitudinally movable with respect to the body. The body contains a gear train and a bevel gear assembly for providing rotational motion to components contained in the elongate tubular member. The surgical instrument includes a lockout member which prevents motion of the gear train and bevel gear assemblies. Movement of the elongate tubular member relative to the body disengages a lockout member and allows motion of the gear train and bevel gear assemblies.

In one embodiment, the surgical instrument includes a driver assembly and a cartridge assembly containing a plurality of fasteners. The driver assembly drives the fasteners out of the elongate tubular member and into target tissue. The surgical instrument includes a socket associated with the driver assembly and the cartridge assembly. A pin provided on the socket is engageable with the lockout mechanism. In one embodiment, the lockout mechanism includes a hook engageable with the pin to prevent movement of the socket.

There is also disclosed a surgical instrument including a handle having a gear assembly and a bevel gear assembly associated with the gear assembly. An elongate tubular member extends distally from the handle. The surgical instrument also includes a link member configured to disengage the gear assembly from the bevel gear assembly. The link member includes a cam which is engageable with a clutch associated with the gear assembly.

In one embodiment, the cartridge assembly includes at least one longitudinally extending beam engageable with a corresponding slot formed in a surgical fastener. A torque member is associated with the driver and is also engageable with a surgical fastener to drive the surgical fastener into tissue.

DESCRIPTION OF THE DRAWINGS

Various embodiments of the presently disclosed absorbable fastener and surgical instrument are disclosed herein with reference to the drawings, wherein:

FIG. 59 is a perspective view the movable handle and planetary gear carrier of the multi-fire surgical instrument of FIGS. 46-59;

FIG. 60 is a perspective view of the planetary gear carrier and planets of the multi-fire surgical instrument of FIGS. 46-60;

FIG. 60a is a front view of the planetary gear carrier and planets of FIG. 60 illustrated on a planetary ring plate;

FIG. 61 is a perspective view of a planetary sun of the multi-fire surgical instrument of FIGS. 46-60a;

FIG. 62 is a perspective view of the planetary sun of FIG. 61 and the planetary ring plate of FIG. 60a;

FIG. 63 is a perspective view of the multi-fire surgical instrument of FIG. 62 further including a clutch and a clutch spring;

FIG. 64 is a perspective view of the multi-fire surgical instrument of FIG. 63 further including the small bevel gear;

DETAILED DESCRIPTION OF EMBODIMENTS

Embodiments of the presently disclosed absorbable screw fastener and multi-fire surgical instrument are described in detail with reference to the drawings wherein like numerals designate identical or corresponding elements in each of the several views. As is common in the art, the term 'proximal" refers to that part or component closer to the user or operator, e.g., surgeon or physician, while the term "distal" refers to that part or component farther away from the user.

Figure 1A:
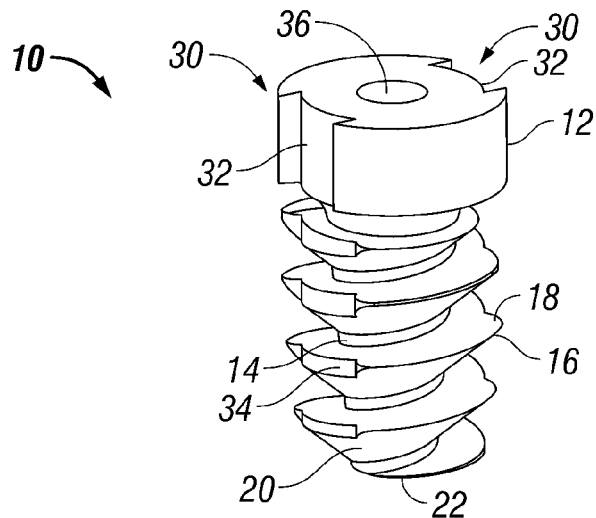
FIG. 1A is a perspective view of an absorbable screw fastener.

FIGS. 1A-1E illustrate an embodiment of the presently disclosed absorbable screw fastener. Referring initially to FIG. 1A, the disclosed absorbable screw fastener 10 generally includes a head 12 having a tapered shaft 14 extending distally from head 12. Head 12 has a generally reduced profile to reduce potential discomfort or irritation when fasteners with high profile heads are used. A series of buttress threads 16 extend along tapered shaft 14. Buttress threads 16 generally have a flat proximal-facing surface 18 and a generally conical distal-facing surface 20. Flat proximal-facing surface 18 provides a greater surface area to prevent against pullout of fastener 10, while conical distal-facing surface 20 facilitate ease of insertion into tissue. Buttress threads 16 terminate in a generally blunt distal end 22 which also facilitates insertion into tissue. In one embodiment, buttress threads 16 have a pitch of about 0.045 threads per inch so as to provide sufficient threads in the fastener to prevent pullout from tissue. One type of fastener is disclosed in various embodiments of commonly-owned U.S. patent application Ser. No. 11/113,879.

Figure 1B:
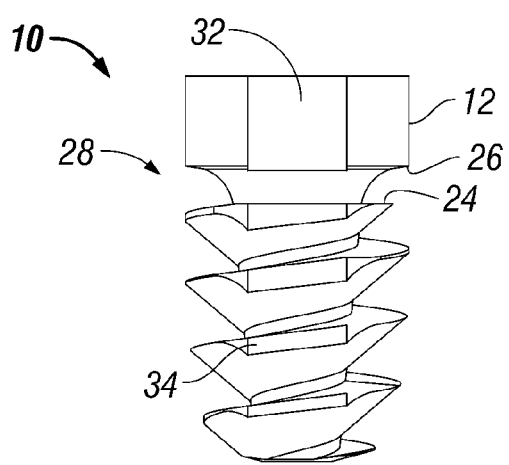
FIG. 1B is a side view of the absorbable screw fastener.
Figure 1C:
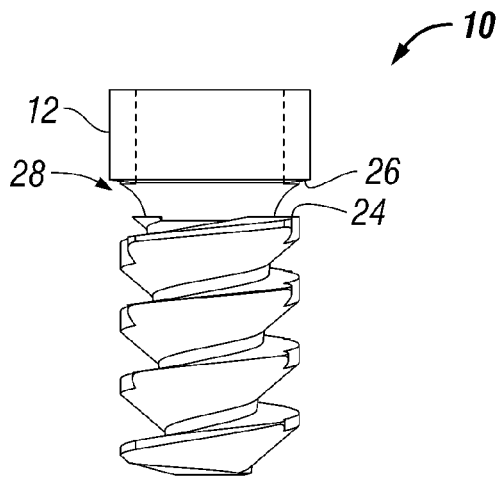
FIG. 1C is a front view of the absorbable screw fastener.

Referring now to FIGS. 1B and 1C, a proximal end of buttress threads 16 has a flat surface 24 which is spaced apart from a distal face 26 of head 12 to define a gap 28 therebetween. Gap 28 is designed to provide a space for a prosthetic, such as, for example, a surgical mesh, applied to tissue.

Figure 1D:
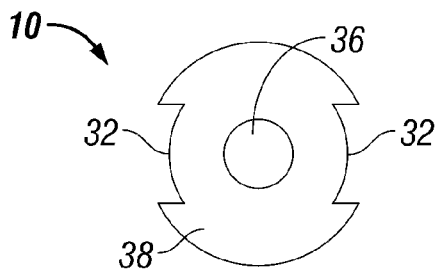
FIG. 1D is a top view of the absorbable screw fastener.
Figure 1E:
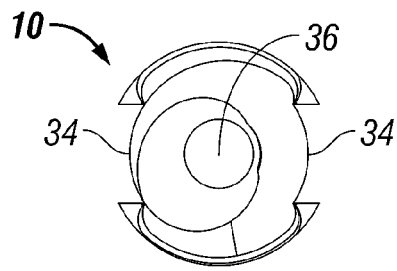
FIG. 1E is a bottom view of the absorbable screw fastener.
Figure 2:
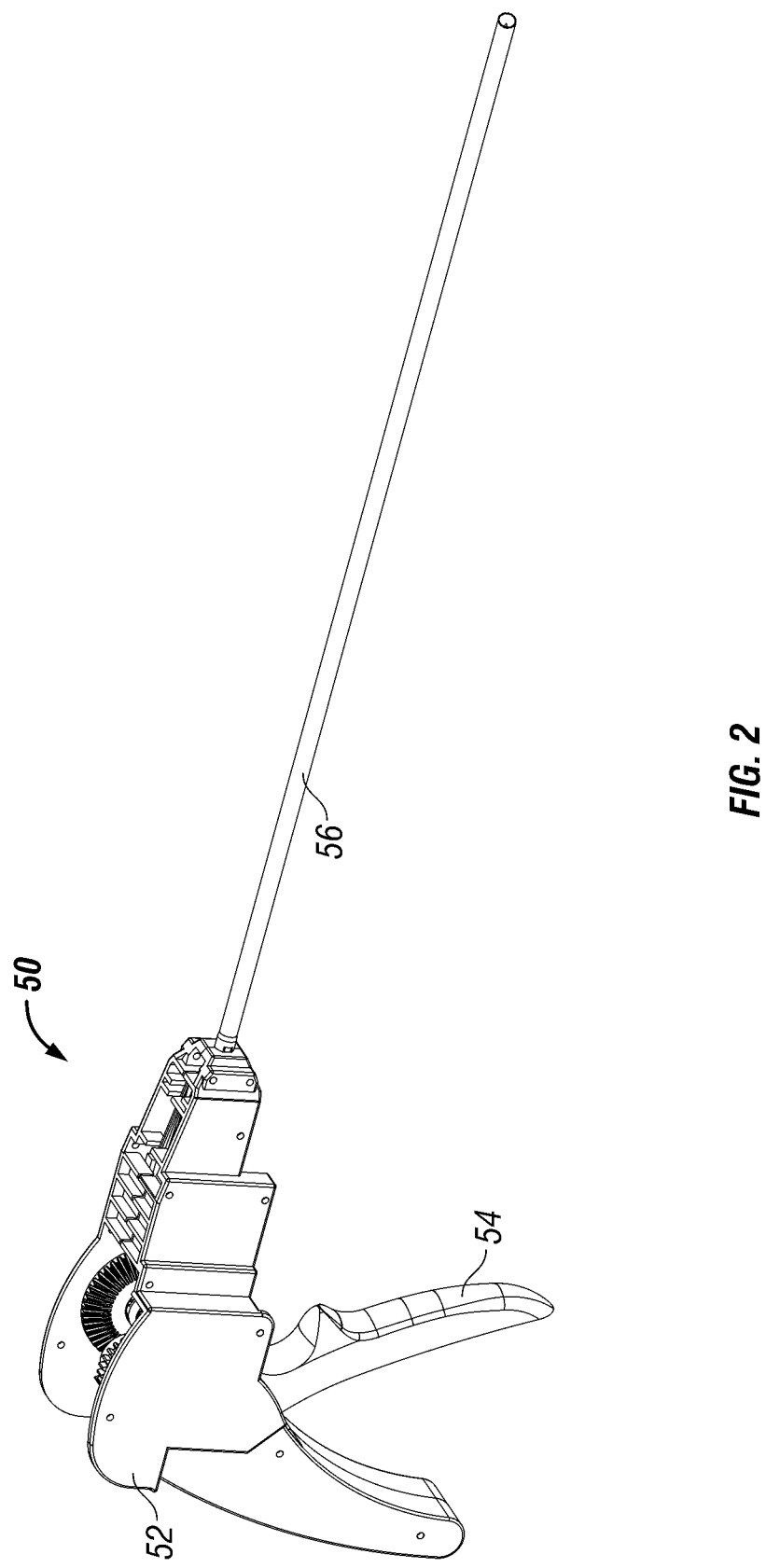
FIG. 2 is a perspective view of one embodiment of a multi-fire surgical instrument.
Figure 3:
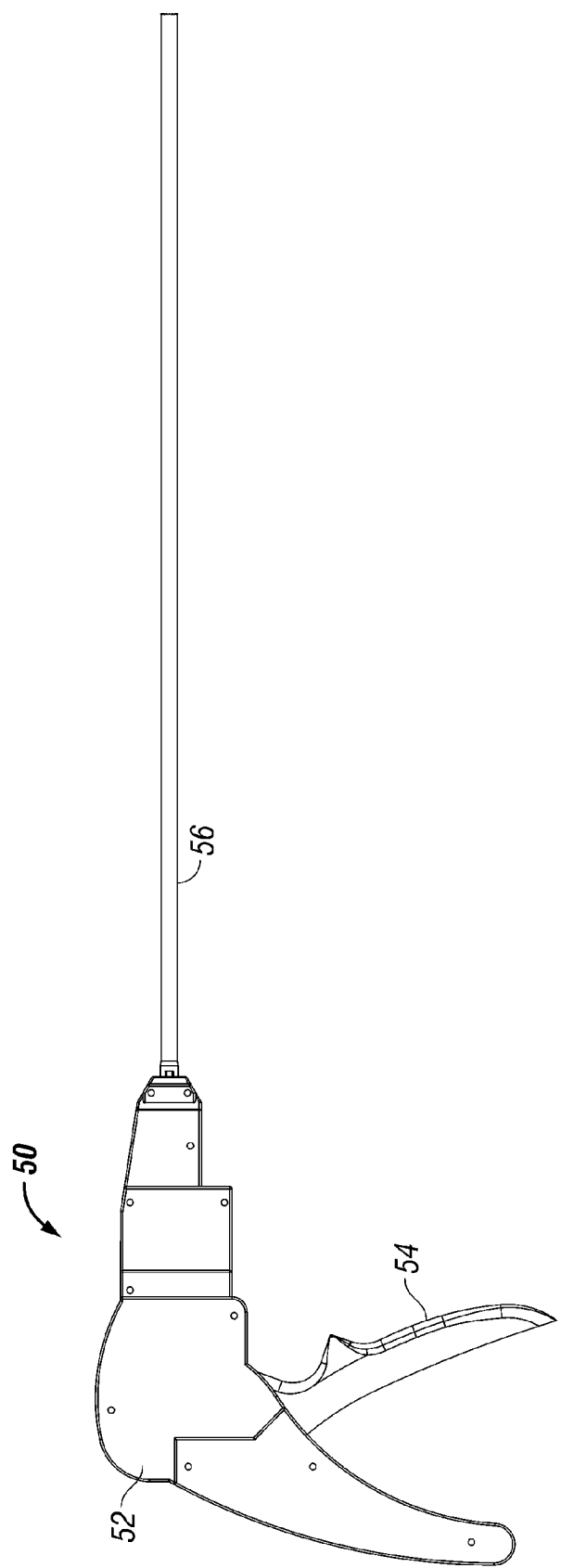
FIG. 3 is a side view of the multi-fire surgical instrument.

As best shown in FIGS. 1A, 1D and 1E, fastener 10 is provided with torque slots 30 which are configured to engage members of a drive assembly of the multi-fire surgical instrument. Torque slots 30 include head slots 32 formed in head 12 and thread slots 34 formed in buttress threads 16. In an alternative embodiment, thread slots 34 may be omitted leaving only head slots 32 for engagement with a drive assembly. As shown, fastener 10 has a through-bore 36 which allows fastener 10 to ride along a meeting part in the multi-fire surgical instrument so as to advance fastener 10 within the surgical instrument.

Referring now to FIGS. 2-5, there is disclosed an embodiment of a multi-fire surgical instrument 50 for installing fasteners 10 into tissue. Surgical instrument 50 generally includes a body 52 having a trigger 54 movably mounted to body 52. In the figures illustrated, body 52 is shown with sections open to view the internal components, however, it is contemplated that the actual commercial embodiment will have a body 52 which fully encloses the internal components of surgical instrument 50. Surgical instrument 50 as an outer tubular member 56 extending distally from body 52. Outer tubular member 56 is movably mounted to body 52. Specifically, outer tubular member 56 can move a limited distance distally and proximally relative to body 52. Outer tubular member 56 encloses a fastener cartridge subassembly and a drive subassembly as disclosed in more detail below.

Figure 4:
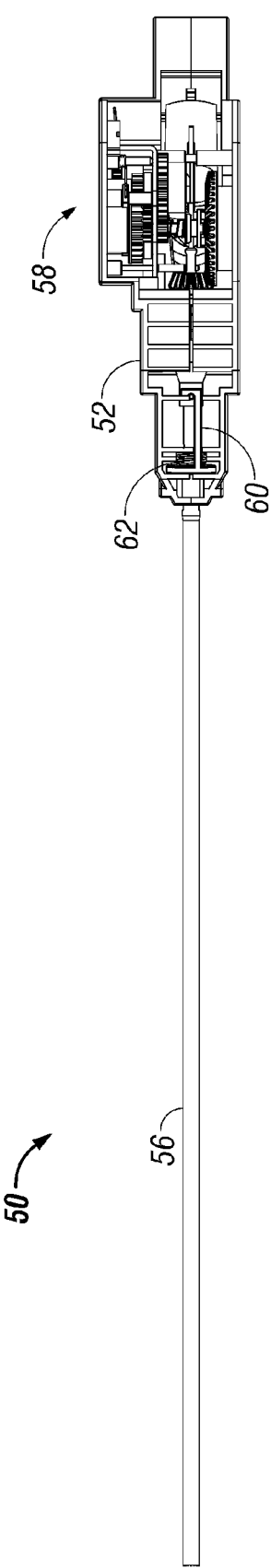
FIG. 4 is a top view of the multi-fire surgical instrument.

Referring now to FIG. 4, surgical instrument 50 includes a gear train 58 which is designed to convert linear motion of trigger 54 into rotary motion within outer tubular member 56. As is also shown in FIG. 4, surgical instrument 50 includes a novel lockout mechanism including a lockout member 60 which is biased within body 52 by spring 62. Lockout member 60 is provided to restrain or "lock" gear train 58, and thus prevent actuation of surgical instrument 50 until outer tubular member 56 has been moved to a proximal position.

Figure 5:
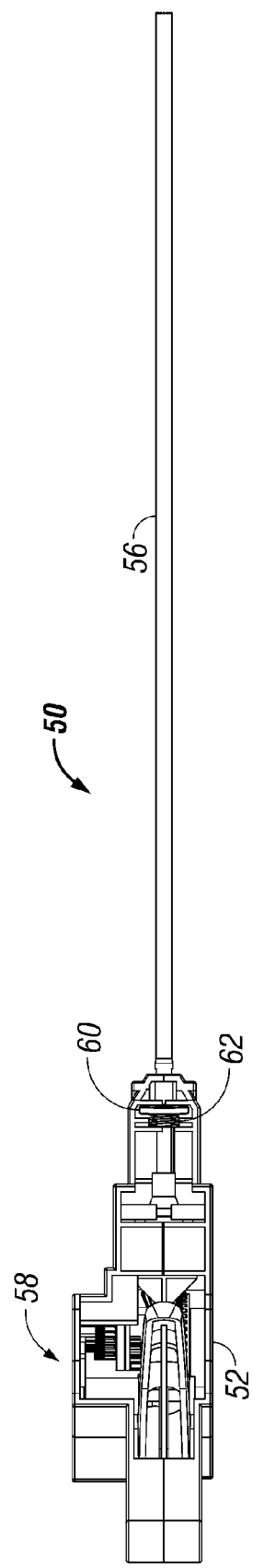
FIG. 5 is a bottom view of the multi-fire surgical instrument.
Figure 6:
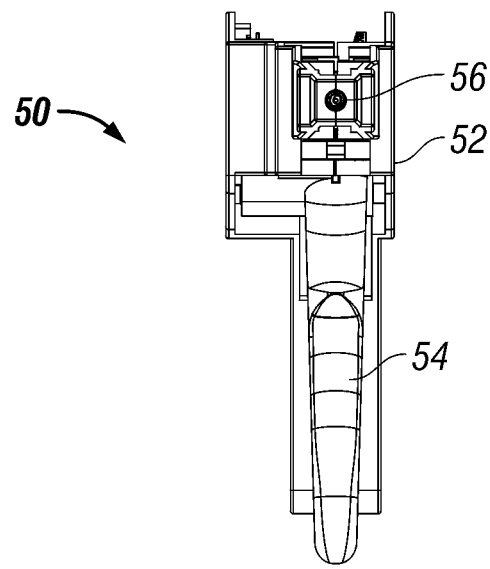
FIG. 6 is a front view of the multi-fire surgical instrument.
Figure 7:
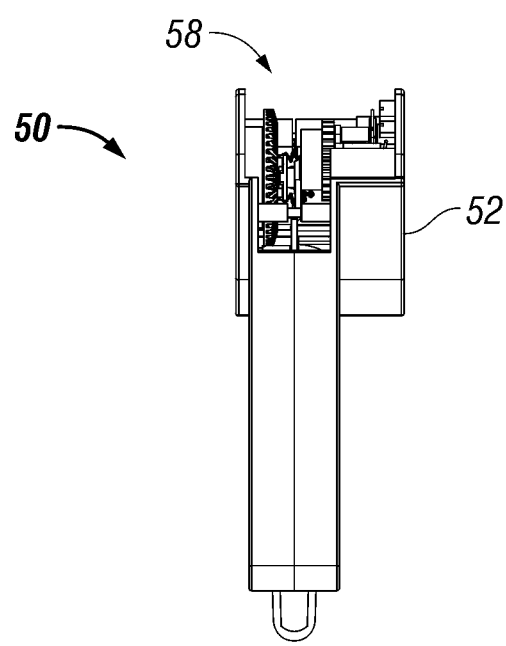
FIG. 7 is a rearview of the multi-fire surgical instrument.

FIGS. 5, 6 and 7 illustrates surgical instrument 50 as viewed from the bottom, the front, and the rear of surgical instrument 50, respectively. Gear train 58 is visible in FIGS. 5 and 7. A portion of lockout member 60 and lockout spring 62 is also visible in FIG. 5.

Figure 8:
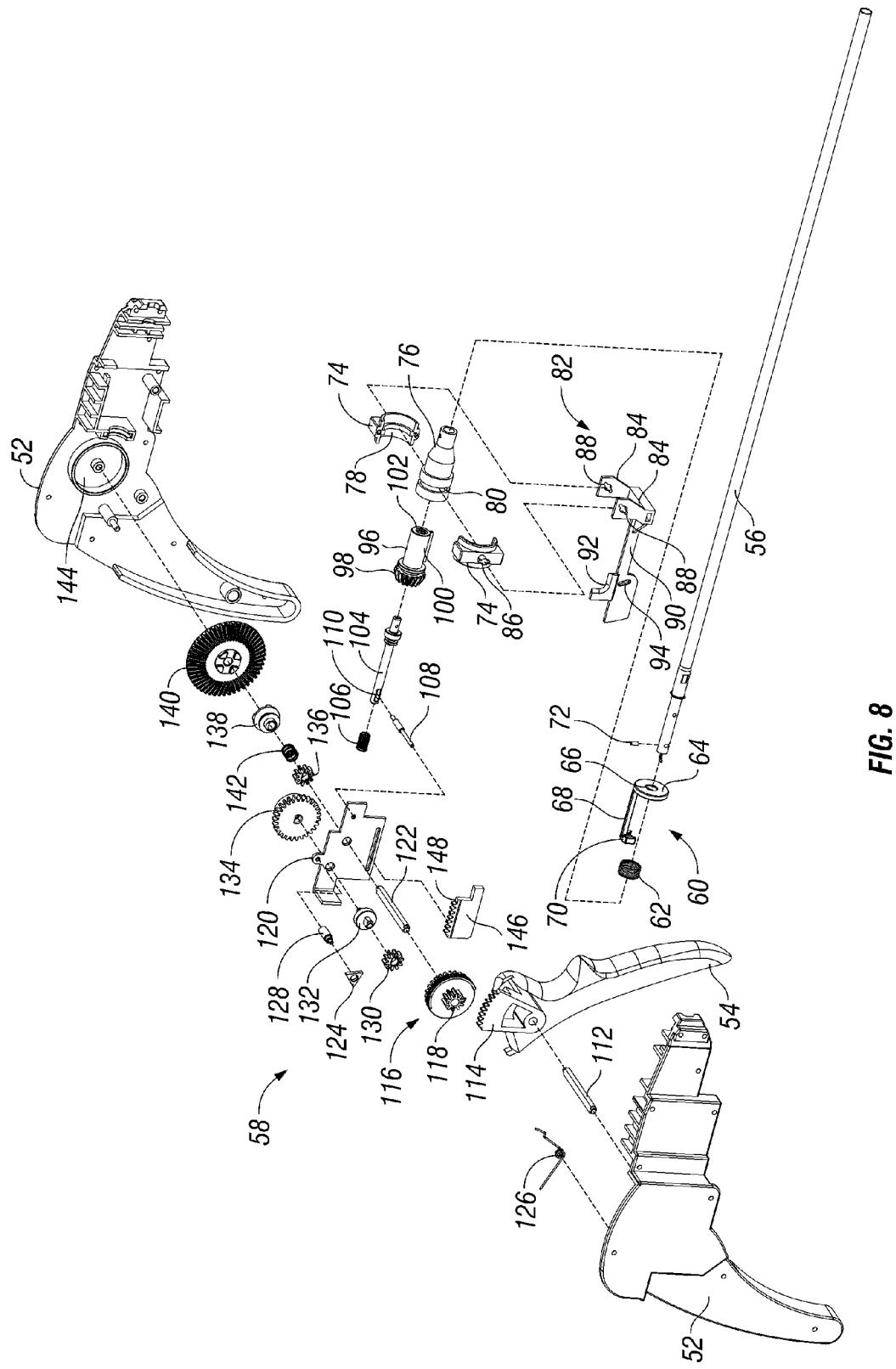
FIG. 8 is a perspective view of the multi-fire surgical instrument with the handle parts separated.

Referring now to FIG. 8, the details of the internal handle components will now be described. As noted hereinabove, lockout member 60 is provided to immobilize gear train 58 until such time as outer tubular member 56 is moved to a proximal position within handle 52. This ensures that surgical instrument 50 cannot be actuated until outer tubular member 56 is pressed against tissue. This avoids any inadvertent ejection of fasteners 10 and ensures that the distal end of outer tubular member 56 is properly positioned against mesh and/or tissue. Lockout member 60 generally includes a baseplate 64 having a bore 66 therethrough. Baseplate 64 provides a surface against which a proximal end of outer tubular member 56 can be biased. Bore 66 allows various driver and cartridge subassemblies to move therethrough as described in more detail below. Lockout member 60 further includes a proximally extending arm 68 which terminates in a hook 70. Hook 70 is configured to engage a torque pin 72 to prevent rotation of gear train 58. As noted hereinabove, lockout spring 62 biases lockout member 60 to a distal-most position and thus biases outer tubular member 56 distally relative to body 52.

A pair of rings 74 is provided to rotatably support a socket 76. Specifically, projections 78 formed in rings 74 cooperate with a socket groove 80 formed on socket 76. A link 82 is provided which serves several functions including supporting rings 74 and disabling gear train 58 after trigger 54 has been fully pulled proximally and a fastener 10 ejected. Link 82 includes brackets 84 which are configured to engage ring pins 86 on rings 74. Link 82 further includes a proximally extending arm 90 which terminates in a clutch cam 92. Clutch cam 92 is configured to disengage a clutch from a bevel gear associated with gear train 58. A slot 94 is provided in link 82 to allow link 82 to pivot upwardly to engage clutch cam 92 with a clutch.

A bevel pinion 96 is provided to engage drive assembly components extending through outer tubular member 56 as described in detail hereinbelow. Bevel pinion 96 includes bevel teeth 98 which are provided to engage a component of drive train 58. Bevel pinion 96 includes a tube 100 extending distally from bevel teeth 98 and is rotatably and longitudinally movable within socket 76. Bevel pinion 96 also includes a throughbore 102 for receipt of components associated with a needle assembly. Specifically, a needle coupling 104 is rotatably and longitudinally movable within bevel pinion 96 and is provided to attach to a proximal end of a needle extending through outer tubular member 56 to allow the needle to move longitudinally within outer tubular member 56. Needle coupling 104 has a needle spring 106 associated with it to bias needle coupling 104 within body 52. A needle pin 108 extends through a proximal slot 110 in needle coupling 104 to limit the proximal and distal travel distance of needle coupling 104 within body 52.

As noted hereinabove, trigger 54 is pivotally mounted within body 52. Trigger 54 is mounted on a trigger pin 112 which is affixed to both halves of body 52. A trigger spring (not explicitly shown in this embodiment) is also provided within body 52 to bias trigger 54 to an open or un-retracted position prior to actuation of surgical instrument 50. Trigger 54 is provided with a trigger gear 114 configured to engage a component of gear train 58.

Gear train 58 includes a variety of components which function together to transfer linear motion of trigger 54 into rotational motion of gear train 58 and thus to a drive assembly associated with surgical instrument 50. Gear train 58 includes a combination gear 116 which serves several functions. Combination gear 116 includes a trigger spur gear 118 which is engageable with trigger gear 114 of trigger 54. A gear plate 120 is provided within body 52 to support the various gear assemblies. Combination gear 116 is supported within body 52 by a D-pin 122 extending through gear plate 120. Combination gear 116 includes a ratchet feature which functions with a pawl 124 to prevent reverse rotation of combination gear 116 until trigger 54 has been fully depressed. Pawl 124 is biased into engagement with combination gear 116 by a pawl spring 126. Pawl 124 is supported within body 52 by a pawl pin 128.

Combination gear 116 is engageable with a first 10-tooth gear 130. First 10-tooth gear 130 is mounted to a coupling 132 which extends through gear plate 120. A 27-tooth gear 134 is provided on an opposite side of gear plate 120 and is mounted to coupling 132. A second 10-tooth gear 136 is mounted on D-pin 122 and is engageable with 27-tooth gear 134. A clutch 138 is mounted on one end of D-pin 122 such that rotation of D-pin 122 rotates clutch 138 within body 52. A large bevel gear 140 is engageable with clutch 138 to transfer rotational motion of clutch 138 to bevel pinion 96. A gear spring 142 biases clutch 138 into engagement with large bevel gear 140. A recess 144 in body 52 rotatably supports large bevel gear 140 within surgical instrument 50. As noted hereinabove, clutch cam 92 provided on link 90 allows clutch 138 to be disengaged from large bevel gear 140 to isolate the drive assembly of surgical instrument 50 from gear train 58 after a full actuation stroke.

Figure 9:
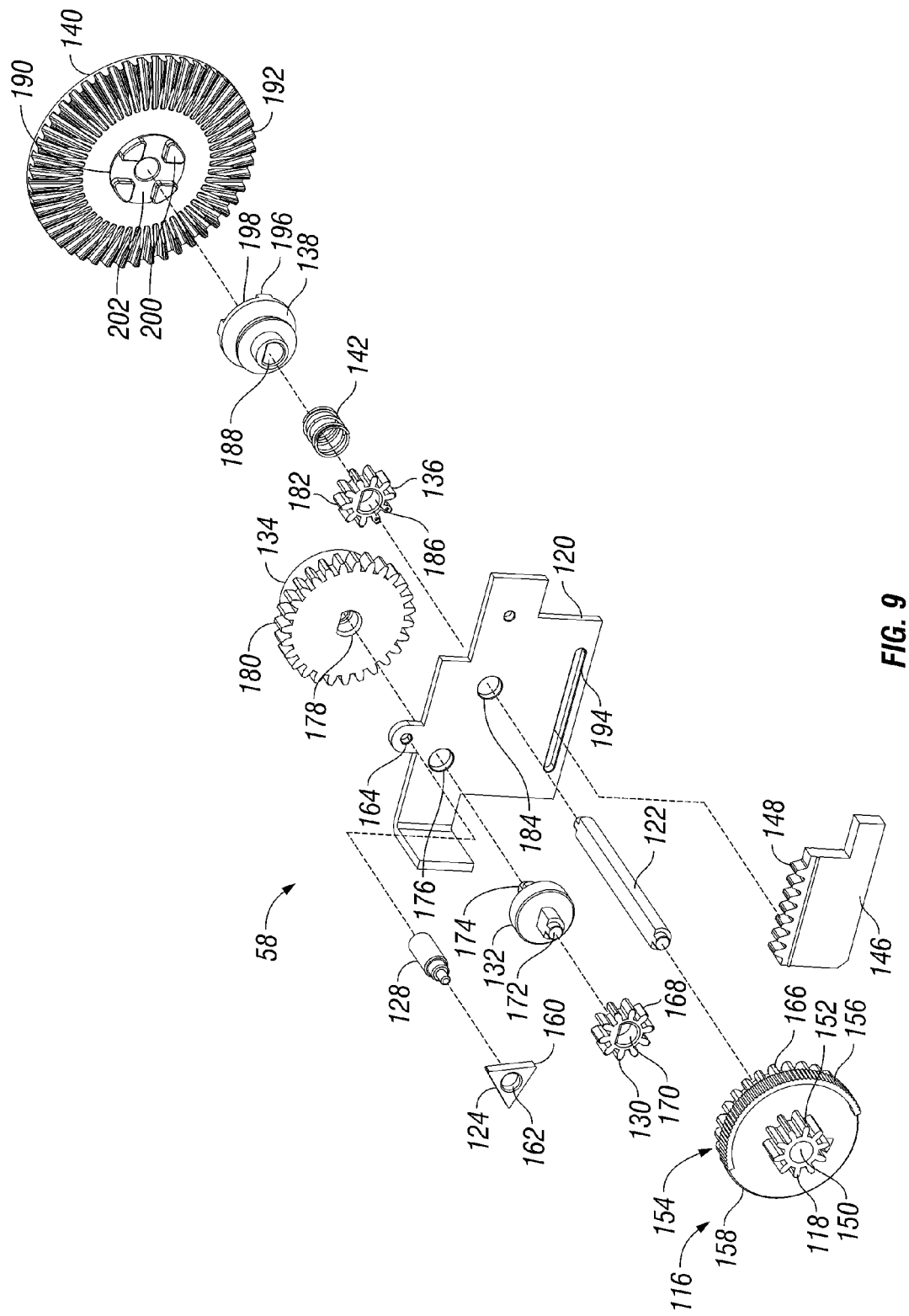
FIG. 9 is a perspective view of the gear train of the multi-fire surgical instrument with parts separated.

Referring now to FIG. 9, more specific details of gear train 58 are described. As noted above, combination gear 116 is rotatably mounted on D-pin 122. Combination gear 116 includes a circular throughbore 150 such that combination gear 116 can freely rotate on D-pin 122. Trigger spur gear 118 of combination gear 116 includes teeth 152 which are engageable with trigger gear 114. Thus, as trigger 54 is pivoted, trigger spur gear 118 engages teeth 152 to initiate rotation of gear train 58.

As noted hereinabove, combination gear 116 provides various functions including that of a ratchet feature. Ratchet feature 154 is includes components of pawl 124 and combination gear 116. Specifically, combination gear 116 includes toothed surface 156 and a smooth surface 158. Pawl 124 has a tooth or tip 160 which is configured to ride on toothed surface 156 and smooth surface 158. Tip 160 is oriented such that when riding on tooth surface 156 and as combination gear 116 is rotated clockwise as trigger 54 is depressed, combination gear 116 cannot rotate in a counterclockwise direction. Once trigger 54 has been completely depressed, tip 160 can ride on smooth surface 158 to allow trigger 54 to return to its initial position. As noted hereinabove, pawl 124 is rotatably mounted on a pawl pin 128. One end of pawl pin 128 extends through a bore 162 in pawl 124 while an opposite end of pawl pin 128 is mounted in a hole 164 in gear plate 120.

In order to transfer rotational motion of combination gear 154 to the remaining components of gear train 58, combination gear 154 includes gear teeth 166 which are engageable with gear teeth 168 on first 10-teeth gear 130. First 10-teeth gear 130 includes a D-shaped bore 170 which is configured to mount on a D-shaped pin 174 extending from one side of coupling 132 such that first 10-teeth gear 130 rotates with coupling 132. Coupling 132 includes a second D-shaped pin 174 which extends through a hole 176 in gear plate 120. D-shaped pin 174 engages a D-shaped bore 178 in 27-tooth gear 134 such that 27-tooth gear 134 rotates with coupling 132. 27-tooth gear 134 includes teeth 180 which are engageable with teeth 182 on second 10-tooth gear 136. D-pin 122 extends through a hole 184 in gear plate 120 and is engageable within a D-shaped hole 186 in second 10-tooth gear 136. D-pin 122 continues through clutch spring 142 and through a D-shaped hole 188 in clutch 138. D-pin 122 continues through a hole 190 formed in large bevel gear 140 and into a recess in body 52.

A series of teeth 192 is formed on large bevel gear 140 and is configured to engage teeth 98 on bevel pinion 96 which allows the rotational movement of gear train 58 to be transferred approximately 90° to bevel pinion 96 and thus to components of the cartridge and drive assemblies contained within outer tubular member 56.

It should be noted that gear plate 120 also includes a slot 194 for receipt of a shaft or pin (not shown) extending from rack 146 to transfer linear movement of rack 146 from one side of gear plate 120 to the opposite side of gear plate 120. This pin is configured to engage slot 94 in link 82 and move link 82 longitudinally within body 52.

As noted hereinabove, clutch 138 is engageable and disengageable with large bevel gear 140 enabling rotation of large bevel gear 140 when clutch 138 is engaged with large bevel gear 140. Thus, clutch 138 includes a series of interlocking teeth or projections 196 and recesses 198 which mate up with corresponding projections 200 and recesses 202 in large bevel gear 140. Thus, as trigger 54 is squeezed during actuation, the rotation imparted to combination gear 116 is translated to rotation of large bevel gear 140. The use of multiple parallel sets of gears on either side of gear plate 120 to transfer motion of trigger 54 to large bevel gear 140 helps gear efficiency by keeping the pitch diameters of all the mating gears tight together.

Figure 10:
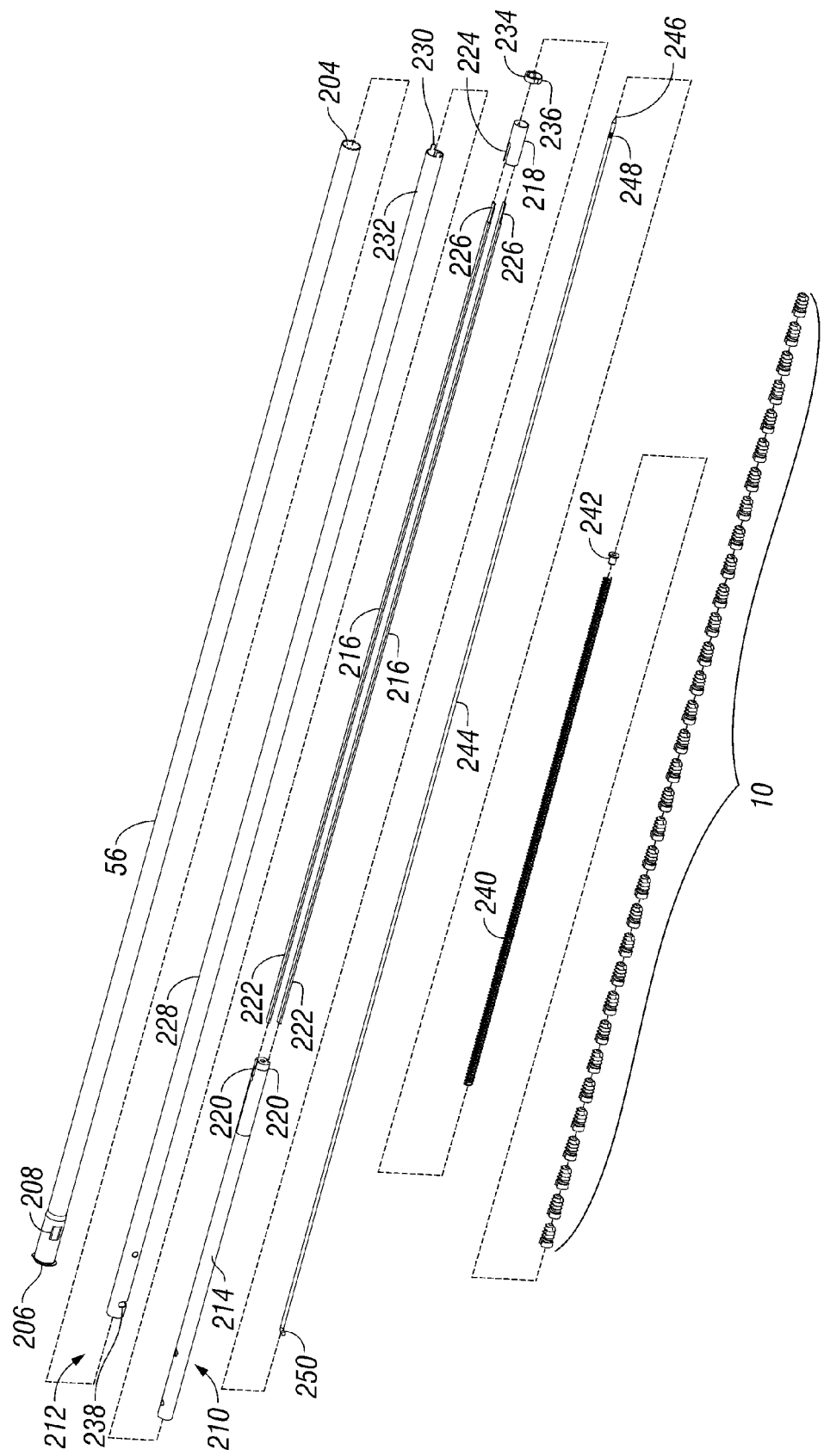
FIG. 10 is a perspective view of the distal end of the multi-fire surgical instrument with parts separated.

Referring now to FIG. 10, the specific details of the various components of the distal end of surgical instrument 50 are described. As noted hereinabove, surgical instrument 50 includes an outer tubular member 56 extending distally from body 52. Outer tubular member 56 is configured for longitudinal motion relative to body 52 over a limited predetermined distance. Outer tubular member 56 includes an open distal end 204 and an open proximal end 206. Flats 208 adjacent the proximal end of outer tubular member 56 allow for longitudinal motion of outer tubular member 56 within body 52.

Within outer tubular member 56 are contained a cartridge subassembly 210 and a driver subassembly 212. Cartridge subassembly 210 generally includes a proximal hollow tube 214, a pair of parallel beams 216 and a distal hollow tube 218. A pair of slots 220 is provided on proximal hollow tube 214 and engages proximal ends 222 of beams 216. A pair of slots 224 is provided on distal hollow tube 218 and engages stepped down distal ends 226.

Driver subassembly 212 generally includes a hollow tube 228 having tabs 230 at a distal end 232. Tabs 230 are configured to engage a torque ring 234 in order to rotate surgical fastener 10 into tissue. Tabs 230 engage slots 236 in torque ring 234. A proximal slot 238 is provided on hollow tube 228 for receipt of a torque pin as described in more detail hereinbelow.

A plurality of fasteners 10 is contained within cartridge subassembly 210. Fasteners 10 are biased distally within cartridge subassembly 210 by a compression spring 240. A pusher 242 is provided between compression spring 240 and fasteners 10.

A needle 244 is also contained within outer tubular member 56 and is longitudinally movable relative to body 52. Needle 244 is provided to facilitate piercing mesh and tissue in advance of the insertion of fastener 10. Needle 244 includes a pointed distal tip 246 and a retention feature 248 proximal of distal tip 246, the purpose of which is described in more detail hereinbelow. Needle 244 also includes a proximal hook 250 for engagement with needle coupling 104.

Figure 11:
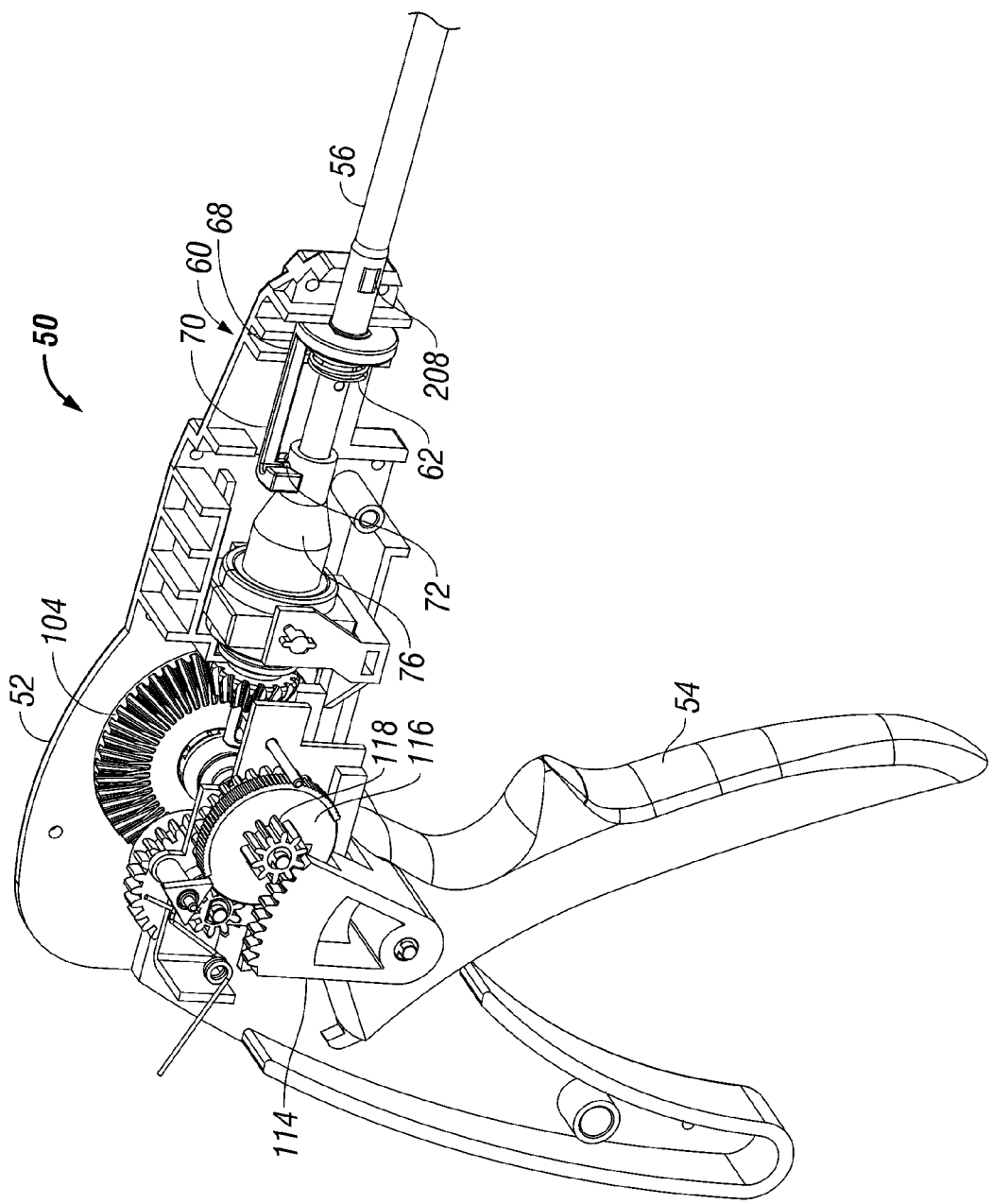
FIG. 11 is a perspective view of the proximal end of the multi-fire surgical instrument with one handle half removed.

Referring now to FIGS. 11-17, surgical instrument 50 is shown in various assembled configurations with certain parts removed for clarity. Referring initially to FIG. 11, surgical instrument 50 is shown with one body half 52 removed. Surgical instrument 50 is in the initial pre-fired state with outer tubular member 56 and lockout 68 in a distal-most position. Flats 208 of elongate tubular member 56 are also in the distal-most position relative to body half 52. Hook 70 constrains torque pin 72 which is press fit within socket 76. As shown, trigger 54 has yet to been moved such that trigger gear 114 is in an initial position relative to trigger spur gear 118 on combination gear 116.

Figure 12:
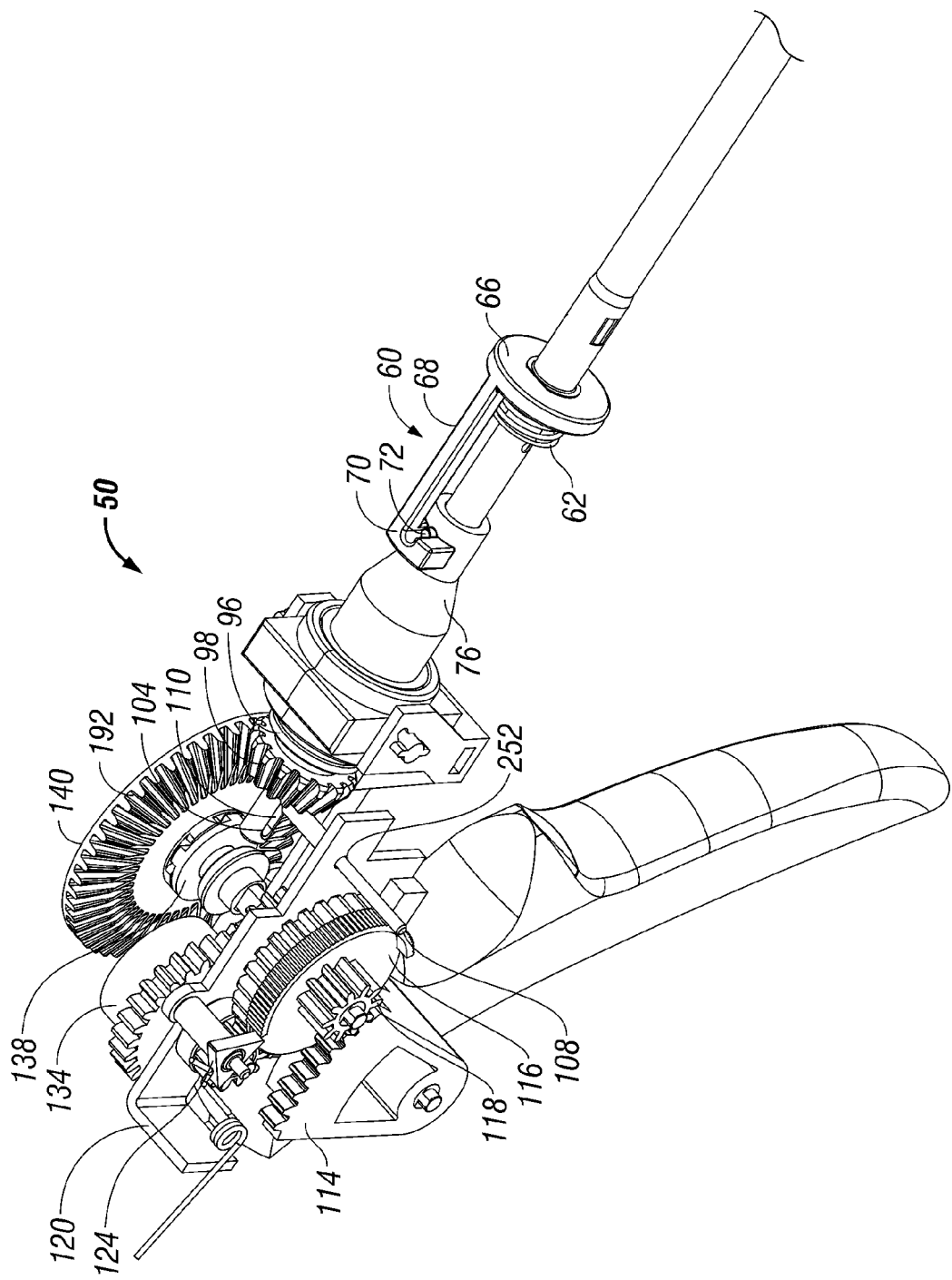
FIG. 12 is a perspective view of the proximal end of the multi-fire surgical instrument with both handle halves removed.

Referring now to FIG. 12, surgical instrument 50 is illustrated with both body halves 52 removed. Clutch 138 is shown engaged with large bevel gear 140 and teeth 192 of large bevel gear 140 are shown engaged with teeth 98 of bevel pinion 96. Pawl 124 is shown engaged with combination gear 116. A hole 252 is provided through gear plate 120 for receipt of needle pin 108 therethrough. As noted hereinabove, needle pin 108 extends into slot 110 in needle coupling 104 allowing needle 244 to move proximally and distally relative to body 52. Lockout member 60 is also shown in a distal-most position with hook 70 engaging torque pin 72.

Figure 13:
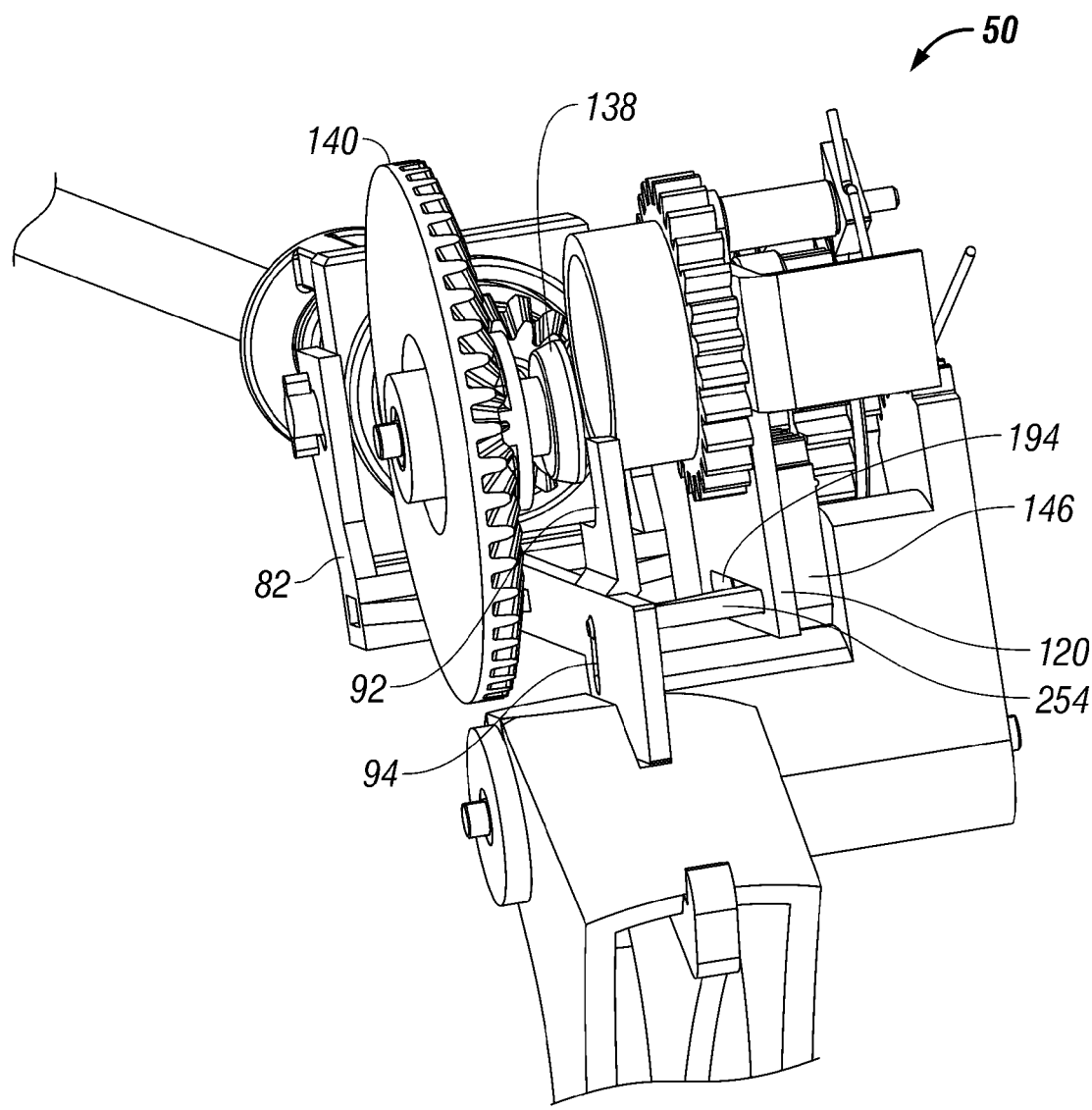
FIG. 13 is a perspective view, taken from the rear, of the proximal end of a multi-fire surgical instrument.

FIG. 13 illustrates surgical instrument 50 from a rearview with both body halves 52 removed. As shown, clutch 138 is engaged with large bevel gear 140. Link 82 is in a proximal-most position with clutch cam 92 remote from clutch 138. As noted hereinabove, link 82 is capable of linear motion through body 52 in response to movement of rack 146. Specifically, rack 146 includes a shaft 254 which extends through slot 194 in gear plate 120 and into slot 94 of link 82. As rack 146 moves distally or proximally it carries link 82 with it. Slot 94 is also provided to allow link 82, and specifically clutch cam 92, to pivot upwardly when link 82 has reached its distal-most position. At the distal-most position, clutch cam 92 cams clutch 138 away from large bevel gear 140 to separate the gear train 58 from large bevel gear 140 and allow pawl 124 to reset without rotation of large bevel gear 140.

Figure 14:
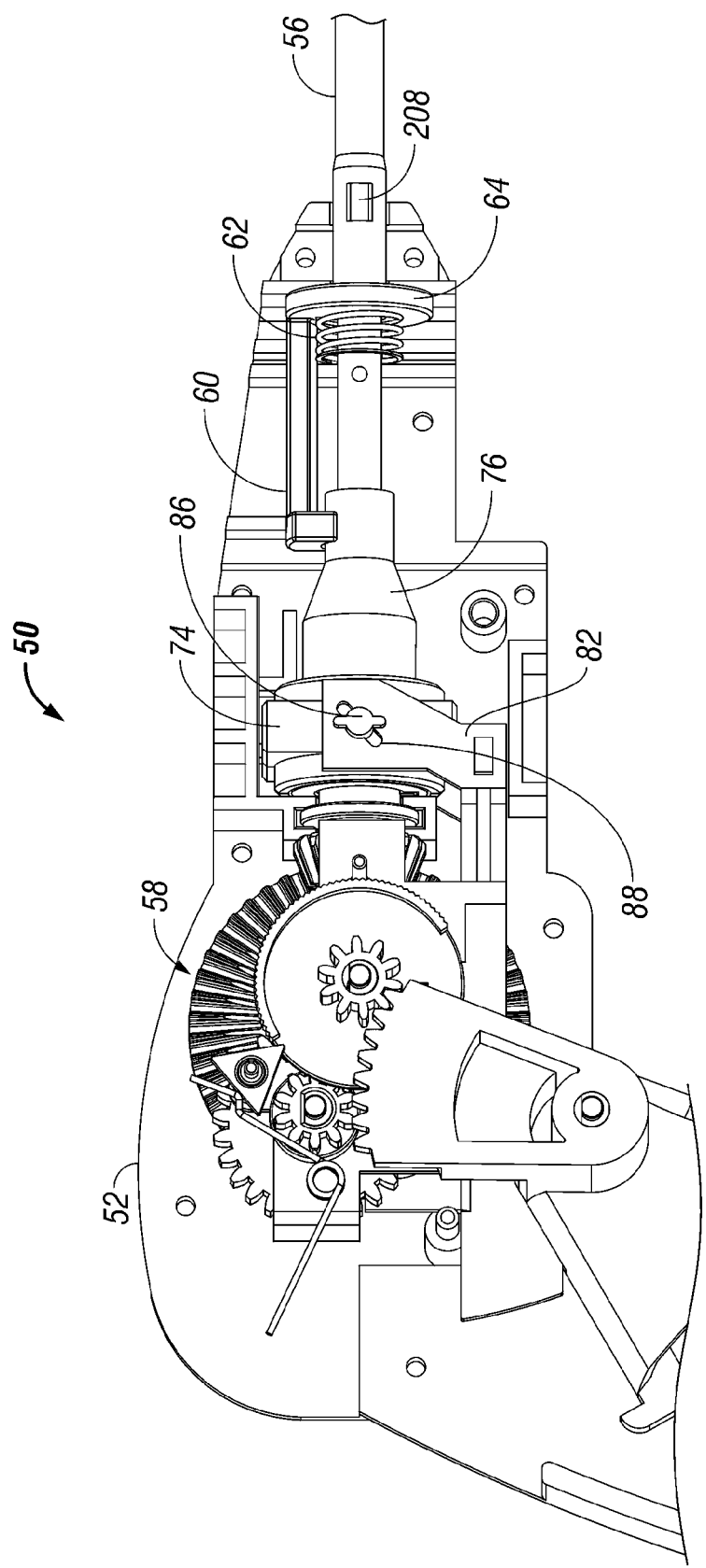
FIG. 14 is a side view of the proximal end of the multi-fire surgical instrument with a handle half removed.

Turning now to FIG. 14, surgical instrument 50 is shown from a side view with one body half 52 removed. Link 82 is in a proximal-most position while lockout member 60 is in a distal-most position against the bias of lockout spring 62. Additionally, baseplate 64 biases outer tubular member 56 to a distal-most position. As noted above, slots 208 in outer tubular member 56 allow for a limited range of longitudinal motion of outer tubular member 56 relative to body 52. Further, as noted above, link 82 is connected to socket 80 by way of rings 74 affixed around socket 76. Ring pins 86 on rings 74 extend through bracket slots 88 on link 82. Thus, as link 82 moves distally, socket 76 is also moved distally through body 52.

Figure 15:
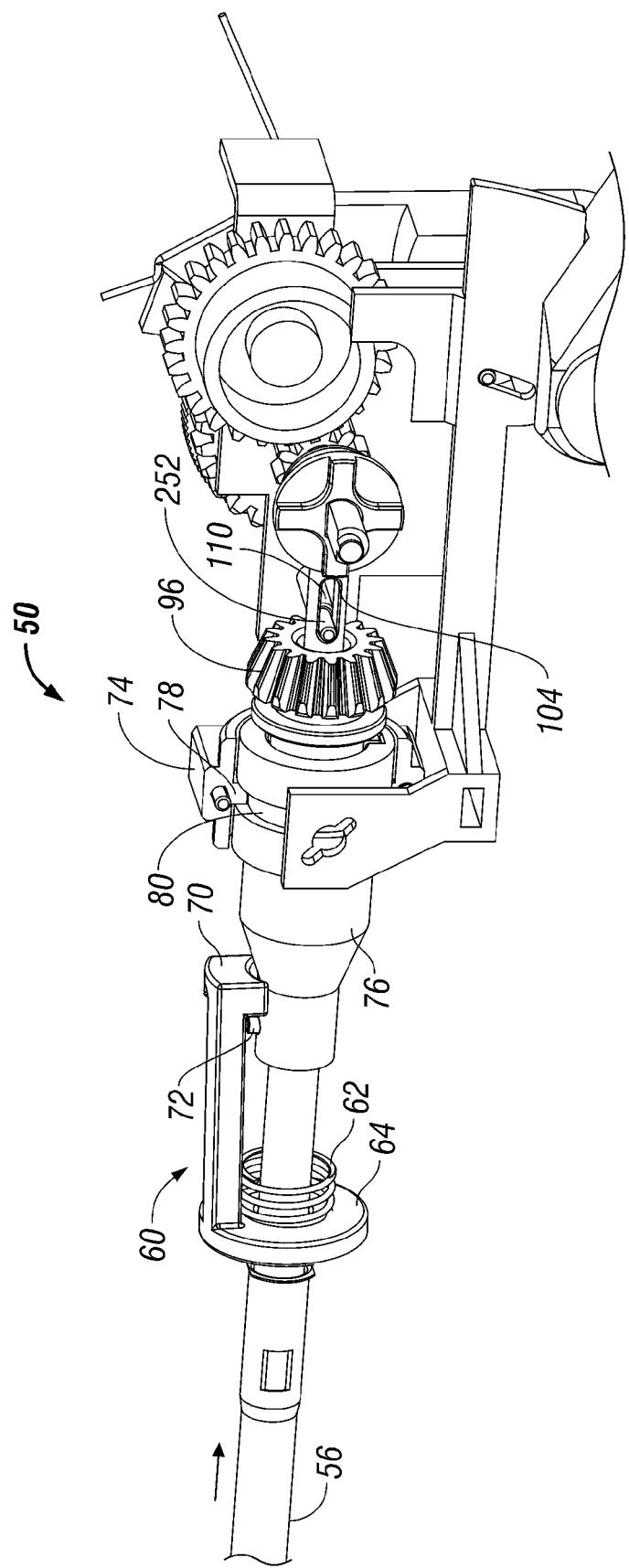
FIG. 15 is a perspective view of the proximal end of the multi-fire surgical instrument with both handle heads removed.

Referring to FIG. 15, surgical instrument 50 is illustrated with both body halves removed from a general side view. Large bevel gear 140 is not shown in this figure for clarity. As noted above, rings 74 engage and support socket 76 by way of projections 78 which extend into groove 80 on socket 76. As shown, outer tubular member 56 has been forced proximally against baseplate 64 of lockout member 60 and against the bias of lockout spring 62. This corresponds to an initial positioning of outer tubular member 56 against mesh and/or tissue and prior to actuation of surgical instrument 50. Hook 70 of lockout member 60 has moved off of torque pin 72 allowing socket 76 to rotate upon initial actuation of surgical instrument 50. Pin 252 is still in a proximal-most position within slot 110 in needle coupling 104.

It should be noted that cartridge and driver subassemblies 210 and 212, respectively, are pinned to socket 76 by means of torque pin 72. This allows the subassemblies to rotate and move linearly with socket 76, as discussed hereinbelow.

Figure 16:
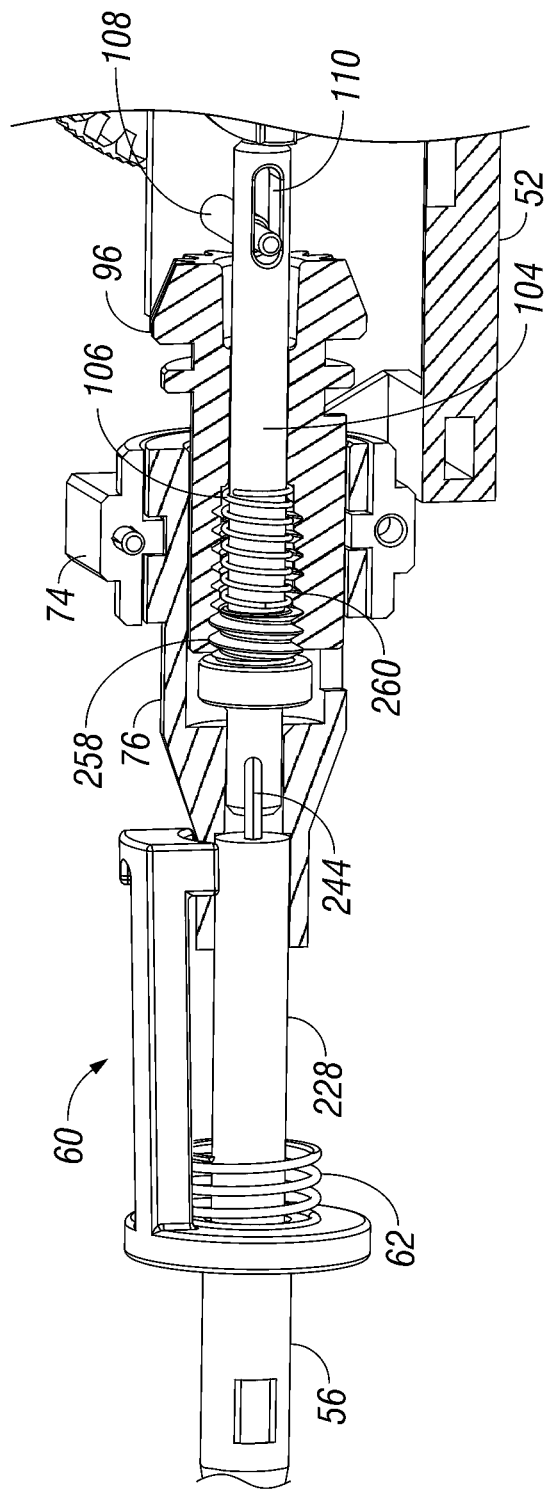
FIG. 16 is a perspective view of the proximal end of the multi-fire surgical instrument illustrating the lockout mechanism.

Referring now to FIG. 16, the internal connections between needle coupling 104 and bevel pinion 96 are described. In order for fastener 10 to be inserted through mesh and/or into tissue, needle 244 is used to punch an initial hole through the mesh and/or tissue. Rotation of bevel pinion 96 moves needle coupling 104 distally and proximally relative to bevel pinion 96. Needle coupling 104 may move proximately at a distance of about 3.5 mm. When threads 258 on needle coupling 104 disengage from threads 260 on bevel pinion 96, needle coupling 104 ceases its linear movement. Coupling spring 106 keeps needle coupling 104 from reengaging bevel pinion 96 until a later sequence where needle 244 is retracted.

Since needle pin 108 extends through slot 110 in needle coupling 104, needle coupling 104 cannot rotate with bevel pinion 96. Additionally, slot 110 limits the distal and proximal travel of needle coupling 104 and thus of needle 244. Bevel pinion 96 is keyed into slots (not explicitly shown) of socket 76, which allows for translation of socket 76. When needle coupling 104 is disengaged from bevel pinion 96, socket 76 can continue to rotate and travel linearly. This allows fastener 10 to rotate and travel farther than needle 244. As noted hereinabove, needle 244 extends from needle coupling 104 through the cartridge and driver subassemblies, 210 and 212, respectively, to the distal end of surgical instrument 50.

Figure 17:
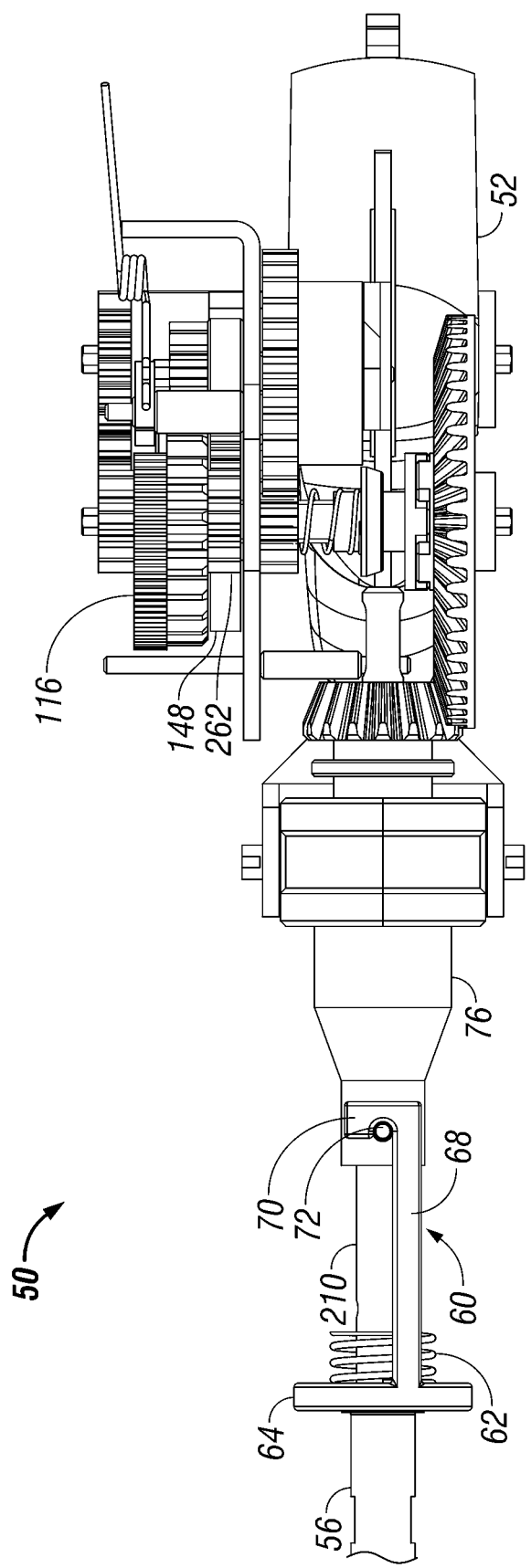
FIG. 17 is a top view of the proximal end of the multi-fire surgical instrument with both handle halves removed.

Turning now to FIG. 17, various assembled components of surgical instrument 50 are visible from a top view. As shown, lockout member 60 rides on an outer surface of driver subassembly 210 and constrains torque pin 72 on socket 76 against movement until such time as lockout member 60 has been biased proximally as outer tubular member 56 engages a target area and moves proximally. As noted hereinabove, combination gear 116 includes a spur gear 262 which engages rack 148 and moves the rack 148 proximally and distally within body 52.

Figure 18:
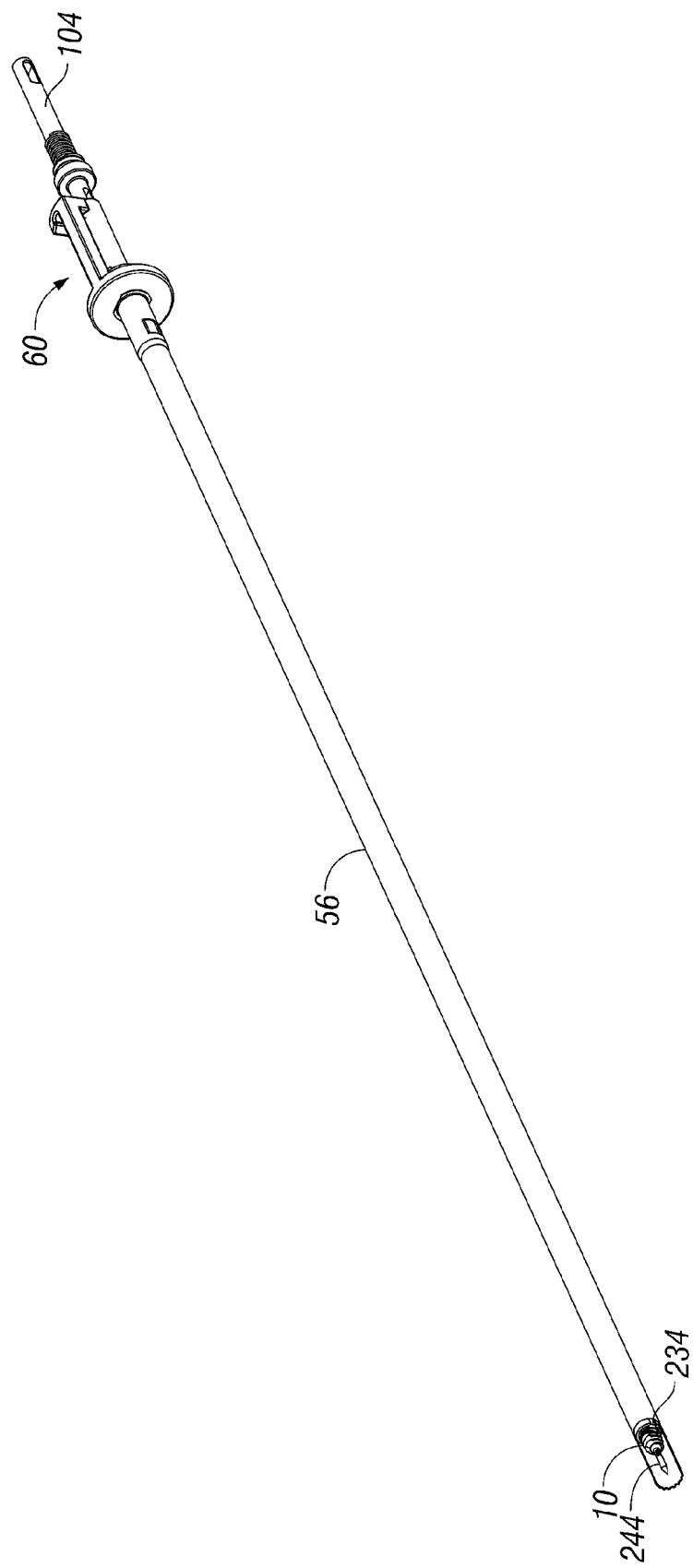
FIG. 18 is a perspective view, partially shown in section, of the distal end of the multi-fire surgical instrument.

Referring to FIG. 18, outer tubular member 56 is shown sectioned at its distal end to reveal fastener 10 and needle 244. As noted hereinabove, driver subassembly 212 has a hollow tube 228 with a slot 238 at its proximal end. Torque ring 234 is located adjacent distal end 232 of hollow tube 228. Torque ring 234 includes slots 236 thereon for engagement with tabs 237 (see FIG. 29) on cartridge subassembly 210 and tabs 230 on distal end of driver assembly 228. This interaction between slots 236 and tabs 230, 237 helps distal alignment of cartridge beams 216 (see FIG. 29) and torque ring 234.

Figure 19:
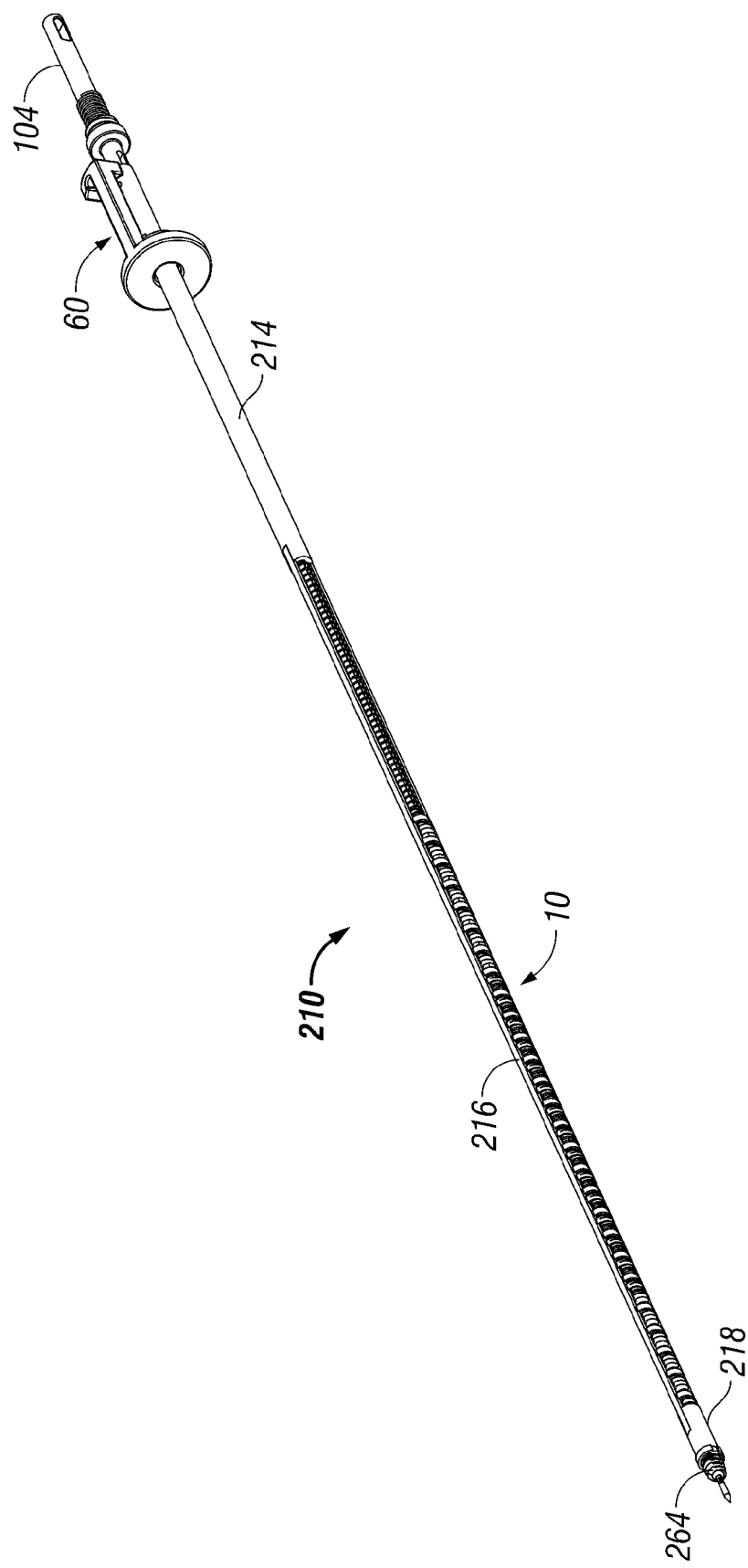
FIG. 19 is a perspective view of the distal end of the multi-fire surgical instrument with the outer tube removed.

Cartridge subassembly 210 is illustrated in the assembled condition in FIG. 19. As described hereinabove, cartridge subassembly 210 includes a proximal tube 214, a pair of beams 216 extending distally from proximal tube 214 and a hollow distal tube 218 affixed to the opposed ends of beams 216. Fasteners 10 are constrained within cartridge subassembly 210 by engagement of torque slots 30 (FIG. 1) with beams 216. As shown, all fasteners 10 are constrained within cartridge subassembly 210 except for a distal-most fastener 264 which is retained by torque ring 234. While not explicitly shown, spring 240 and pusher 242 bias fasteners 10 distally within cartridge subassembly 210.

Figure 20:
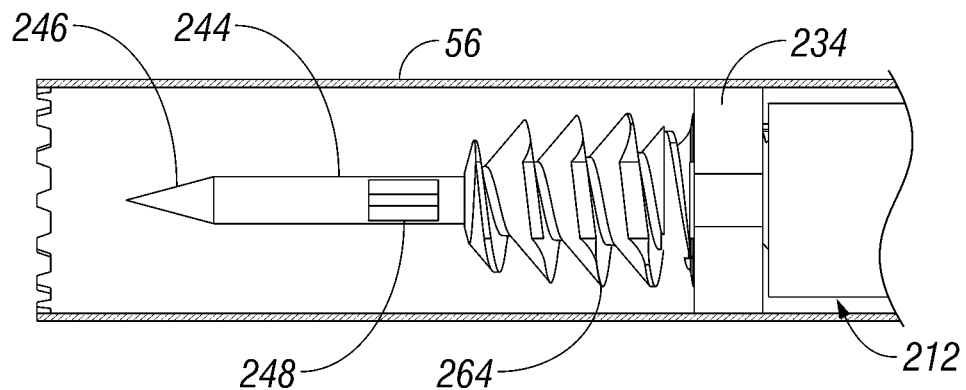
FIG. 20 is a side view, shown in section, of the distal-most end of the multi-fire surgical instrument.

Referring now to FIG. 20, the distal end of surgical instrument 50 is shown, partially in section, with the distal components assembled. Specifically, needle 244 is positioned within outer tubular member 56 and extends through driver subassembly 212. In the initial unfired position, sharp tip 246 of needle 244 is retracted within outer tubular member 56. The initial, or first, distal-most fastener 264 is positioned over needle 244 and retained in position by torque ring 234 and needle retention feature 248. As noted hereinabove, surgical instrument 50 is supplied with distal-most fastener 264 separated from the remaining fasteners 10 which are contained in the cartridge subassembly 210. In this state, surgical instrument 50 is ready to be used to apply distal-most fastener 264, and the remaining fasteners 10, to surgical mesh and/or tissue.

The use of surgical instrument 50 to apply fasteners 10 to secure a mesh to tissue is described. Initially, referring to FIGS. 21-25, there is illustrated the procedure for disengaging the lockout mechanism, i.e., disengaging lockout member 60 from torque pin 72 on socket 76 so that gear train 58 can rotate and surgical instrument 50 can be actuated. As noted above, the lockout mechanism is used to prevent actuation of the instrument until desired. Additionally, the lockout mechanism forces the distal end of surgical instrument 50 to be firmly seated against the mesh before it can be actuated.

Figure 21:
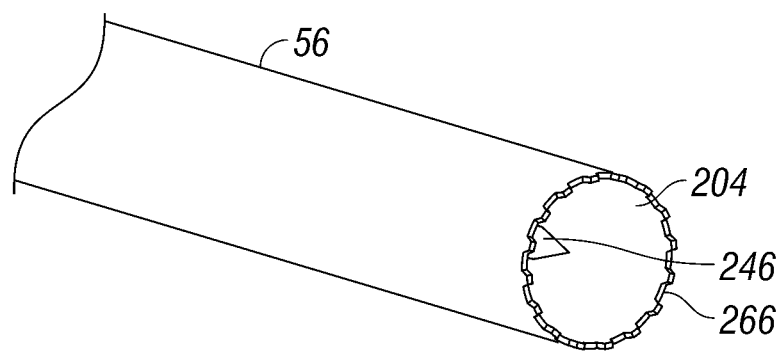
FIG. 21 is a perspective view of the distal-most end of the multi-fire surgical instrument.

Referring to FIG. 21, the distal end of outer tubular member 56 is illustrated with sharp needle tip 246 in a retracted position. A series of small projections or crenellations 266 are formed on the distal end of outer tubular member 56 about opening 204. Crenellations 266 hold the mesh taught against tissue and prevent the mesh from twisting when needle 244 punches through the mesh as distal-most fastener 264, as well as following fasteners 10, are inserted to the mesh and into tissue.

Figure 22:
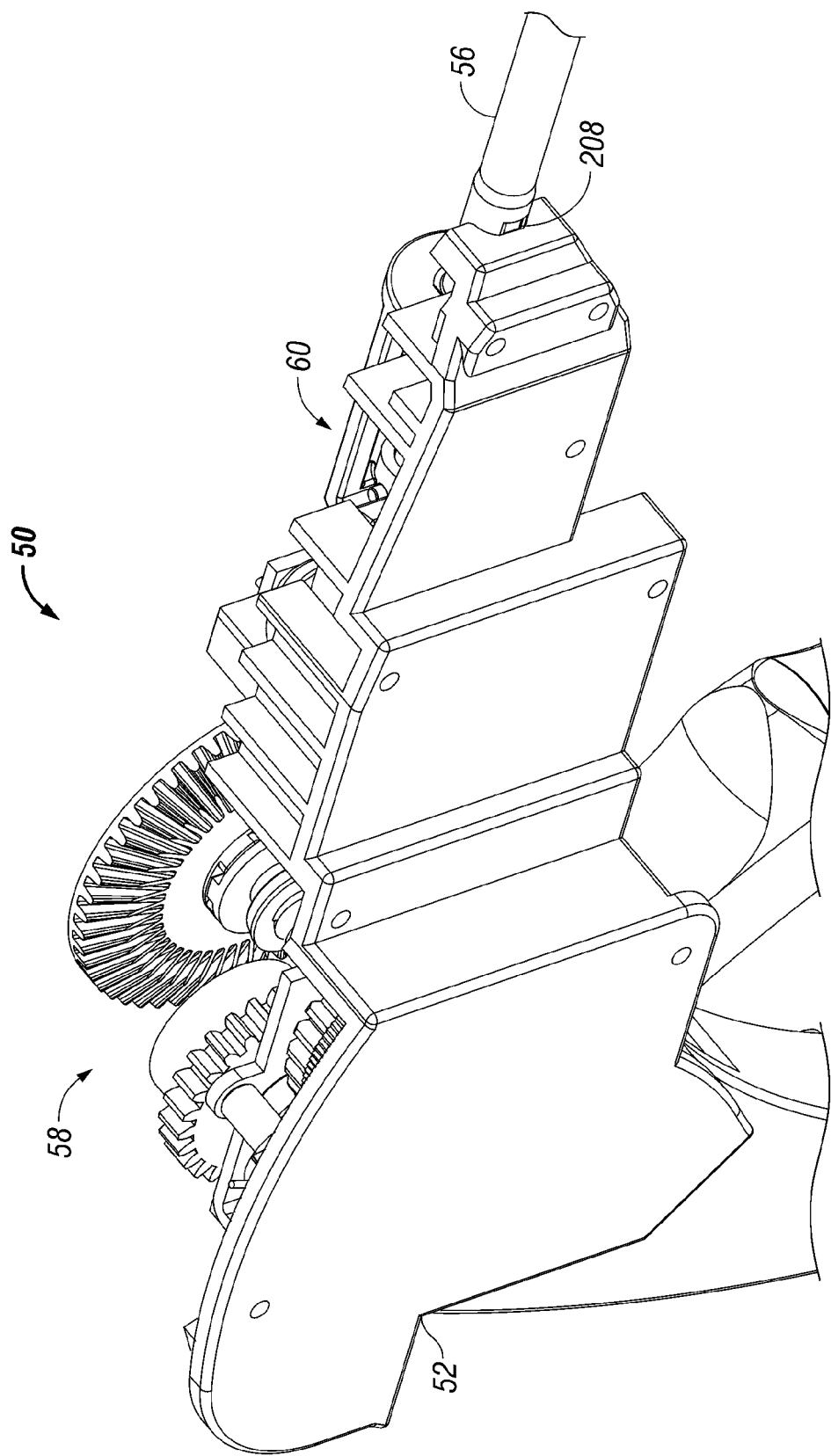
FIG. 22 is a perspective view of the proximal end of the multi-fire surgical instrument at the beginning of the lockout sequence.

Referring for the moment to FIG. 22, flats 208 on a proximal end of outer tubular member 56 mate with corresponding flats formed on the distal end of body 52. Flats 208 prevent outer tubular member 56 from rotating along with cartridge and driver subassemblies 210 and 212, respectively, as gear train 58 is actuated, while still allowing outer tubular member 56 to travel linearly. It should be noted that, in alternative embodiments of surgical instrument 50, other features may be provided to prevent outer tubular member 56 from rotating while allowing it to travel linearly, such as, for example, direct connections to lockout member 60.

Figure 23:
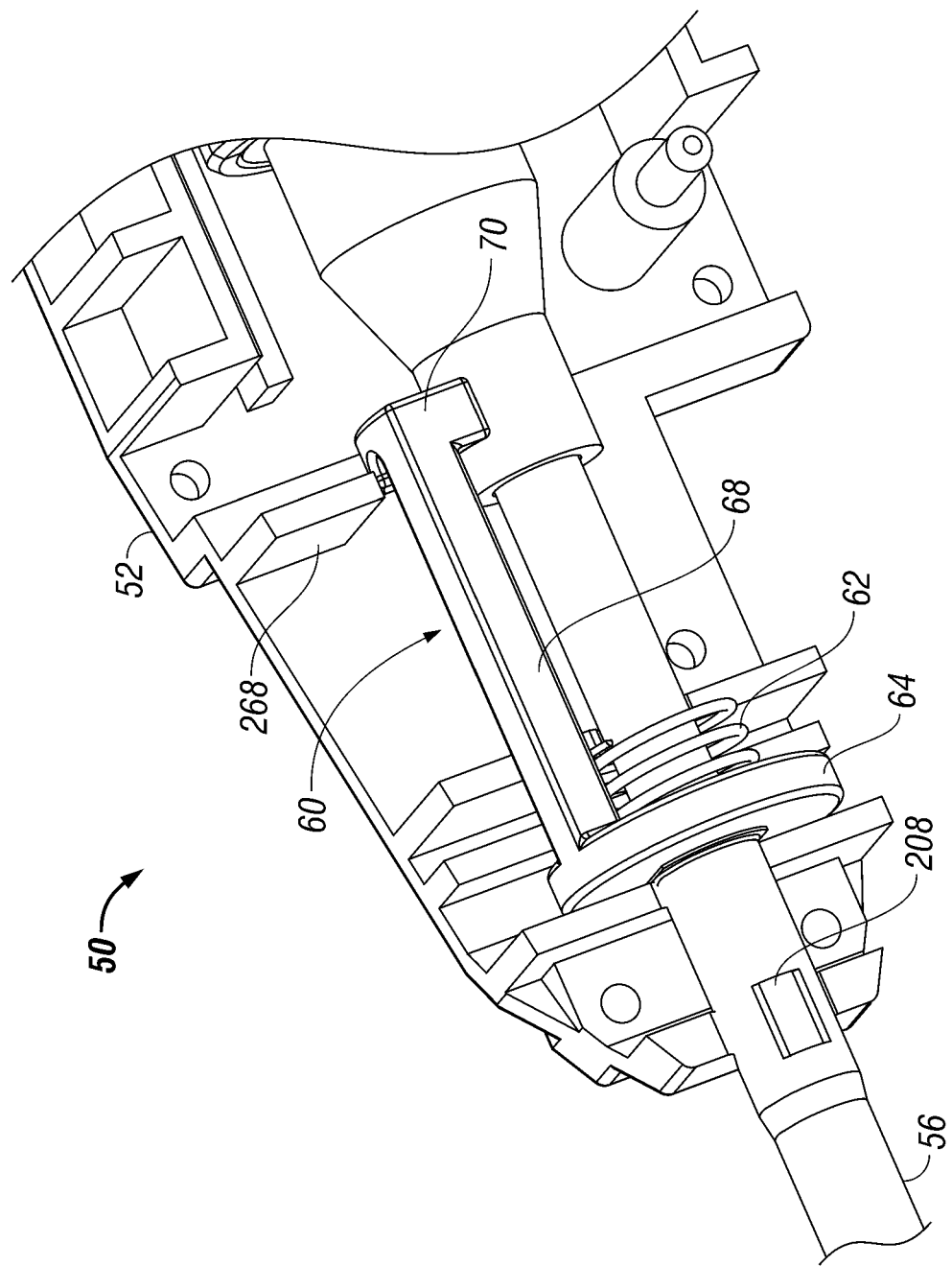
FIG. 23 is a perspective view of the lockout mechanism immediately prior to being deactivated.

As described hereinabove, lockout member 60 engages torque pin 72, affixed to socket 76, which prevents gear train 58 from rotating and thus prevents trigger 54 from being moved. Referring to FIG. 23, the proximal end of outer tubular member 56 rests against baseplate 64 of lockout member 60. Lockout spring 62 biases lockout member 60, and thus outer tubular member 56, in a distal-most position. In this initial position, hook 70 surrounds and holds torque pin 72 against movement (see FIG. 11). As shown in the initial position, lockout member 60, and specifically hook 70, is prevented from moving in the vertical direction by ribs 268 formed on body halves 52. This ensures that torque pin 72 is securely constrained by hook 70.

Figure 24:
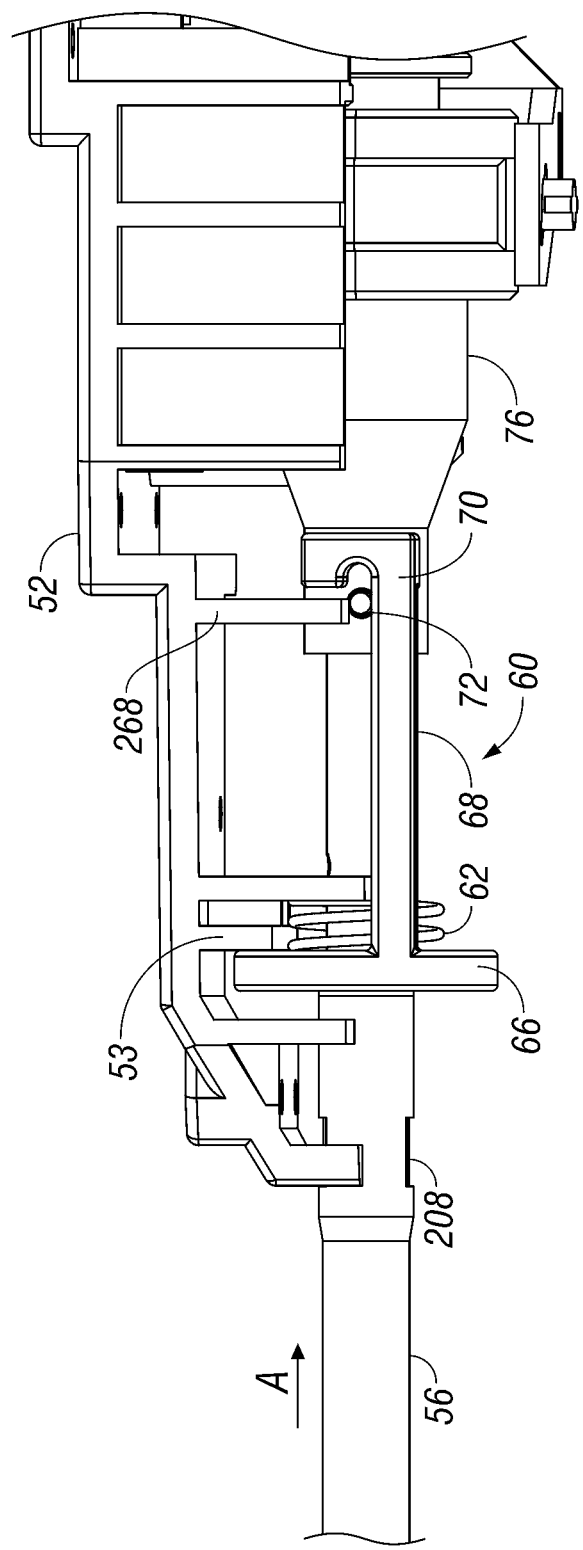
FIG. 24 is a top view illustrating the lockout mechanism deactivated.

Referring now to FIG. 24, in use, the surgeon inserts surgical instrument 50 through an access port and applies the distal end of outer tubular member 56 against mesh and tissue. The distal end of outer tubular member 56 is then forced against the mesh and tissue with a predetermined amount of force sufficient to overcome the bias of lockout spring 62. In one embodiment, lockout spring 62 can be overcome with a force of approximately 2 pounds. It should be noted that a lockout spring 62 can be chosen such that it can be overcome by forces of more or less than 2 pounds depending upon the intended application of surgical instrument 50. As shown, when outer tubular member 56 is urged against tissue, outer tubular member 56 is forced proximally relative to body 52 in the direction of arrow A. The length of travel of outer tubular member 56 is limited by a body rib 53. A portion of lockout member 60 contacts body rib 53, this prohibiting continued proximal movement of outer tubular member 56. As outer tubular member 56 is forced proximally, outer tubular member 56 forces lockout member 60 proximally against the bias of lockout spring 62. As lockout member 60 moves proximally, hook 70 disengages from torque pin 72 and moves out from underneath ribs 268. (See also FIG. 15). Once lockout member 60 is disengaged from torque pin 72 on socket 76, gear train 58 is freed up for rotation, i.e., trigger 54 can now be depressed.

Figure 25:
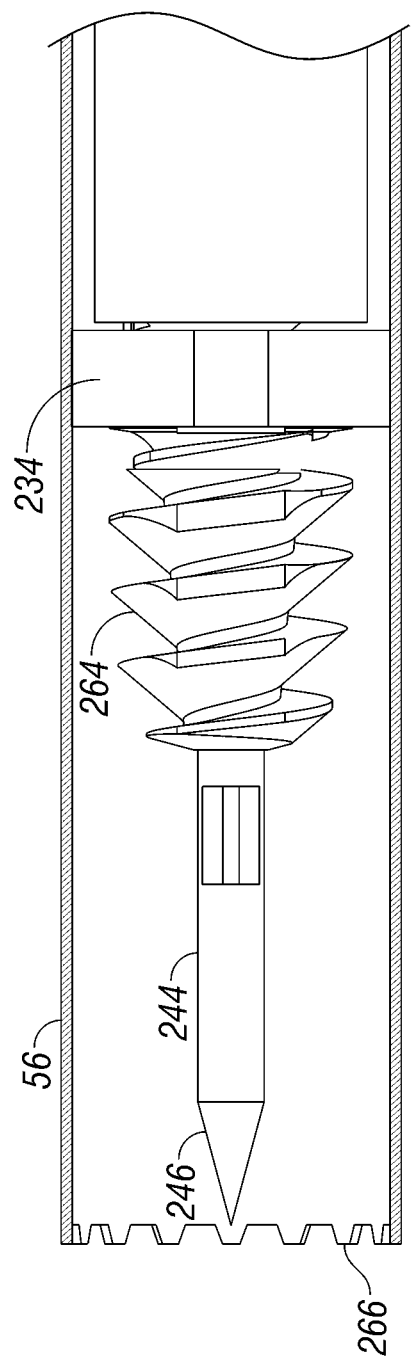
FIG. 25 is a side view, partially shown in section, of the distal-most end of the multi-fire surgical instrument during deactivation of the lockout mechanism.

Referring for the moment to FIG. 25, the distal end of surgical instrument 50 is shown with outer tubular member 56 in a retracted position and needle tip 246 of needle 244 in approximate alignment with crenellations 266. At this point, the lockout sequence has been completed and needle 244 is in a position to puncture mesh and tissue.

Referring now to FIGS. 26-31, the initial actuation of surgical instrument 50 will now be described. During this initial actuation by squeezing trigger 54, cartridge subassembly 210 is rotated or indexed approximately 90° relative to outer tubular member 56. At this point in the actuation sequence, driver subassembly 212 does not rotate. This initial actuation and indexing of cartridge subassembly 210 isolates distal-most fastener 264 from the remaining fasteners 10 in cartridge subassembly 210. Additionally, rotating cartridge subassembly 210 approximately 90° aligns stepped down distal ends 226 of beams 216 with a proximal face of distal-most fastener 264.

Figure 26:
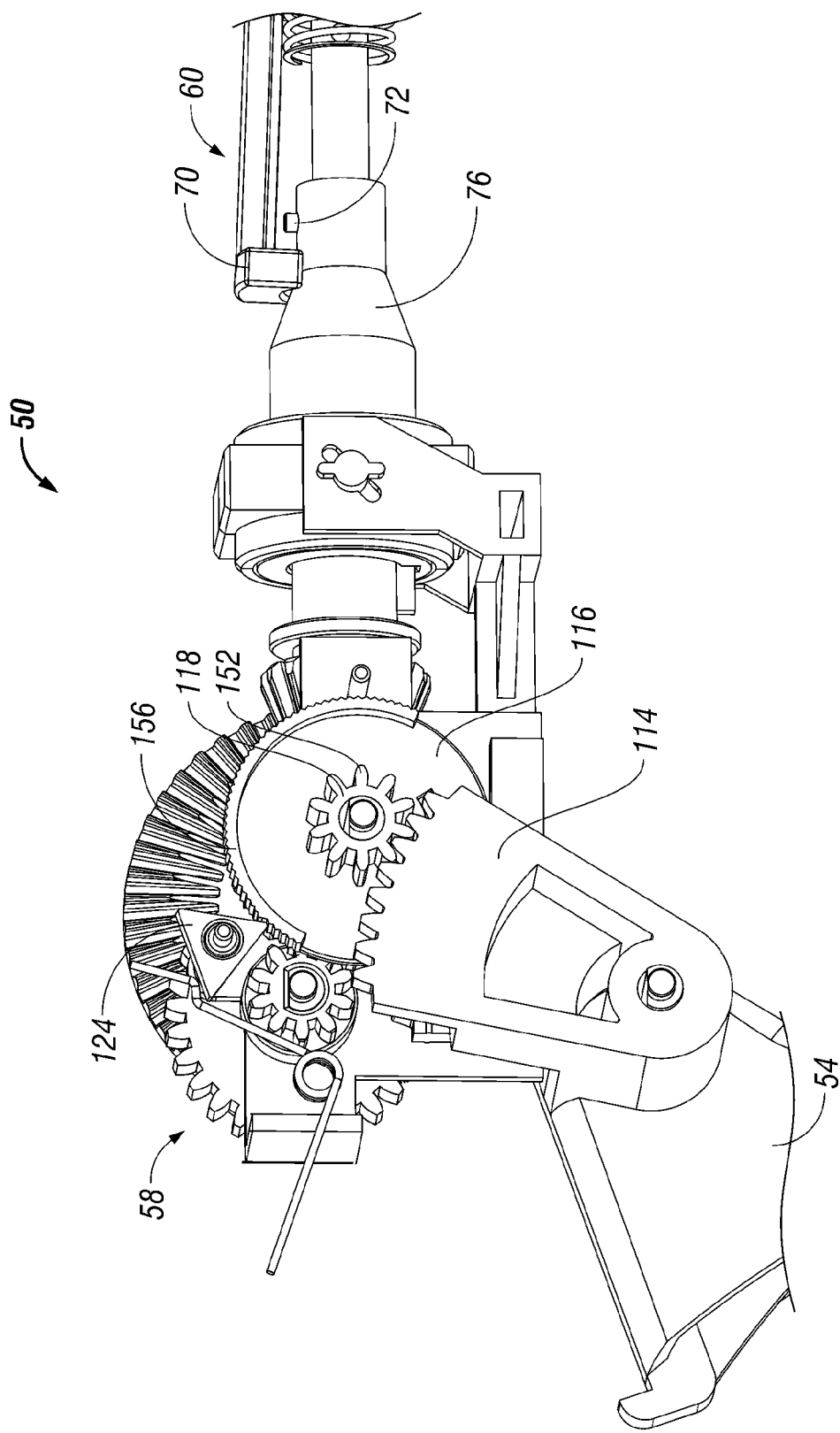
FIG. 26 is a perspective view of the proximal end of the multi-fire surgical instrument, with both handle halves removed, during initial actuation of the trigger.

Referring to FIG. 26, as trigger 54 it is initially depressed, trigger gear 114 engages teeth 152 on trigger spur gear 118 and begins to rotate trigger spur gear 118 and thus combination gear 116. As combination gear 116 begins to rotate, pawl 124 begins to ride over toothed surface 156 on combination gear 116. As noted hereinabove, engagement of pawl 124 with toothed surface 156 prevents gear train 58 from reversing until trigger 54 has been fully depressed. As shown, hook 70 of lockout member 60 is disengaged from torque pin 72 and socket 76 has not yet begun to rotate.

Figure 27:
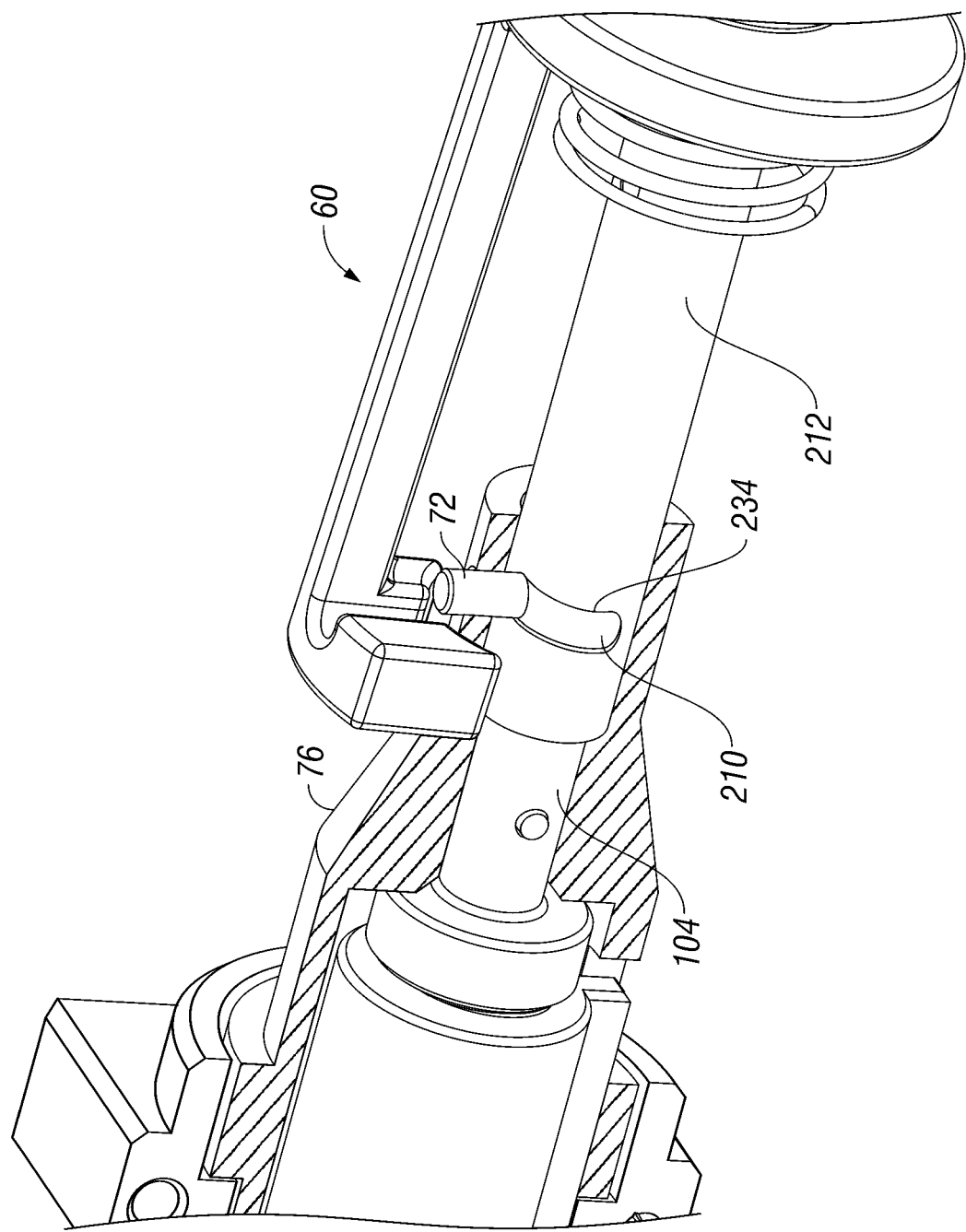
FIG. 27 is a perspective view of the proximal end of the multi-fire surgical instrument with the cartridge assembly in an initial position.
Figure 28:
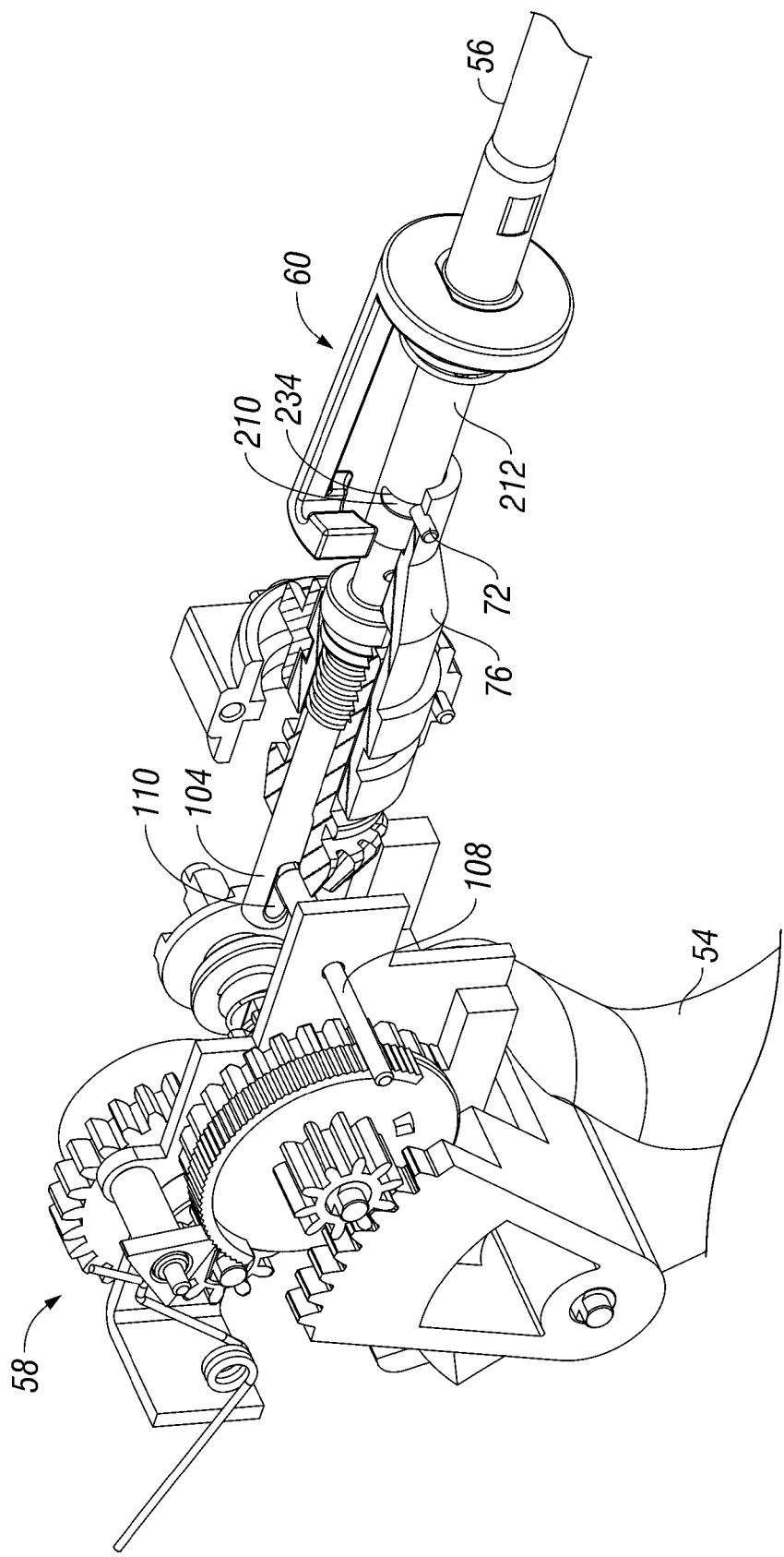
FIG. 28 is a perspective view of the proximal end of the multi-fire surgical instrument with the cartridge assembly indexed 90°.

Referring now to FIGS. 27 and 28, and initially with regard to FIG. 27, the rotation of cartridge subassembly 210 is described. As shown, torque pin 72 is press fit in socket 76. Torque pin 72 extends through slot 234 in driver subassembly 212 and is press fit into cartridge subassembly 210. While torque pin 72 is described as being press fit in to socket 76 and cartridge subassembly 210, other methods of affixing torque pin 72 are contemplated, such as, for example, gluing, welding, etc. Lockout member 60 is disengaged from torque pin 72 leaving torque pin 72 free to rotate with socket 76 and cartridge subassembly 210.

Referring to FIG. 28, as trigger 54 is pivoted farther to rotate gear train 58, socket 76 and thus torque pin 72 begin to rotate. Torque pin 72 rotates approximately 90° through slot 234 on driver subassembly 212 thereby rotating or indexing cartridge subassembly 210 approximately 90°. As noted hereinabove, this aligns the distal end of cartridge subassembly 210 with a proximal face of distal-most fastener 264. At this point, driver subassembly 212 has not yet begun to rotate.

Figure 29:
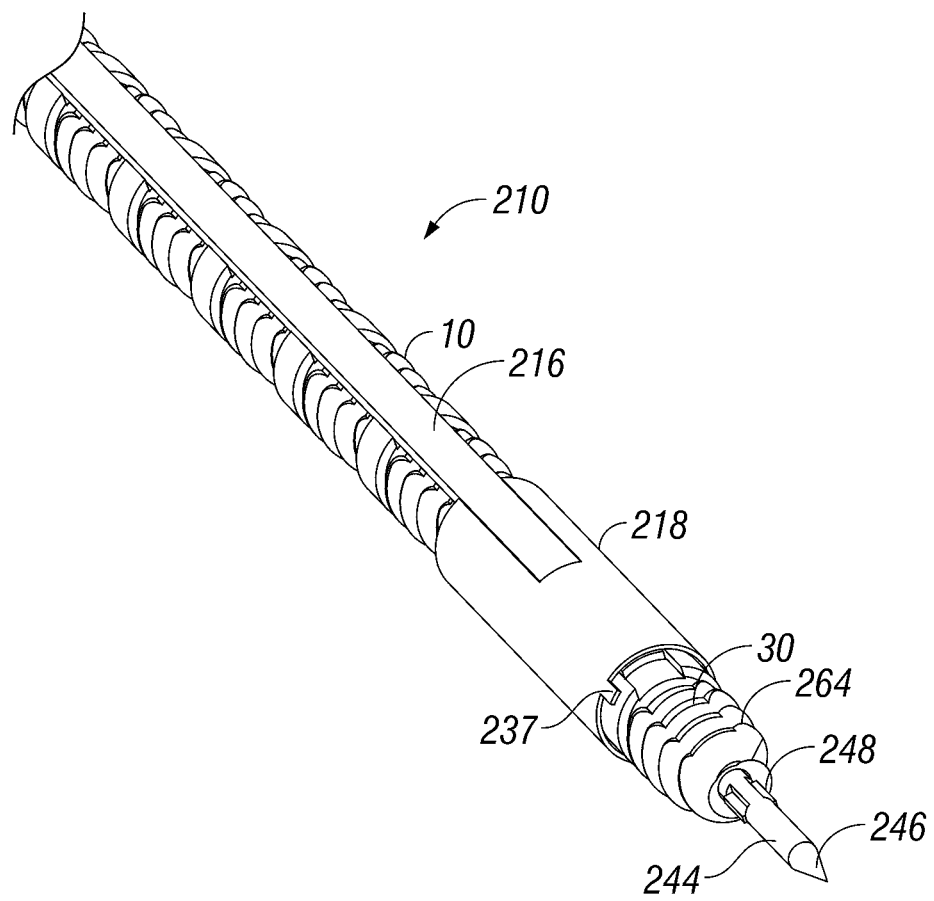
FIG. 29 is a perspective view of the distal end of the cartridge assembly in an initial position.
Figure 30:
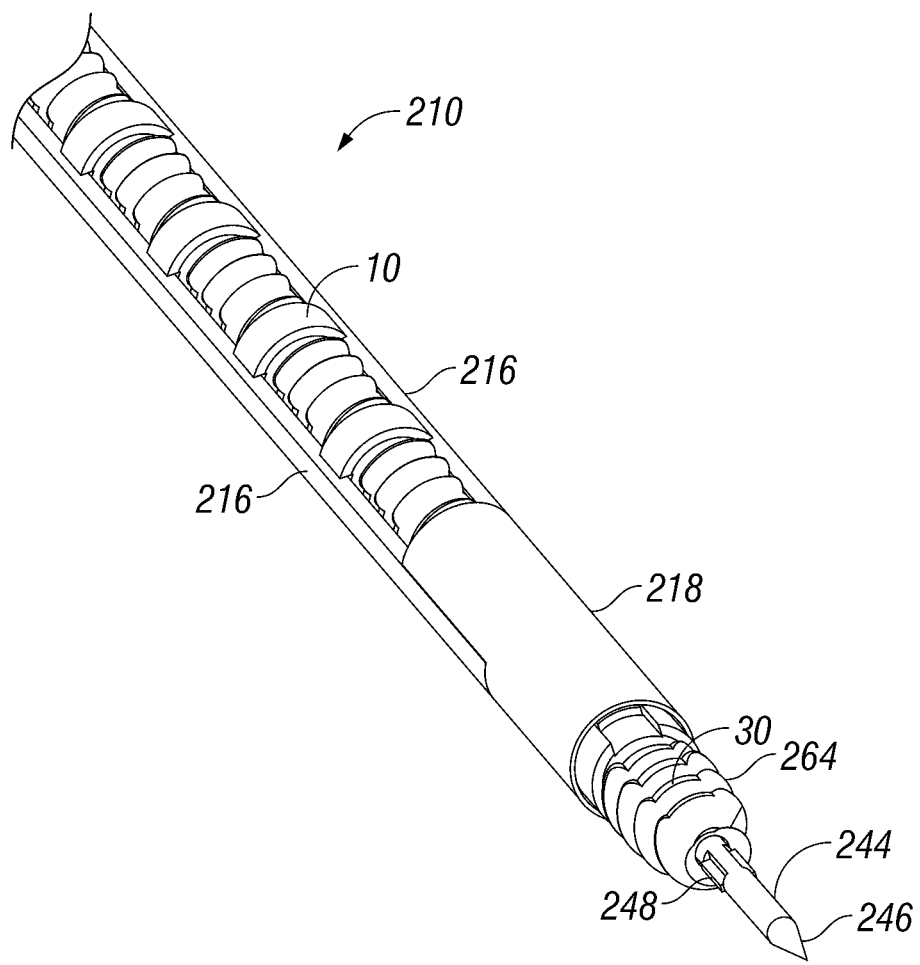
FIG. 30 is a side perspective view of the distal end of the cartridge assembly indexed 90°.
Figure 31:
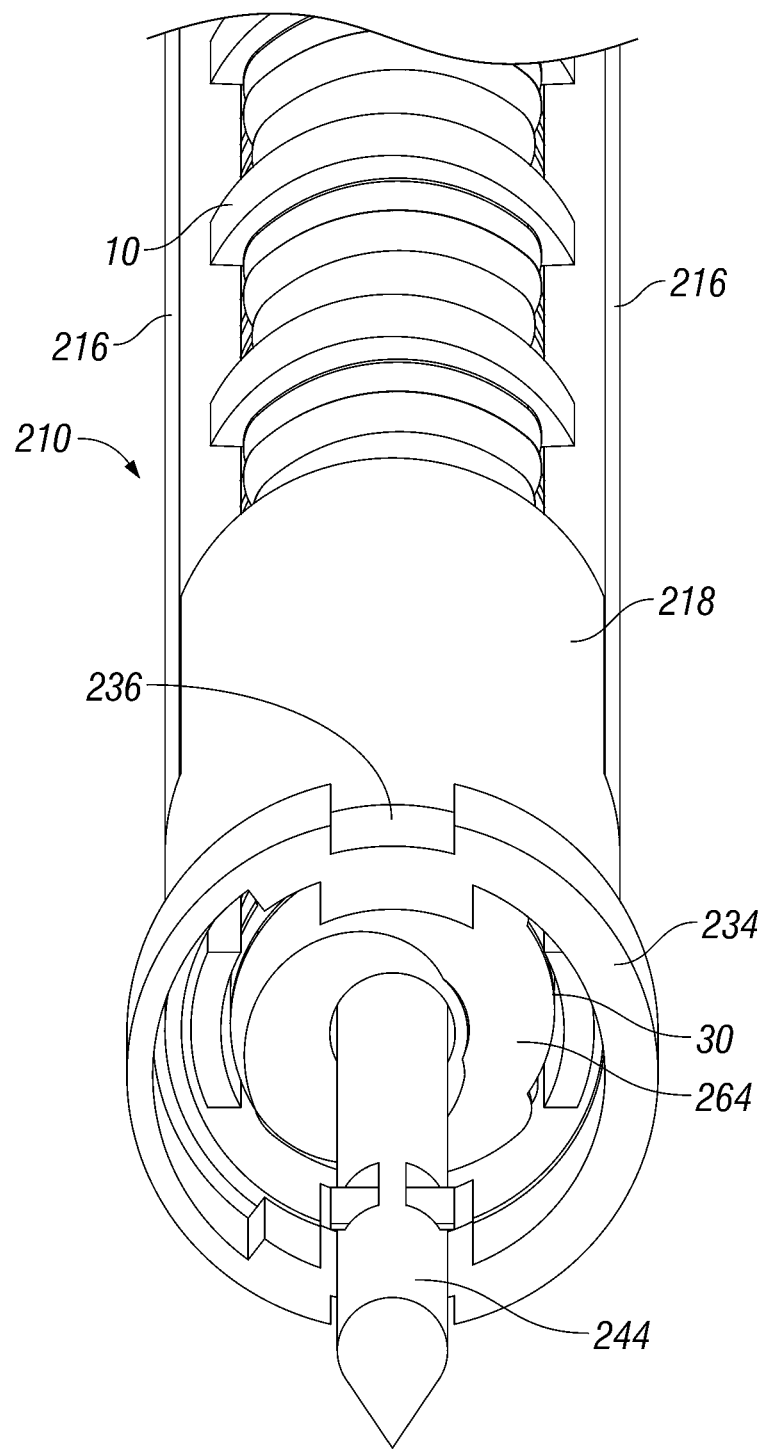
FIG. 31 is a front perspective view of the distal end of the cartridge assembly indexed 90°.

Referring now to FIGS. 29 to 31, the indexing of cartridge subassembly 210 from its initial position to its 90° indexed position is shown with regard to the distal end of cartridge subassembly 210. As shown in FIG. 29, in an initial position, beams 216 are aligned with slots 30 in distal-most fastener 264.

It should be noted that, with regard to subsequent fasteners 10 when beams 216 are in an initial position, beams 216 allow subsequent fasteners 10 to pass into torque ring 234.

Referring now to FIG. 30, cartridge subassembly 210 is shown rotated or indexed approximately 90° moving beams 216 out of alignment with slots 30 in distal-most fastener 264. In this position, stepped down distal ends 226 of beams 216 (not explicitly shown) are in alignment with a proximal face of distal-most fastener 264. Cartridge subassembly 210 is shown in FIG. 31 in its indexed position relative to torque ring 234.

Figure 32:
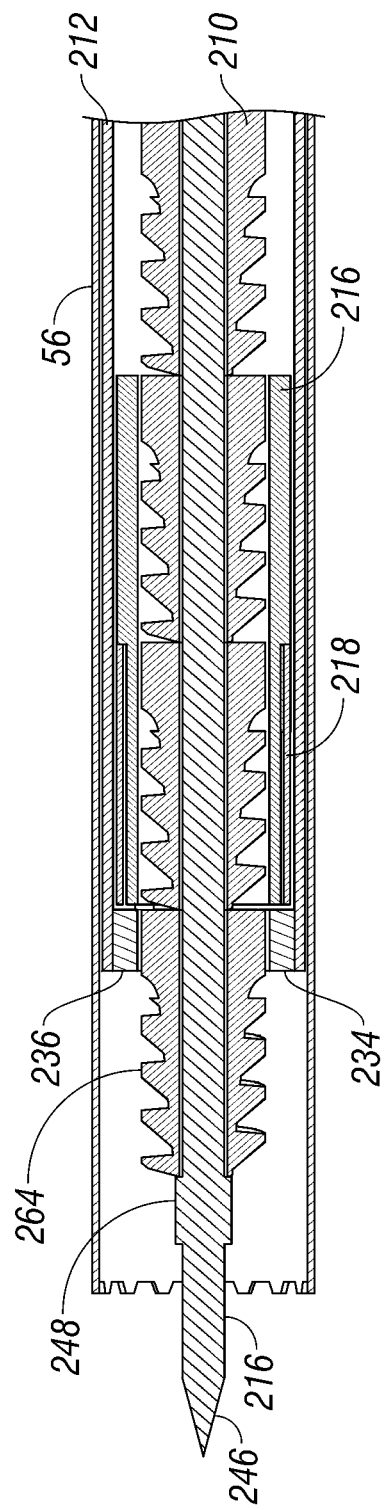
FIG. 32 is a side view, shown in section, of the distal end of the multi-fire surgical instrument during actuation.

Referring now to FIGS. 32 to 37, and initially with regard to FIG. 32, the final movement of trigger 54 to cause needle 216 to pierce mesh and tissue and insert distal-most fastener 264 through the mesh and into tissue is described. As shown in FIG. 32, needle 216 has been extended beyond the distal end of outer tubular member 56 to cause sharp tip 246 of needle 216 to pierce mesh and tissue (not shown). This is accomplished in the manner described hereinabove with regard to FIG. 16. Referring back for the moment to FIG. 16, it was disclosed that as bevel pinion 96 rotates, threads 260 rotate against threads 258 in needle coupling 104 to drive needle coupling 104 distally a distance of approximately 3.5 mm. This extends needle 244 distally through the mesh and into tissue. As noted above with reference to FIG. 16, needle coupling 104, and thus needle 244, can only move distally the length of slot 110 which is restrained by needle pin 108.

Figure 33:
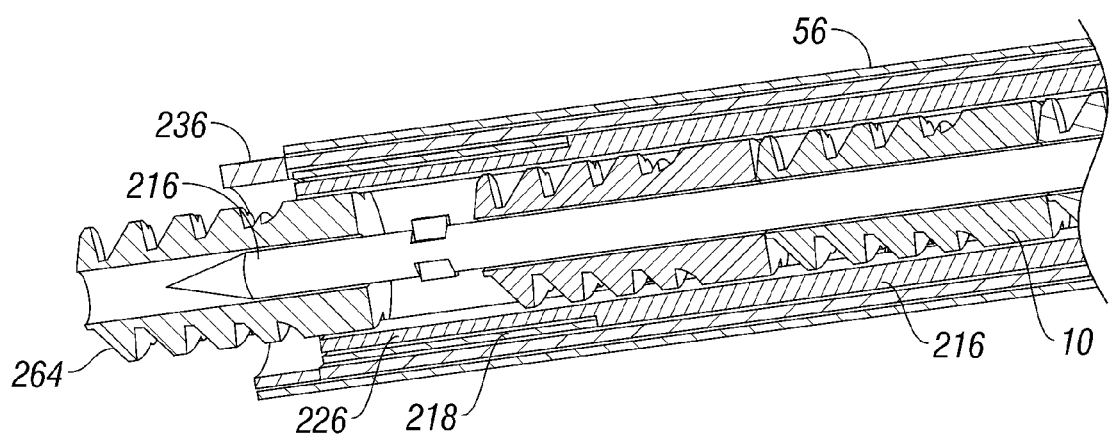
FIG. 33 is a perspective view of the distal end of the multi-fire surgical instrument, shown in section, ejecting a fastener.

Referring now to FIG. 33, distal-most fastener 264 is illustrated being held by torque ring 234 and being driven and rotated into engagement with tissue by torque ring 234 and stepped down distal ends 226 of beams 216. As described in more detail below with reference to FIG. 71, distal-most fastener 264 is advanced over the needle retention feature of needle 244.

Figure 34:
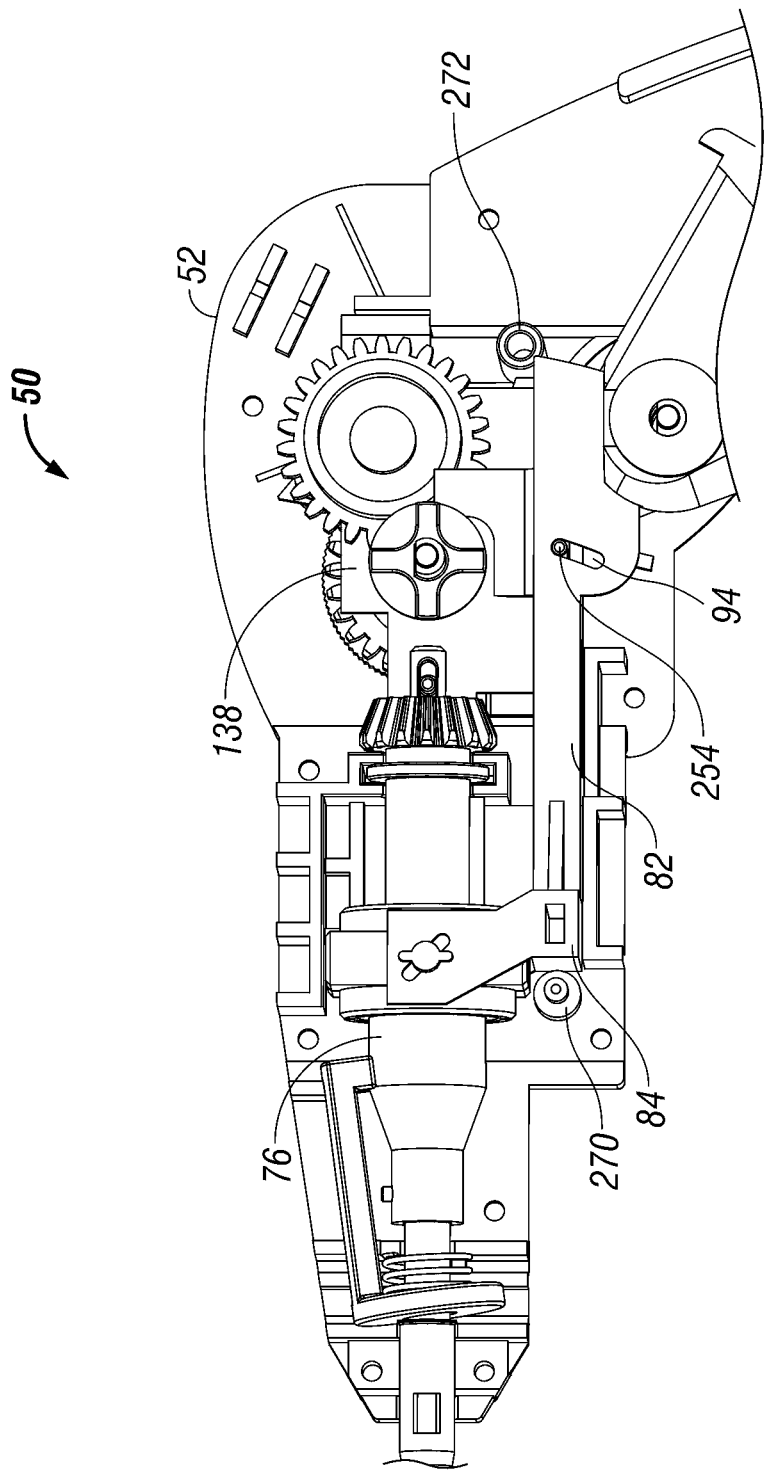
FIG. 34 is a perspective view of the proximal end of the multi-fire surgical instrument during actuation.

In order to prevent unscrewing the distal-most fastener 264 when trigger 54 is released and gear train 58 reverses direction, torque ring 234 must be removed from distal-most fastener 264 before it begins to rotate in the reverse direction. This is accomplished by disengaging clutch 138 from large bevel gear 140. Referring now to FIG. 34, at the very end of the trigger squeeze of trigger 54, link 82 is driven distally such that bracket 84 engages a stop 270 formed on body 52. Rack 146 (not shown) is still being driven distally such that shaft 254 continues to move distally and resides in slot 94. At this point, link 82 has cleared a proximal stop 272 which, up until this point, has restricted link 82 from rotating upwardly.

Figure 35:
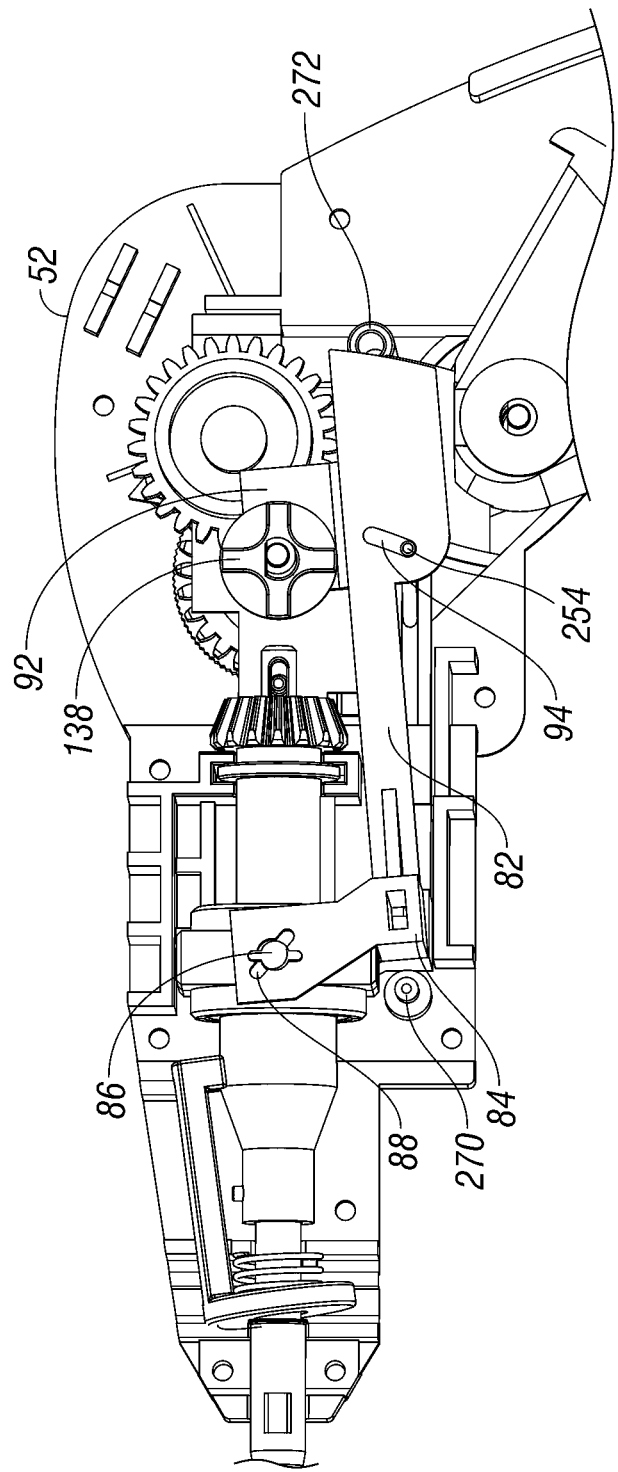
FIG. 35 is a perspective view of the proximal end of the multi-fire surgical instrument with the link rotated to disengage the clutch.

Referring now to FIG. 35, since shaft 254 is still moving distally, and link 82 has engaged stop 270 and cannot travel linearly any farther, link 82 can only pivot upwardly as shaft 254 moves within slot 94. Specifically, bracket 84 pivots about ring pins 86 positioned within bracket slots 88. This motion drives clutch cam 92 up into engagement with clutch 138 to initiate disengagement of clutch 138 with large bevel gear 140 (not shown).

Figure 36:
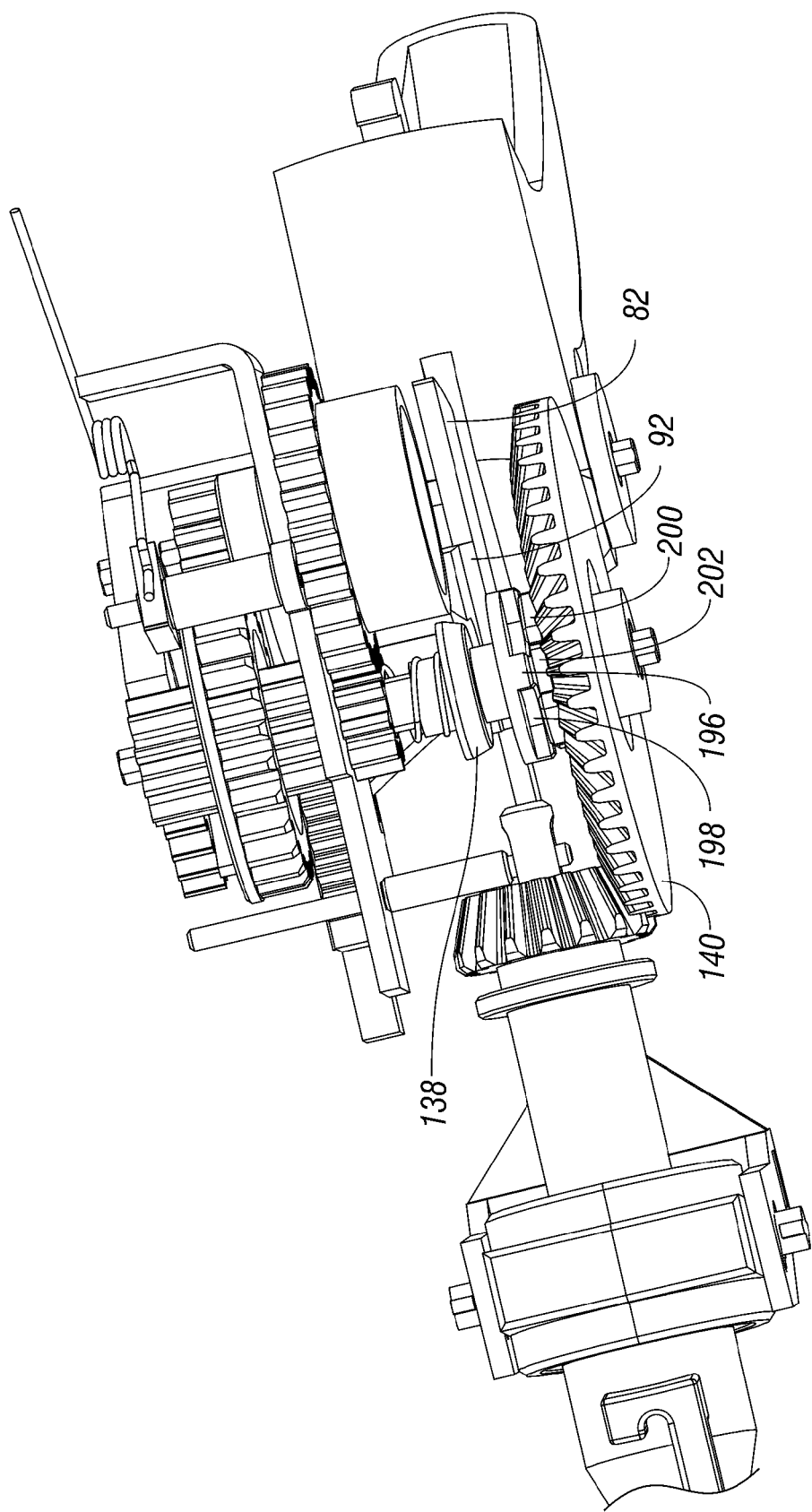
FIG. 36 is a perspective view of the proximal end of the multi-fire surgical instrument illustrating the clutch disengaged from the bevel gear.

As shown in FIG. 36, clutch cam 92 of link 82 cams clutch 138 away from large bevel gear 140 thereby disengaging projections and recesses 196, 198 on clutch 138 from projections and recesses 200, 202 on large double gear 140. Gear train 58 has now been disconnected from large bevel gear at 140 and thus can counter rotate as trigger 54 is released and pawl 124 is reset.

Figure 37:
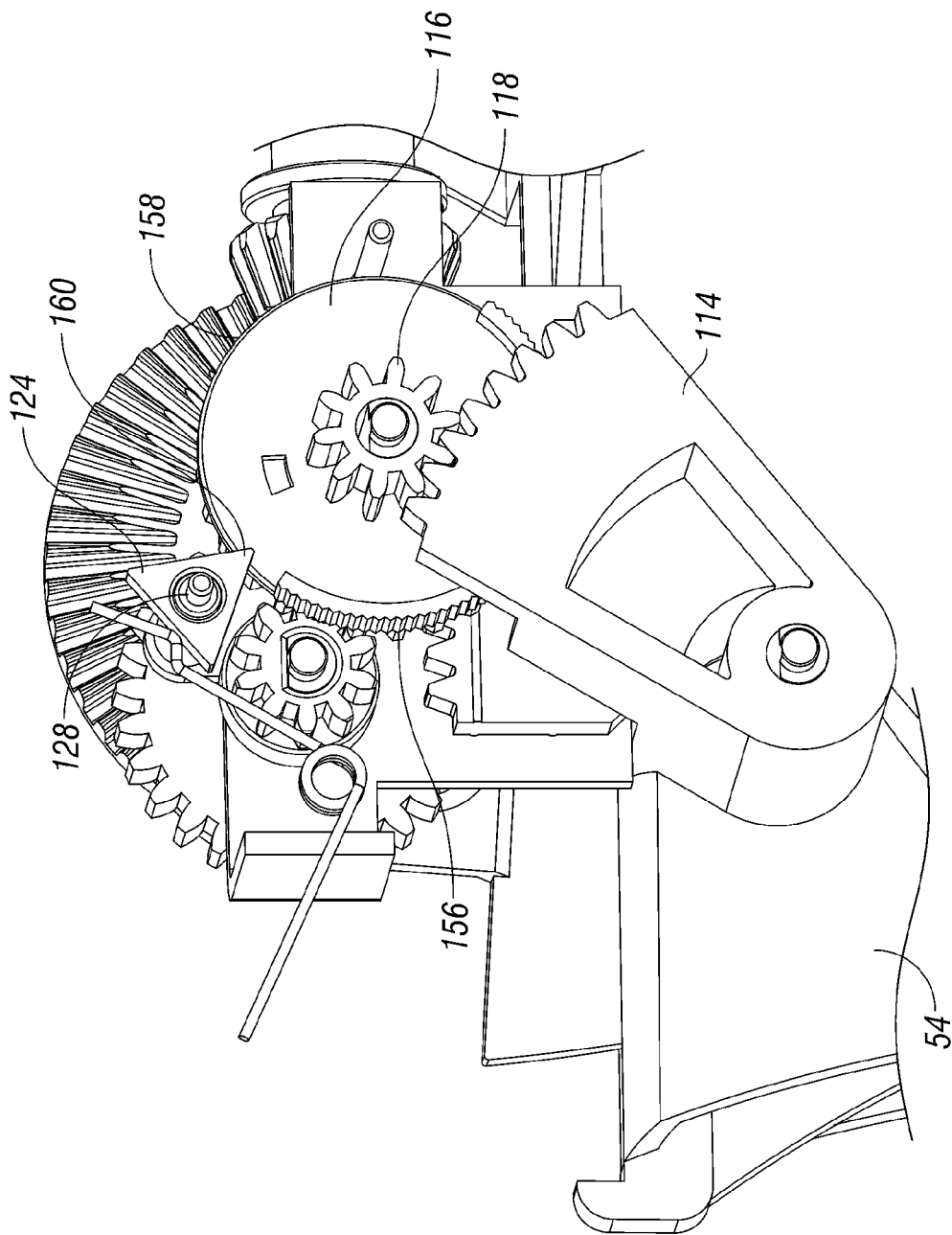
FIG. 37 is a perspective view of the proximal end of the multi-fire surgical instrument at the end of the trigger squeeze sequence.

Referring to FIG. 37, as trigger 54 has reached the limit of its travel, trigger gear 114 rotates spur gear 118, and thus combination gear 116, the full extent of its counterclockwise rotation. At this point, point 160 of pawl 124 has cleared toothed surface 156 of combination gear 116 and resides adjacent smooth surface 158 of combination gear 116. Thus, the ratchet feature of surgical instrument 50 has been disengaged from combination gear 116. Upon release of trigger 54 against the bias of trigger spring (not shown in this embodiment), pawl 124 can pivot about pin 128 such that point 160 drags back over toothed surface 156 to the initial pre-fired position.

The release of trigger 54 to reset gear train 58, link 82, needle coupling 104 and cartridge and driver subassemblies 210 and 212, respectively, is described. While the reversal procedure is not specifically shown, reference is made to FIGS. 16 and 35 for illustration of the various components. As trigger 54 is released, trigger 54 moves back to its original position. This reverses gear train 58 such that rack 146 is now pulling link 82 in a proximal direction. Clutch cam 92 on link 82 remains engaged with clutch 138 until rack 146 has moved proximally sufficient enough for shaft 254 to travel upwardly within slot 94 and link 82 to disengage clutch cam 92 from clutch 138. The distance rack 146 moves proximally is approximately equal to the distance torque ring 234 moves proximally to disengage from distal-most fastener 264, thereby leaving distal-most fastener 264 threaded through the mesh and into tissue.

Once clutch cam 92 has been disengaged from clutch 138, clutch 138 reengages large bevel gear 142 to affect counter rotation of the cartridge and driver subassemblies 210, 212. Socket 76 is drawn proximally by the proximal movement of link 82 which is affixed to rings 74 attached to socket 76. Socket 76 contacts needle coupling 104 and compresses needle coupling spring 106 such that the left-hand thread 258 on needle coupling 104 reengages left-hand thread 260 in bevel pinion 96. Needle 244 is thus drawn proximally to its initial position by the proximal movement of needle coupling 104.

Figure 38:
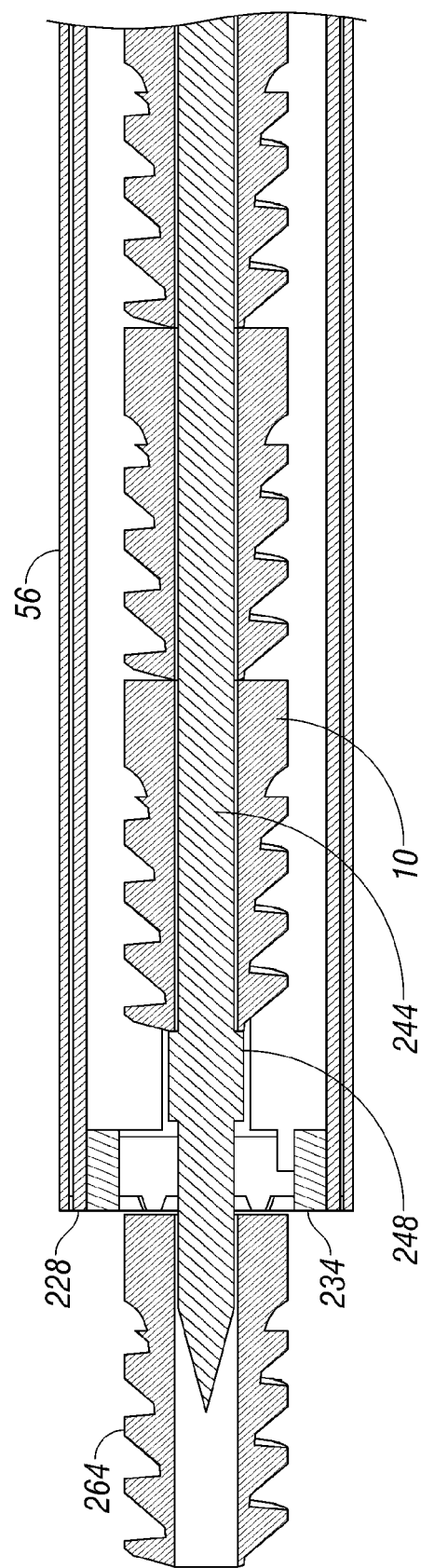
FIG. 38 is a side view, shown in section, of the distal end of the multi-fire surgical instrument immediately prior to the cartridge assembly being retracted.

Referring now to FIGS. 38 to 41, the corresponding effect of the resetting of surgical instrument 50 on the distal end components of surgical instrument 50 is described. Referring initially to FIG. 38, distal-most fastener 264 has been installed in tissue and needle 244 has not yet retracted. New fastener 10 is adjacent needle retention member 248 on needle 244. Needle 244 is still in the extended position corresponding to needle coupling 104 being in its distal-most position. In this position, cartridge subassembly 210 is still rotated approximately 90° such that beams 216 are out of alignment with slots 236 in torque ring 234.

Figure 39:
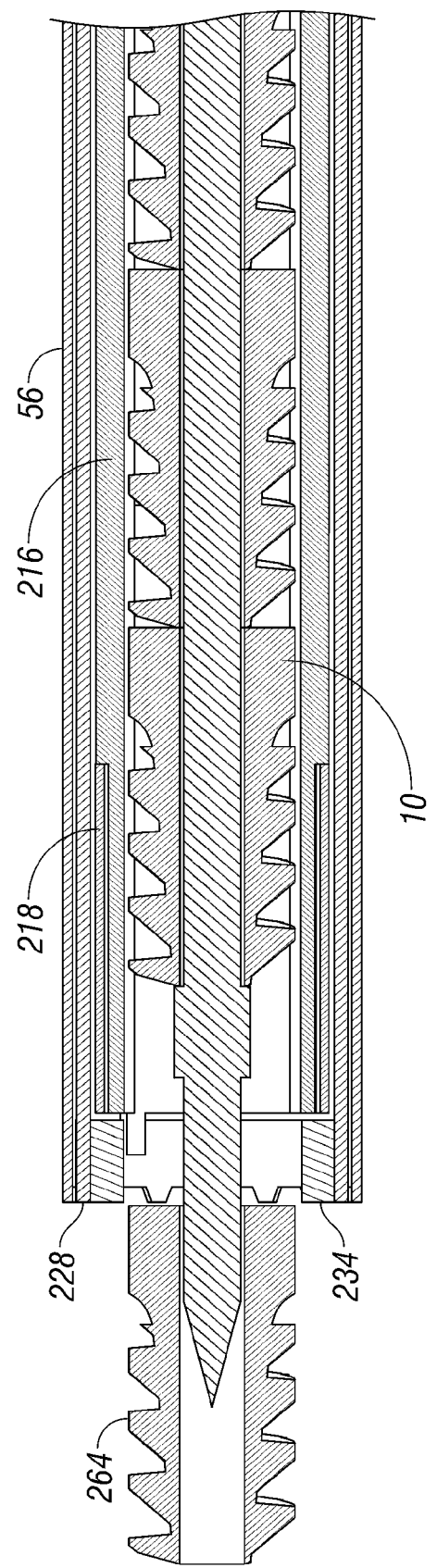
FIG. 39 is a side view, shown in section, of the distal end of the multi-file surgical instrument reindexed 90°.

Referring now to FIG. 39, cartridge beams 216 have been rotated back approximately 90° such that cartridge beams 216 are now in alignment with slots 236 in torque ring 234 so as to allow a new fastener 10 to be positioned within torque ring 234.

Figure 40:
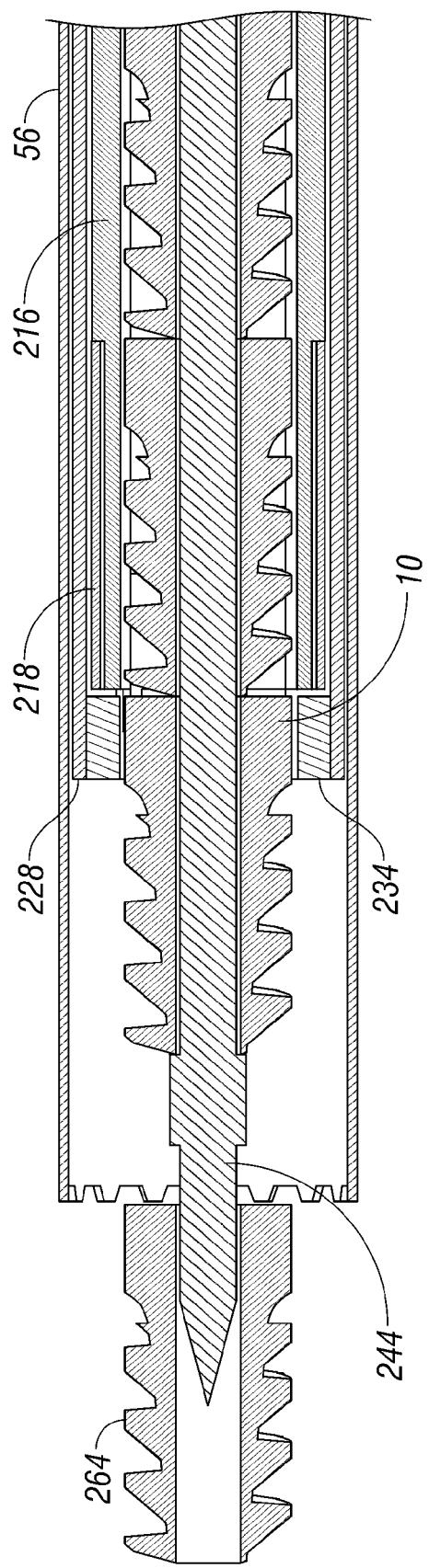
FIG. 40 is a side view, shown in section, of the distal end of the surgical instrument with the cartridge assembly retracted.

Referring now to FIG. 40, driver and cartridge sub assemblies 210 and 212, respectively, have been withdrawn proximally to their retracted position by gear train 58 (shown about 3.5 mm into the firing stroke), needle 244 is still in the extended position but will retract once needle coupling 104 moves proximally rethreading itself within bevel pinion 96.

Figure 41:
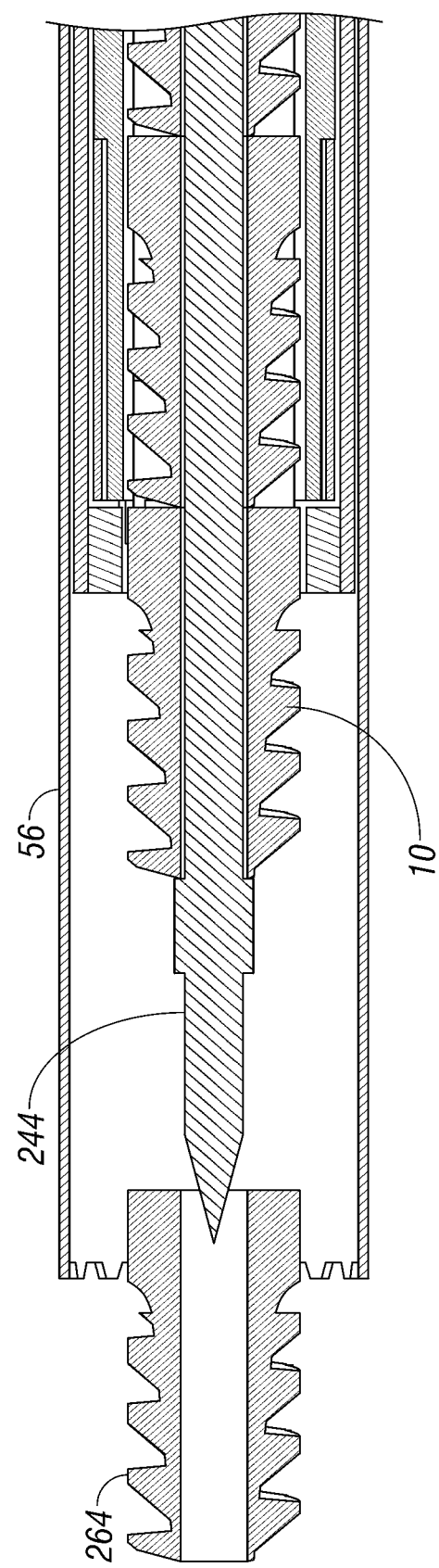
FIG. 41 is a side view, shown in section, of the distal end of the multi-fire surgical instrument with the outer tubular member re-extended.

As shown in FIG. 41, needle 244 is in a proximal initial position and a new fastener 10 is in position to be advanced over needle retention feature 248 on needle 244. At this point surgical instrument 50 is in a condition to be refired to thereby insert the next fastener 10 through mesh and into tissue.

Figure 42:
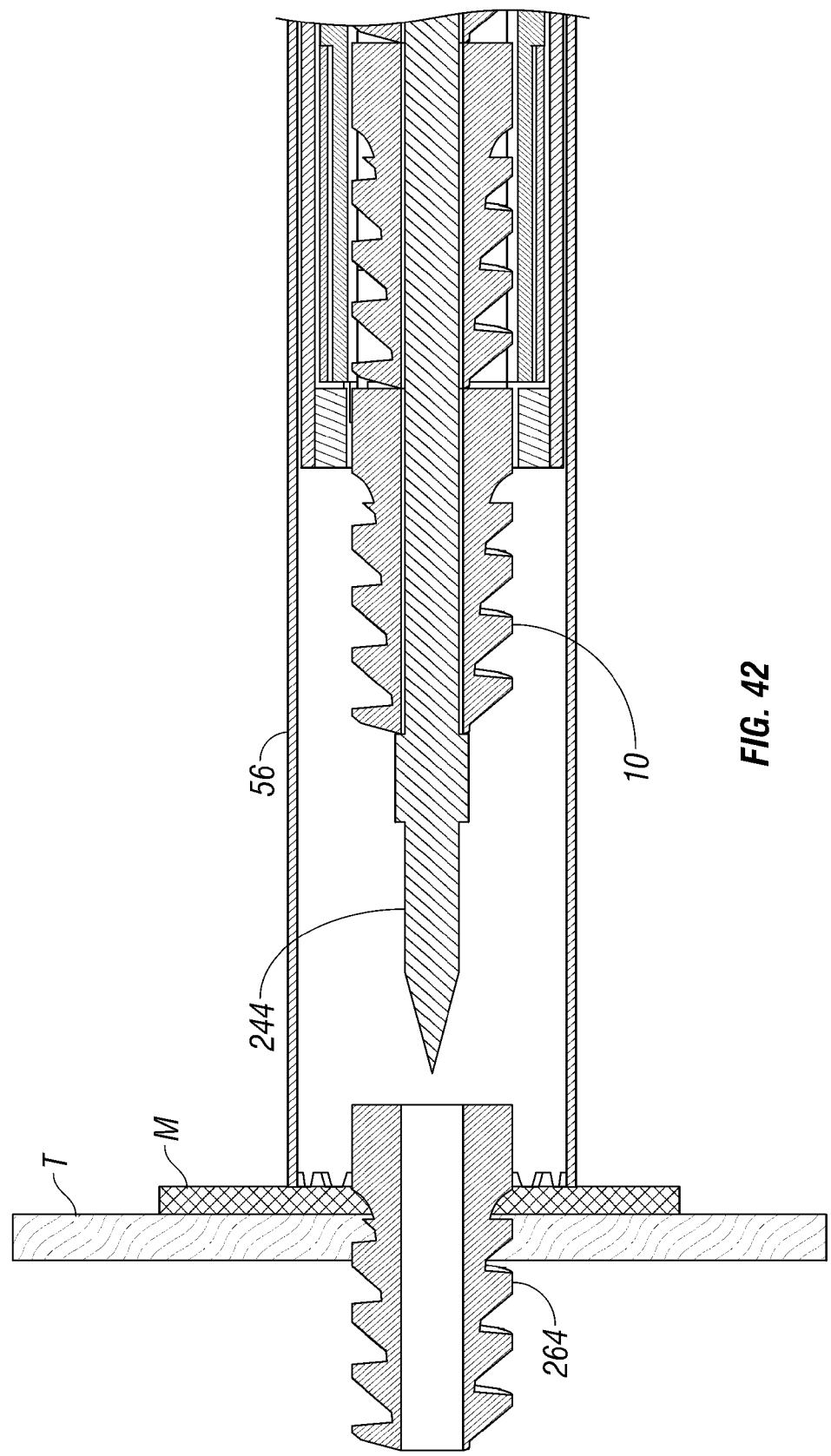
FIG. 42 is a perspective view, shown in section, of the distal end of the multi-fire surgical instrument after actuation and release of the trigger.

Referring now to FIG. 42, distal-most fastener 264 is shown inserted through mesh M and into tissue T. Surgical instrument 50 has been pulled away from the tissue T such that outer tubular member 56 moves to its distal-most position since the approximate 2 pounds of pressure against mesh M and tissue T has been relieved. Additionally, the movement of outer tubular member 56 to its distal-most position assists in pushing distal-most fastener 264 out of surgical instrument 50. Thus, the firing cycle has been completed.

Figure 43:
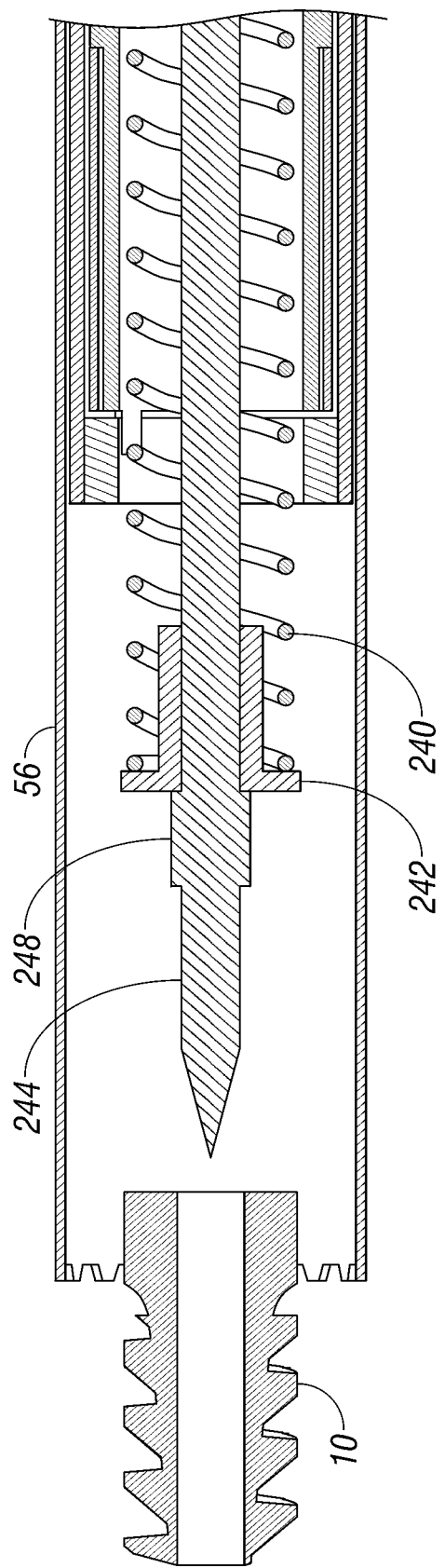
FIG. 43 is a side view, shown in section, of the distal end of the multi-fire surgical instrument after the last fastener has been ejected.

Referring to FIG. 43, the distal end of surgical instrument 50 is shown with the last fastener 10 ejected from surgical instrument 50. Pusher 242 is biased against needle retention feature 248 due to the bias of spring 240 and traps spring 240 within outer tubular member 56.

Figure 44:
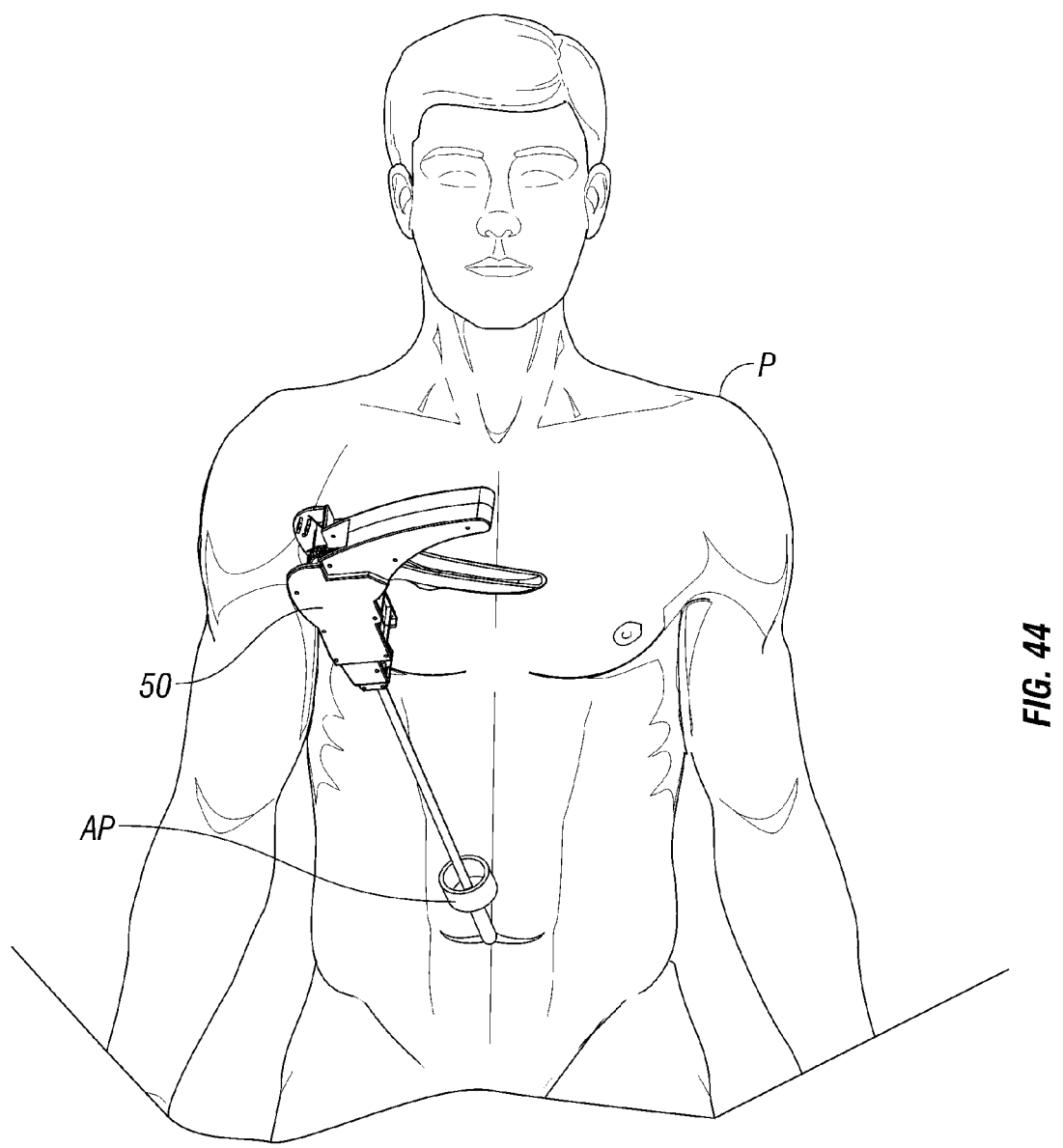
FIG. 44 is a perspective view of the multi-fire surgical instrument inserted through an access port in a patient.
Figure 45:
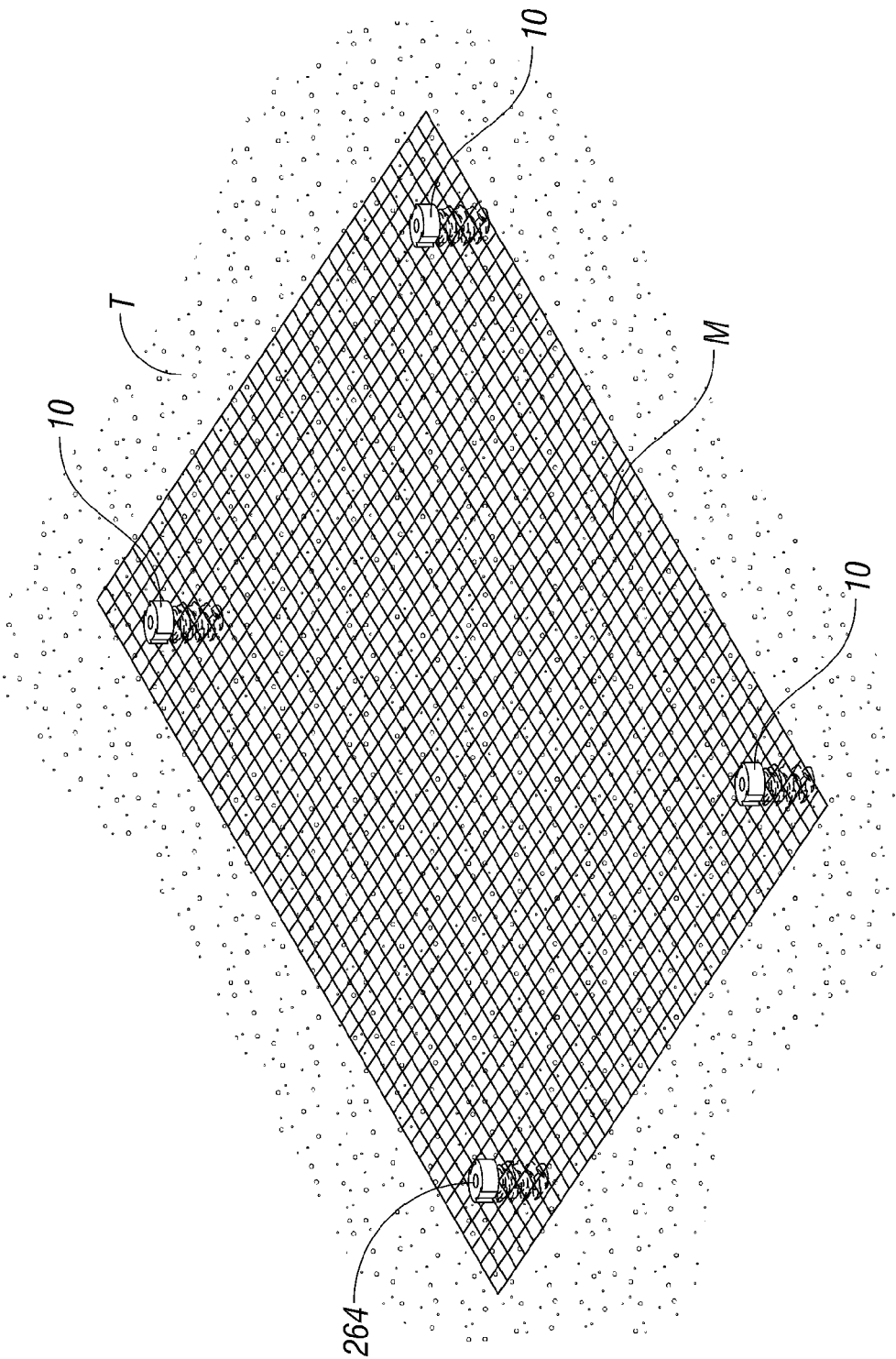
FIG. 45 is a perspective view of a surgical mesh secured to tissue by the disclosed absorbable screw fastener.
Figure 46:
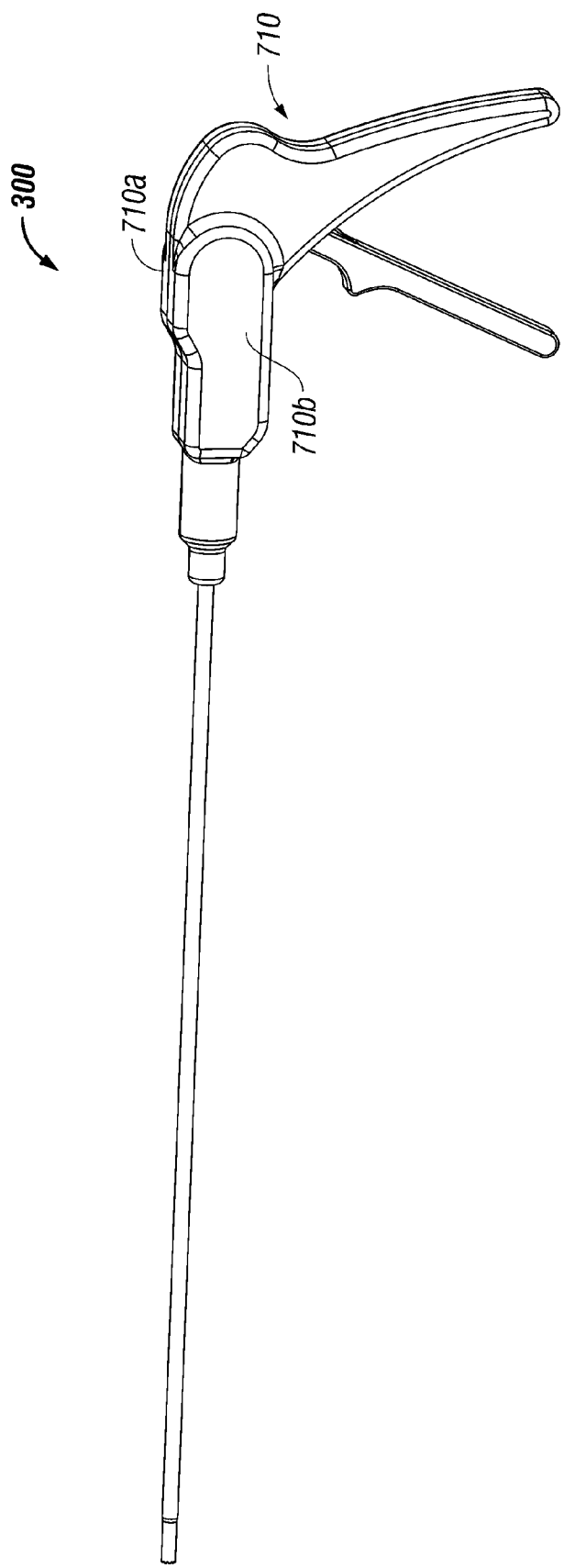
FIG. 46 is a perspective view of another embodiment of a multi-fire surgical instrument.

As shown in FIG. 44, during use, surgical instrument 50 is inserted through an access port AP in a patient P to perform the laparoscopic or endoscopic procedure. FIG. 45 illustrates surgical mesh M affixed to tissue T by distal-most fastener 264 and subsequently-installed fasteners 10.

Now referring to FIGS. 46-76, another embodiment of a multi-fire surgical instrument 300 for installing fasteners 10 into tissue is shown. Surgical instrument 300 includes a shaft assembly 310 (see generally FIG. 47) and a handle assembly 700 (see generally FIG. 56). Shaft assembly 310 includes first sub-assembly 320 (FIG. 47) having an introducer or needle 330, a pusher 340 and a feed spring 360; a second sub-assembly 400 (FIGS. 47-53) having a coupling 410, an inner tube 430, bands 450, a socket 470, a torque pin 490 and a needle pin 494; a third sub-assembly 500 (FIG. 53) having first and second ring halves 510a, 510b that form ring 510; a fourth sub-assembly 550 (FIG. 54) having a rack 560; and a fifth sub-assembly 600 (FIG. 55) having a needle plate 610, a lockout 620, an outer tube 640 and a small bevel gear 660. Handle assembly 700 includes a housing 710, a movable handle 720, a fixed handle 722, a large bevel gear 730, a pawl 740, a clutch 750, a planetary gear 760, a planetary ring plate 770, a tooth gear 780, a planetary sun 780 and a spur gear 800.

Figure 75:
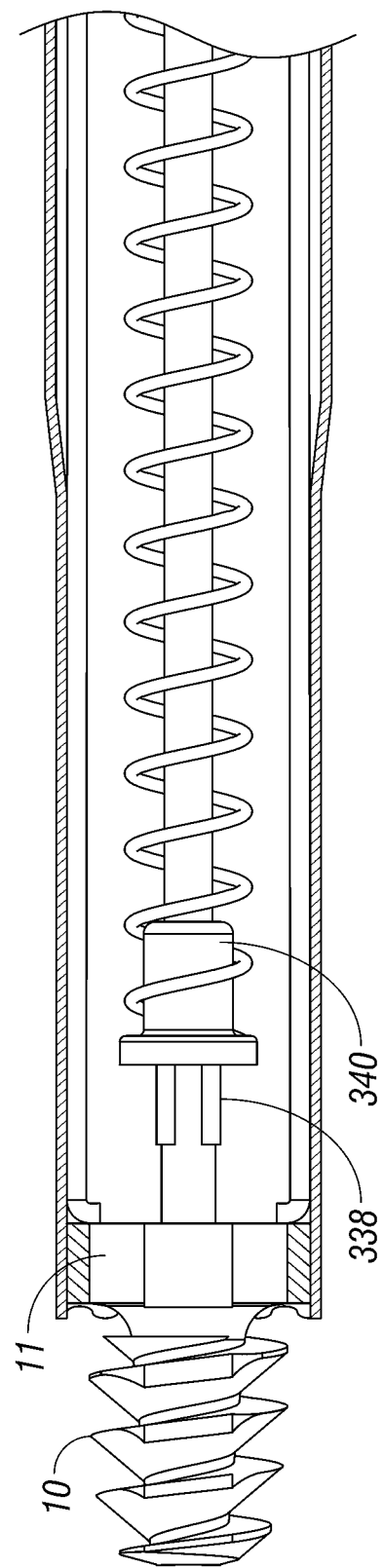
FIG. 75 is a partial cross-sectional view of the distal end of the multi-fire surgical instrument of FIGS. 46-74 illustrating the final fastener within the inner tube being fired.

The interconnection of the various parts of surgical instrument 300 is discussed with reference to FIGS. 47-64. Initially, the description of shaft assembly 310 and more specifically first sub-assembly 320 is discussed with reference to FIG. 47. Needle 330 includes a proximal end 332, a distal end 334, a bend 336 adjacent proximal end 332 and a needle retention feature 338 (FIG. 65) near distal end 334. Needle 330 may be tapered at distal end 334. A plurality of fasteners 10 is illustrated on needle 330. Pusher 340 (a larger view of pusher 340 is shown in FIG. 75) is located around needle 330 (needle 330 is inserted through a hole of pusher 340) at a location that is proximal to fasteners 10. Feed spring 360 is radially disposed around needle 330 and distal portion 362 of feed spring 360 is in mechanical cooperation with pusher 340. Further, feed spring 360 is disposed between pusher 340 and bend 336. Feed spring 360 distally biases pusher 340 towards distal end 334 of needle 330. Initially, needle retention feature 338 withstands the distal force exerted by feed spring 360, thus maintaining fasteners 10 on needle 330.

Figure 47:
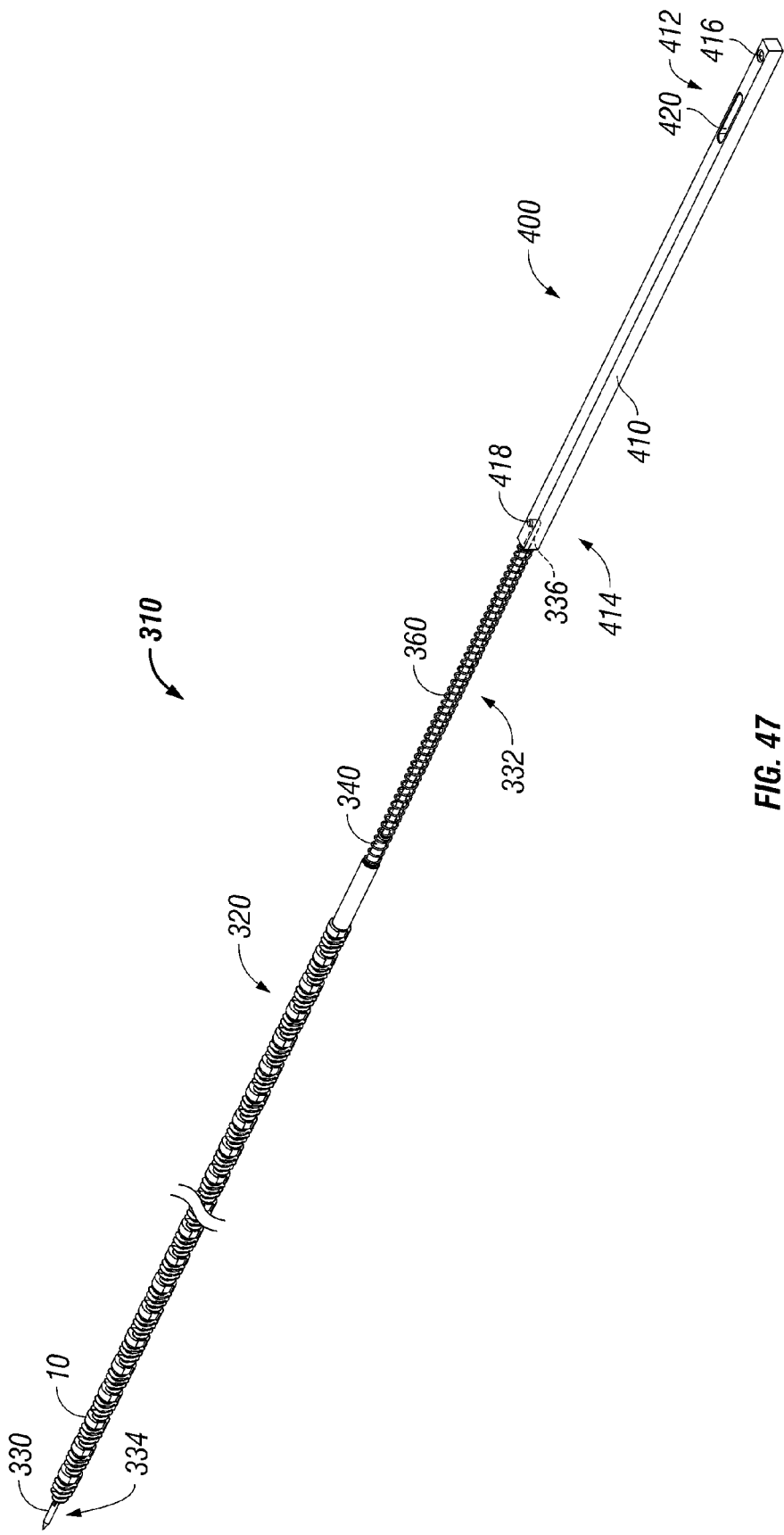
FIG. 47 is a perspective view of a needle, fasteners, spring and coupling of the multi-fire surgical instrument of FIG. 46.
Figure 48:
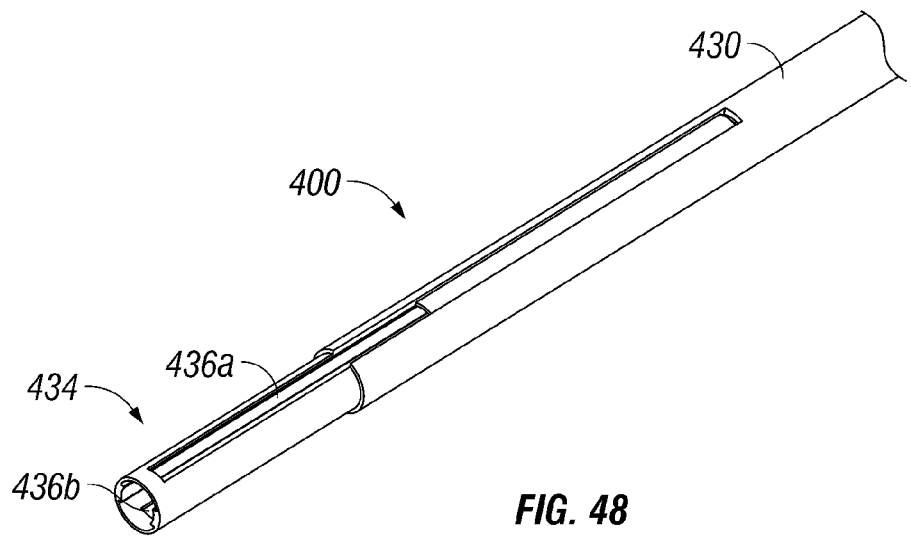
FIG. 48 is a perspective view of the distal end of an inner tube of the multi-fire surgical instrument of FIGS. 46 and 47.
Figure 49:
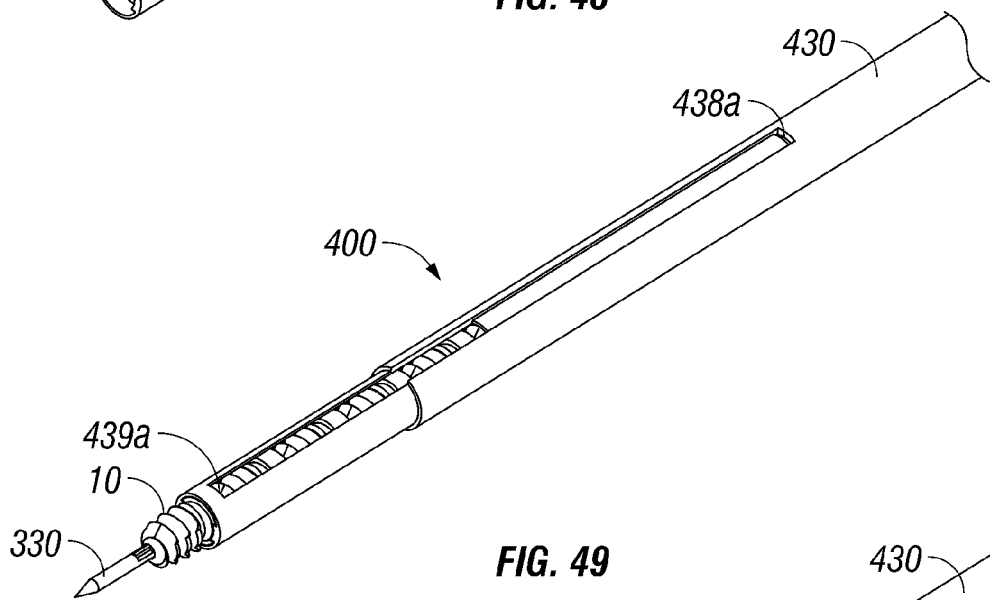
FIG. 49 is a perspective view of the distal end of the inner tube illustrated in FIG. 48 further including the needle and fasteners therein.

With reference to FIGS. 47-53, second sub-assembly 400 is illustrated. Coupling 410 of second sub-assembly 400 is illustrated in FIG. 47. Coupling 410 includes a proximal portion 412, a distal portion 414, a proximal hole 416, a distal hole 418 and a slot 420. Distal hole 418 receives bend 336 of needle 330. Proximal hole 416 and slot 420 receive needle pin 494 and torque pin 490, respectively, as is discussed in more detail below.

Figure 50:
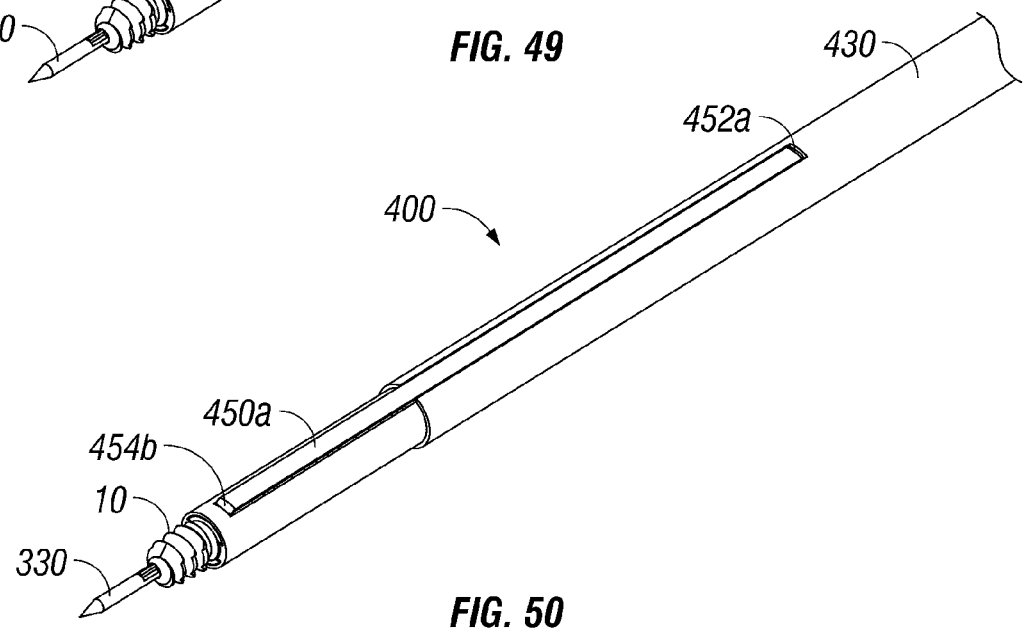
FIG. 50 is a perspective view of the distal end of the inner tube illustrated in FIG. 49 further including bands disposed on the inner tube.
Figure 51:
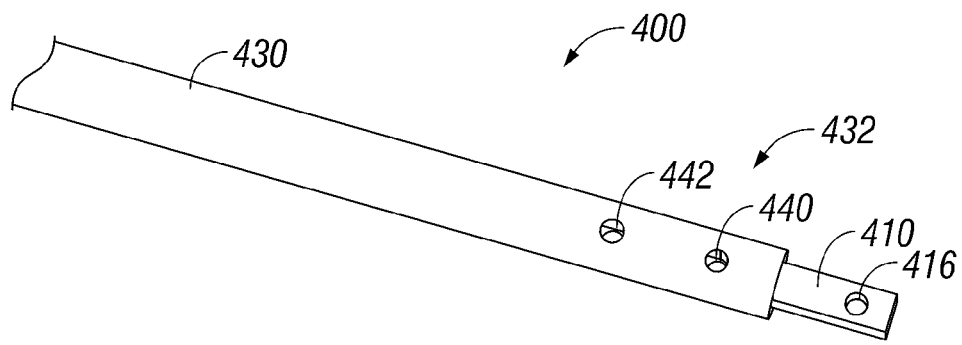
FIG. 51 is a perspective view of the proximal end of the inner tube and the coupling of the multi-fire surgical instrument of FIGS. 46-51.

Elongate tubular member or inner tube 430 is illustrated in FIGS. 48-52. Inner tube 430 includes a proximal portion 432 (FIG. 51), a distal portion 434 (FIG. 48), a pair of grooves 436a, 436b (FIG. 48), a pair of proximal slots 438a, 438b (proximal slot 438a shown in FIG. 49), a pair of distal slots 439a, 439b (distal slot 439a shown in FIG. 49), a pin hole 440 (FIG. 51) disposed near proximal portion 432 and an alignment hole 442 (FIG. 51) disposed distally of pin hole 440. Inner tube 430 at least partially surrounds needle 330 and fasteners 10 (see FIGS. 49 and 50) as well as pusher 340 (FIG. 75), feed spring 360 (FIG. 75) and coupling 410 (FIG. 51). As illustrated in FIG. 50, a pair of bands 450a, 450b (only one band 450a being shown) is inserted on inner tube 430. Specifically, a proximal face 452a of band 450a is inserted into proximal slot 438a of inner tube 430, while proximal face 452b of band 450b is inserted into proximal slot 438b (not shown). Similarly, a distal face 454a of band 450a is inserted into a distal slot 439a of inner tube 430 and a distal face 454b of band 450b is inserted into a distal slot 439b of band 450b (not shown). Bands 450a, 450b rest in grooves 436a, 436b, respectively, of inner tube 430. It is envisioned that at least one band 450a or 450b is disposed of an elastic material such that band 450a and/or 450b is flexible.

Figure 52:
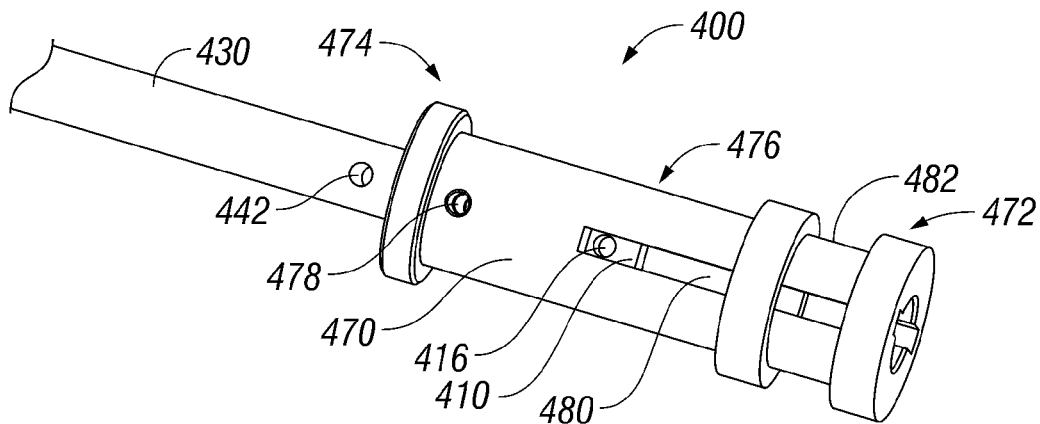
FIG. 52 is a perspective view of the multi-fire surgical instrument of FIG. 51 further including a socket.

Socket 470 is best illustrated in FIG. 52. Socket 470 includes a proximal portion 472, a distal portion 474, an intermediate portion 476, a distal hole 478, a slot 480 and a groove 482. Distal portion 474 of socket 470 is configured to be linked to proximal portion 412 of coupling 410 and to proximal portion 432 of inner tube 430 (see also FIG. 51). Distal hole 478 of socket 470 aligns with pin hole 440 of inner tube 430. A torque pin 490 is insertable through both distal hole 478 and pin hole 440 (see FIGS. 53 and 54). Slot 480 of socket 470 extends through socket 470. A portion of slot 480 is positioned to align with proximal hole 416 of coupling 410. A needle pin 494 is insertable through both slot 480 and proximal hole 416 of coupling 410 (see FIGS. 53-55). This arrangement allows for relative movement between socket 470 and coupling 410. Additionally, alignment hole 442 in inner tube 430 facilitates proper alignment between socket 470 and inner tube 430.

Figure 53:
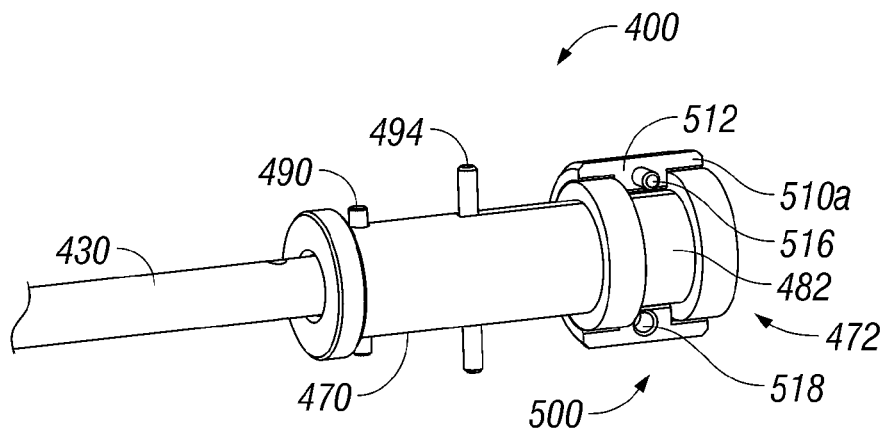
FIG. 53 is a perspective view of the multi-fire surgical instrument of FIG. 52 further including a needle pin, a torque pin and a ring half.

With reference to FIG. 53, third sub-assembly 500 is illustrated, including ring 510. Ring 510 is comprised of two ring halves 510a, 510b (only ring half 510a is illustrated in FIG. 53) which are dimensioned to fit together (either by snapping, welding, or the like) over proximal portion 472 of socket 470. Specifically, a protrusion 512 of each of ring halves 510a and 510b fits into groove 482 of socket 470. Further, each ring half 510a and 510b may include a boss 516 and an aperture 518 (FIG. 53), boss 516 being appropriately sized to fit within aperture 518 to lock each ring half 510a, 510b together. Additionally, each ring half 510a, 510b includes an attachment structure 514 (FIG. 54) for connection with rack 560, as described below. Ring 510 and socket 470 are situated such that socket 470 is rotatable with respect to ring 510.

Figure 54:
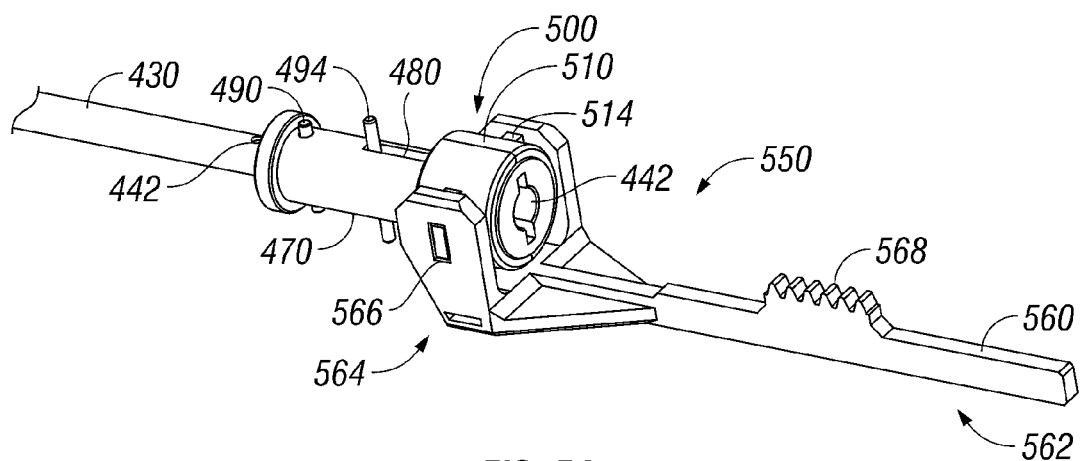
FIG. 54 is a perspective view of the multi-fire surgical instrument of FIG. 53 further including a second ring half and a rack.

Fourth sub-assembly 550 is illustrated in FIG. 54 and includes a rack 560. Rack 560 includes a proximal portion 562, a distal portion 564, a pair of openings 566 and a plurality of teeth 568. Pair of openings 566 are mechanically engagable with attachment structure 514 of ring halves 510a, 510b. Thus, distal movement of rack 560 translates ring 510, socket 470, inner tube 430, bands 450a, 450b and thus distal-most fastener 264 longitudinally, as described in more detail below. Rack 560, ring 510 and socket 470 are disposed at least partially within housing 710 and are collectively referred to as actuation assembly.

Figure 55:
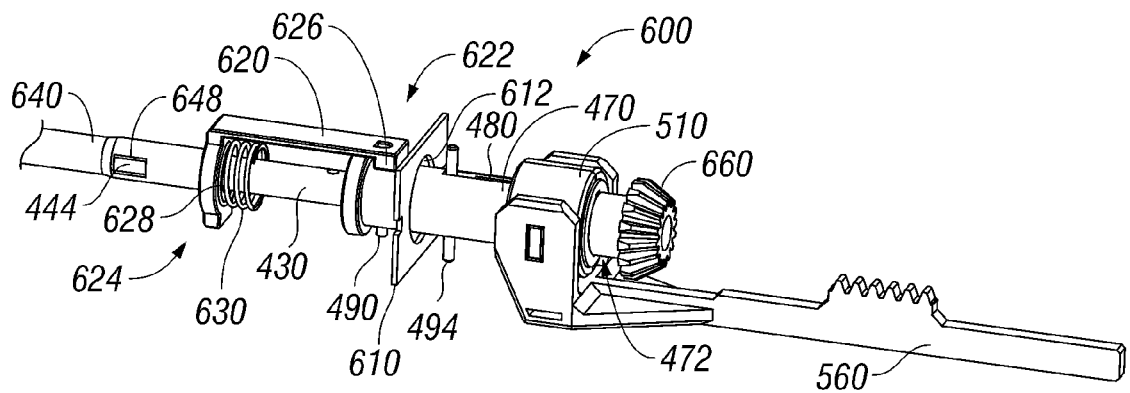
FIG. 55 is a perspective view of the multi-fire surgical instrument of FIG. 54 further including an outer tube, a lockout, a needle plate and a small bevel gear.

With reference to FIG. 55, fifth sub-assembly 600 is illustrated. Needle plate 610 of fifth sub-assembly 600 includes an opening 612 therein. Opening 612 is appropriately sized to enable needle plate 610 to fit around socket 470. Needle plate 610 is positioned around socket 470 such that socket 470 is capable of longitudinal and/or rotational movement with respect to needle plate 610. As seen in FIG. 55, needle pin 494 has a larger length than the diameter of opening 612 in needle plate 610, thus limiting distal translation of needle pin 494. A second housing rib 674 (FIG. 68) restricts distal movement of needle plate 610.

With continued reference to FIG. 55, lockout 620 of fifth sub-assembly 600 includes a proximal portion 622 and a distal portion 624. A slot (not explicitly shown) is disposed at least partially through lockout 620 adjacent proximal portion 622 and is configured to allow a portion of torque pin 490 to longitudinally travel therethrough. An opening 628 is disposed through distal portion 624 to allow inner tube 430 to pass therethrough. Lockout spring 630 is disposed adjacent distal portion 624 of lockout 620, extending towards proximal portion 622. Lockout spring 630 is bounded at its proximal portion by a first housing rib 672 within housing 670 (see FIG. 67).

With continued reference to FIG. 55, outer tube 640 is disposed distally of lockout 620 and around inner tube 430. A slot 648 disposed adjacent a proximal portion 632 of outer tube 640 engages a pin 444 of inner tube 430. This relationship allows for longitudinal translation of outer tube 640 with respect to inner tube 430 and prevents rotational movement of outer tube 640 with respect to inner tube 430.

Figure 58:
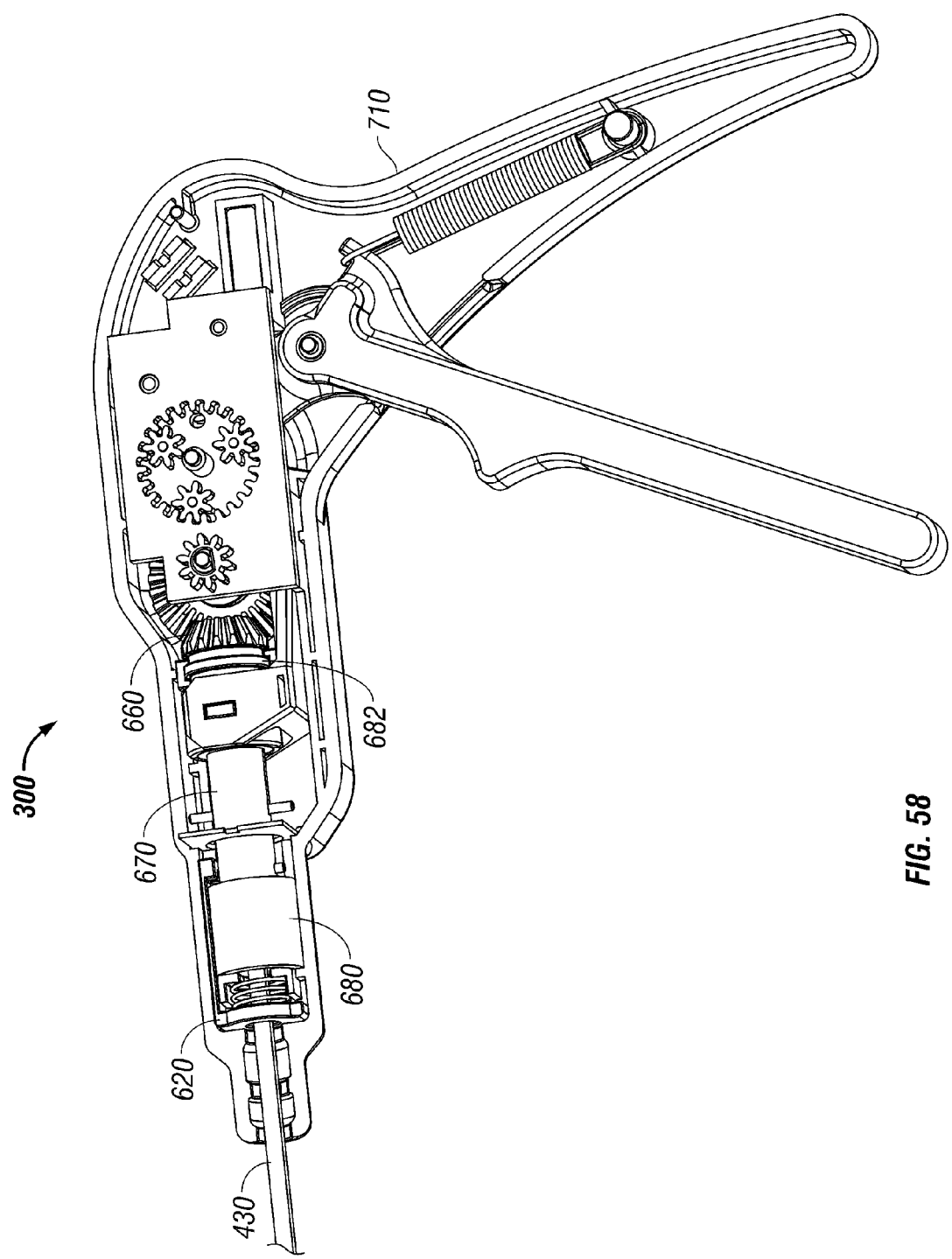
FIG. 58 is a perspective view of the multi-fire surgical instrument of FIG. 57 further including a first bushing and a second bushing.

With reference to FIG. 58, a first bushing 680 and a second bushing 682 are shown in accordance with an embodiment of the present disclosure. First bushing 680 is a hollow cylindrical member disposed around distal portion 474 of socket 470 (illustrated in a non-actuated position. First bushing 680 prevents body portions 710a, 710b (FIG. 46) of housing 710 from frictionally interfering with the rotation and/or longitudinal movement of socket 470, lockout 620 and/or inner tube 430. Similarly, second bushing 682 is a hollow cylindrical member disposed around a portion of small bevel gear 660 and prevents body portions 710a, 710b of housing 710 from frictionally interfering with rotational movement of small bevel gear 660. It is envisioned that at least one of first bushing 680 and second bushing 682 includes a lubricant thereon (external surface and/or internal surface) to minimize any undesired forces or frictional effects.

Figure 65:
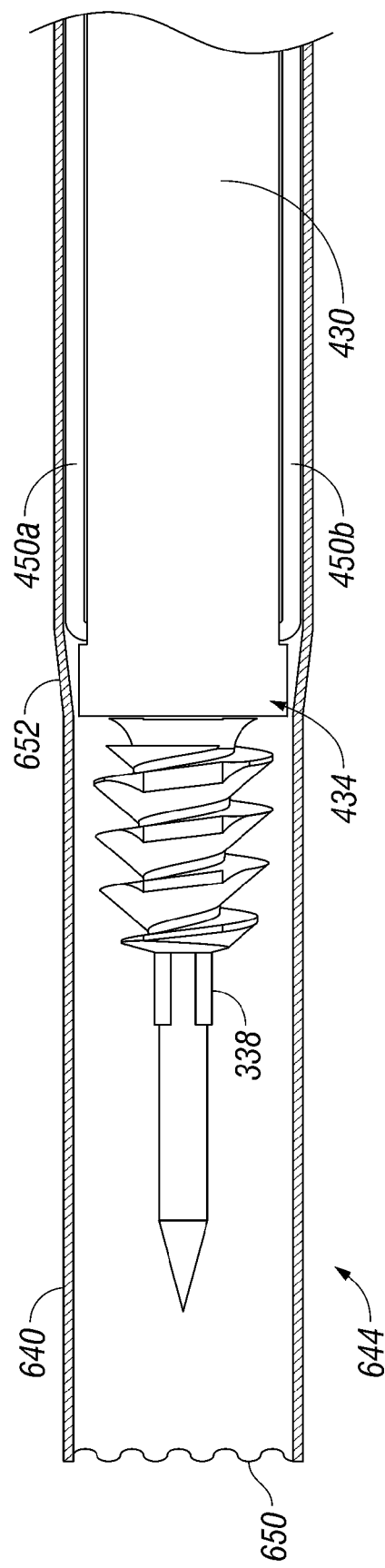
FIG. 65 is a partial cross-sectional view of the distal end of multi-fire surgical instrument of FIGS. 46-64 illustrated prior to disengaging the lockout.

Now referring to FIG. 65, prior to disengaging lockout 620 (see FIG. 55), distal portion 644 of outer tube 640 extends past distal portion 434 of inner tube 430. In this embodiment, a plurality of crenellations 650 is disposed around the periphery of distal portion 644 of outer tube 640. In the embodiment illustrated in FIG. 65, crenellations 650 form a sine-like wave, but other regular and irregular patterns are envisioned and within the scope of the present disclosure. Crenellations 650 facilitate the insertion of a trocar (not shown) and manipulation of mesh "M" (FIG. 66).

With continued reference to FIG. 65, outer tube 640 includes a flared section 652 disposed around its outer periphery and adjacent distal portion 644. Prior to disengaging locket 620, at least a portion of flared section 652 is located distally of bands 450a, 450b.

Figure 66:
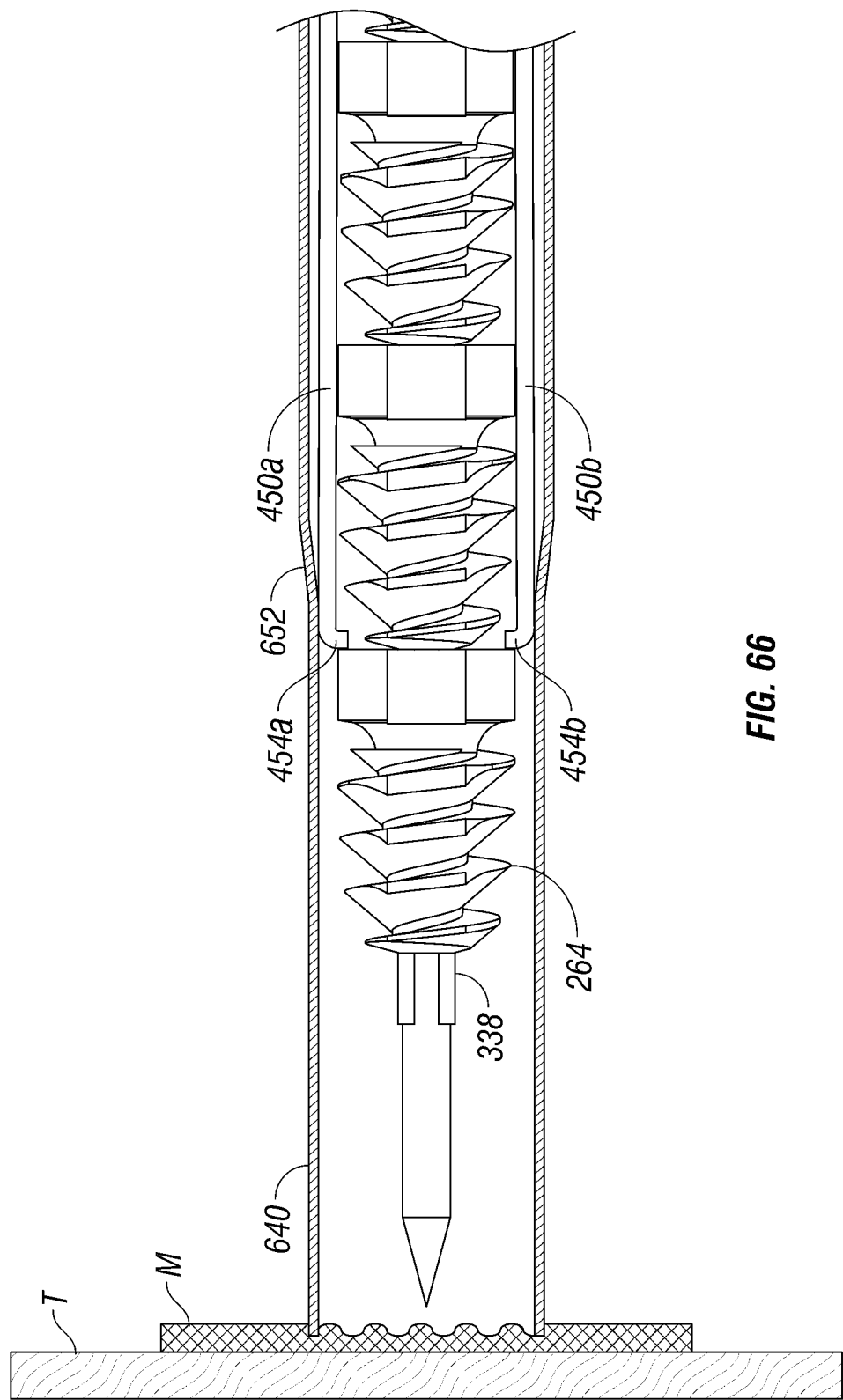
FIG. 66 is a partial cross-sectional view of the distal end of multi-fire surgical instrument of FIGS. 46-65 illustrated with the lockout disengaged.

FIG. 66 illustrates outer tube 640 pushing against mesh "M," which translates outer tube 640 proximally, thus disengaging lockout 620 and enabling distal-most fastener 264 to be ejected from multi-fire surgical instrument 300. In this embodiment, flared section 652 of outer tube 640 forces bands 450a, 450b radially inward, such that distal faces 454a, 454b are abutting distal-most fastener 264. Upon activation of multi-fire surgical instrument 300, as discussed in detail below, distal movement of bands 450a, 450b forces distal-most fastener 264 distally, thus ejecting distal-most fastener 264 from multi-fire surgical instrument 300.

Referring back to FIG. 55, fifth sub-assembly 600 also includes a small bevel gear 660. Small bevel gear 660 mechanically cooperates with proximal portion 472 of socket 470, such that rotation of small bevel gear 660 (discussed in detail below) corresponds to rotation of socket 470, rotation of inner tuber 430 and thus rotation of distal-most fastener 264.

Figure 56:
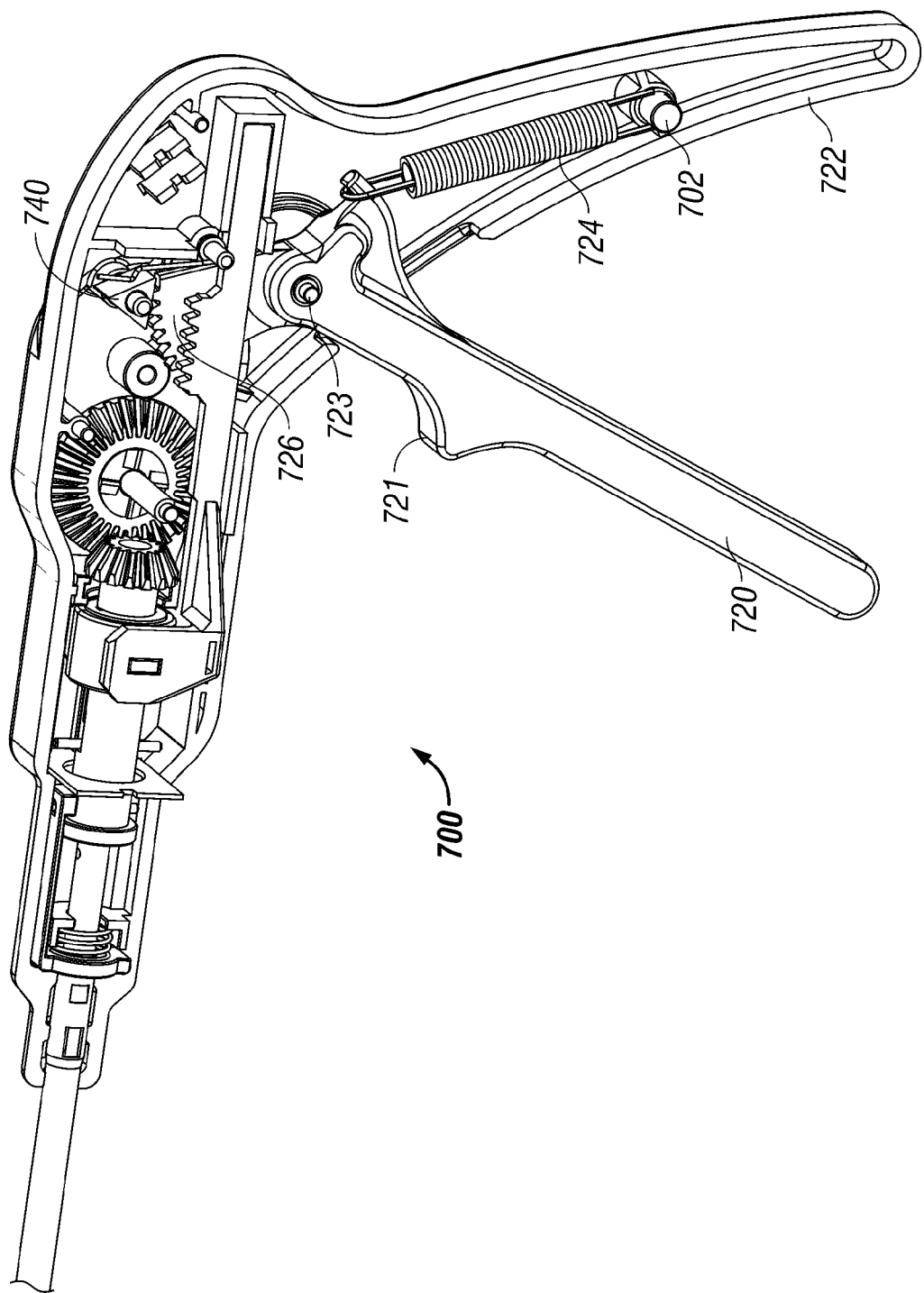
FIG. 56 is a perspective view of the multi-fire surgical instrument of FIG. 55 further including a large bevel gear, a movable handle and a portion of housing.
Figure 57:
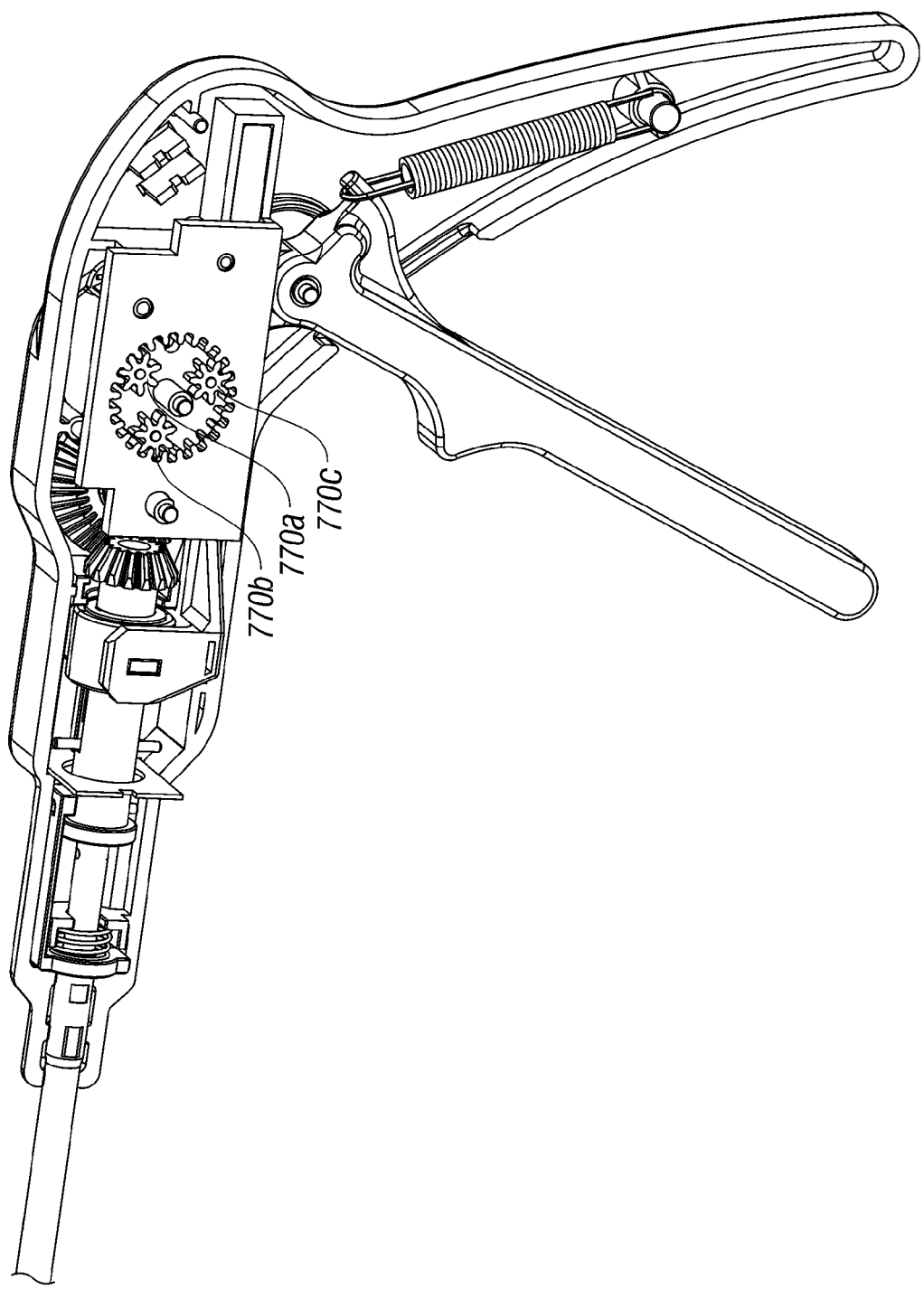
FIG. 57 is a perspective view of the multi-fire surgical instrument of FIG. 56 further including a planetary ring place, planetary gear carrier and planets.

Handle assembly 700 is discussed with reference to FIGS. 46, 56-64, 69-70 and 73. Body portions 710a, 710b (FIG. 46) mechanically attach (via a snap-fit relationship, welding, or the like) to form a generally hollow housing 710, which houses a least a portion of, inter alia, gear train that includes planetary gear 760 (FIG. 60), planets 770a, 770b, 770c (FIG. 60), planetary sun 780 (FIG. 61), spur gear 800 (FIG. 64) and large bevel gear 730 (FIG. 64). Gear train and small bevel gear 660 are collectively referred to as gear assembly. Referring to FIG. 56, movable handle 720 includes a portion which is disposed within housing 710 and a gripping portion 721 which is extends out from housing 710. A trigger pin 723 is disposed through a hole in movable handle 720, thus providing an axis for movable handle 720 to rotate about. Movable handle 720 moves from a non-actuated position (e.g., FIG. 56) to an actuated position (e.g., FIG. 73) closer to fixed handle 722.

As shown in FIG. 56, a trigger spring 724 attaches to a portion of movable handle 720 at one end and to a housing pin 702 at its other end. As can be appreciated, trigger spring 724 biases movable handle 720 in a non-actuated position. Movable handle 720 also includes spur teeth 726, which mechanically engage planetary gear 760 (FIG. 59).

With reference to FIGS. 59-62, planetary gear 760 includes a planetary carrier 762, planets 770a, 770b, 770c, planetary ring plate 774 and planetary sun 780. Planetary carrier 762 generally includes a tooth gear 763, planet pins 764a, 764b, 764c, a ratchet 766 and a bore 768 extending therethrough. Planetary carrier 762 is in rotatable engagement with planetary ring plate 774 via planetary carrier pin 790, which extends through bore 768. Generally, planetary gear 760 is used to allow for a desired gear-ratio, while minimizing the amount of space taken up within housing 710.

Figure 73:
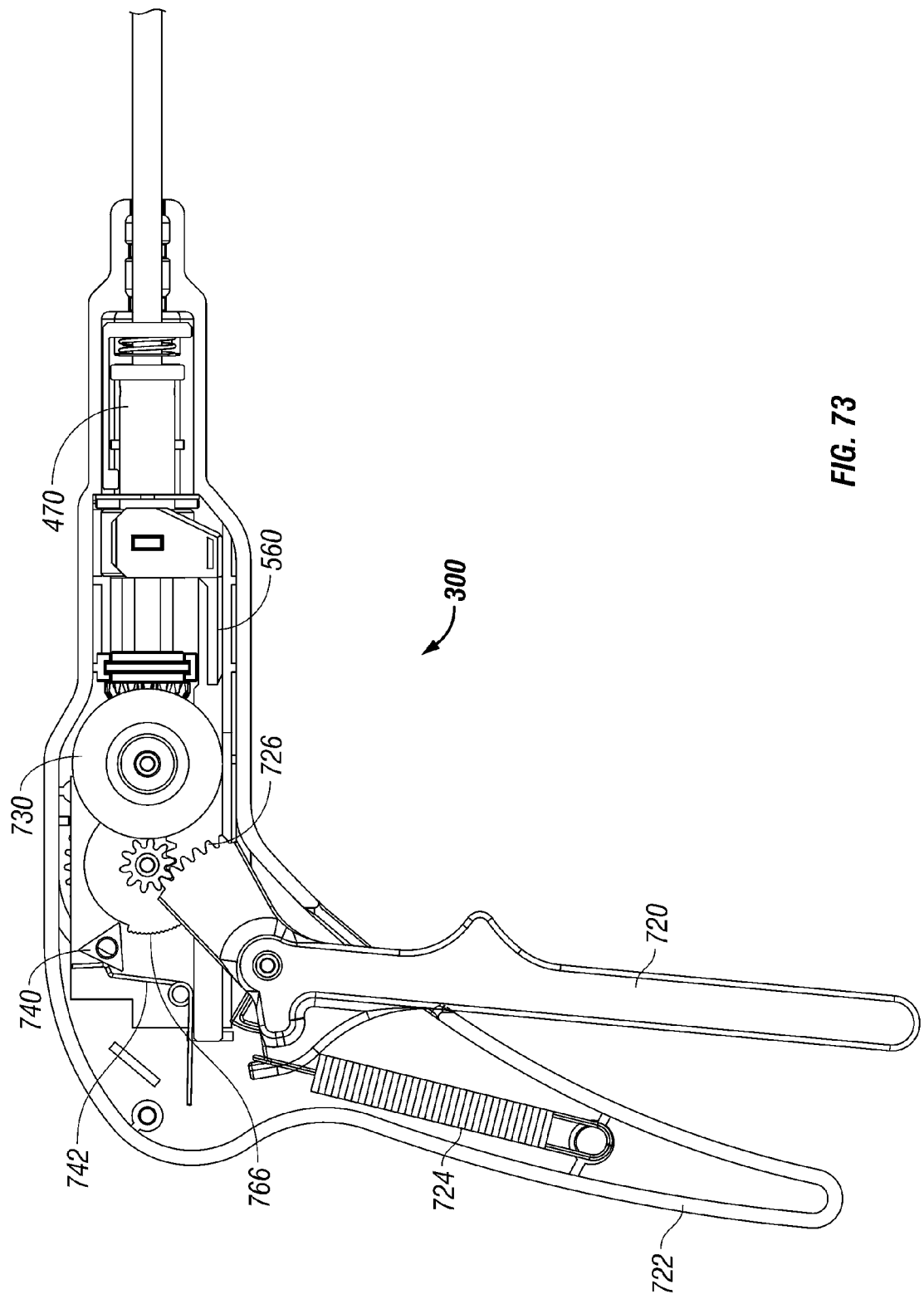
FIG. 73 is a side view of the multi-fire surgical instrument of FIGS. 46-72 illustrated with the movable handle fully squeezed.

Tooth gear 763 is disposed on a first side 761a of planetary carrier 762 and is in mechanical cooperation with spur teeth 726 of movable handle 720 and is also in mechanical cooperation with teeth 568 of rack 560 (FIG. 54). With reference to FIG. 73, the mechanical cooperation between tooth gear 763, spur teeth 726 and rack 560 is illustrated. As can be appreciated, squeezing movable handle 720 proximally (shown fully squeezed in FIG. 73) causes spur teeth 726 to rotate tooth gear 763 in a counter-clockwise direction (with respect to the orientation as illustrated in FIG. 73). Tooth gear 763, in turn, interacts with teeth 568 of rack 560 to translate rack 560 distally. Additionally, the interaction between spur teeth 726 and tooth gear 763 rotates planetary gear carrier 762, as can be appreciated.

Figure 70:
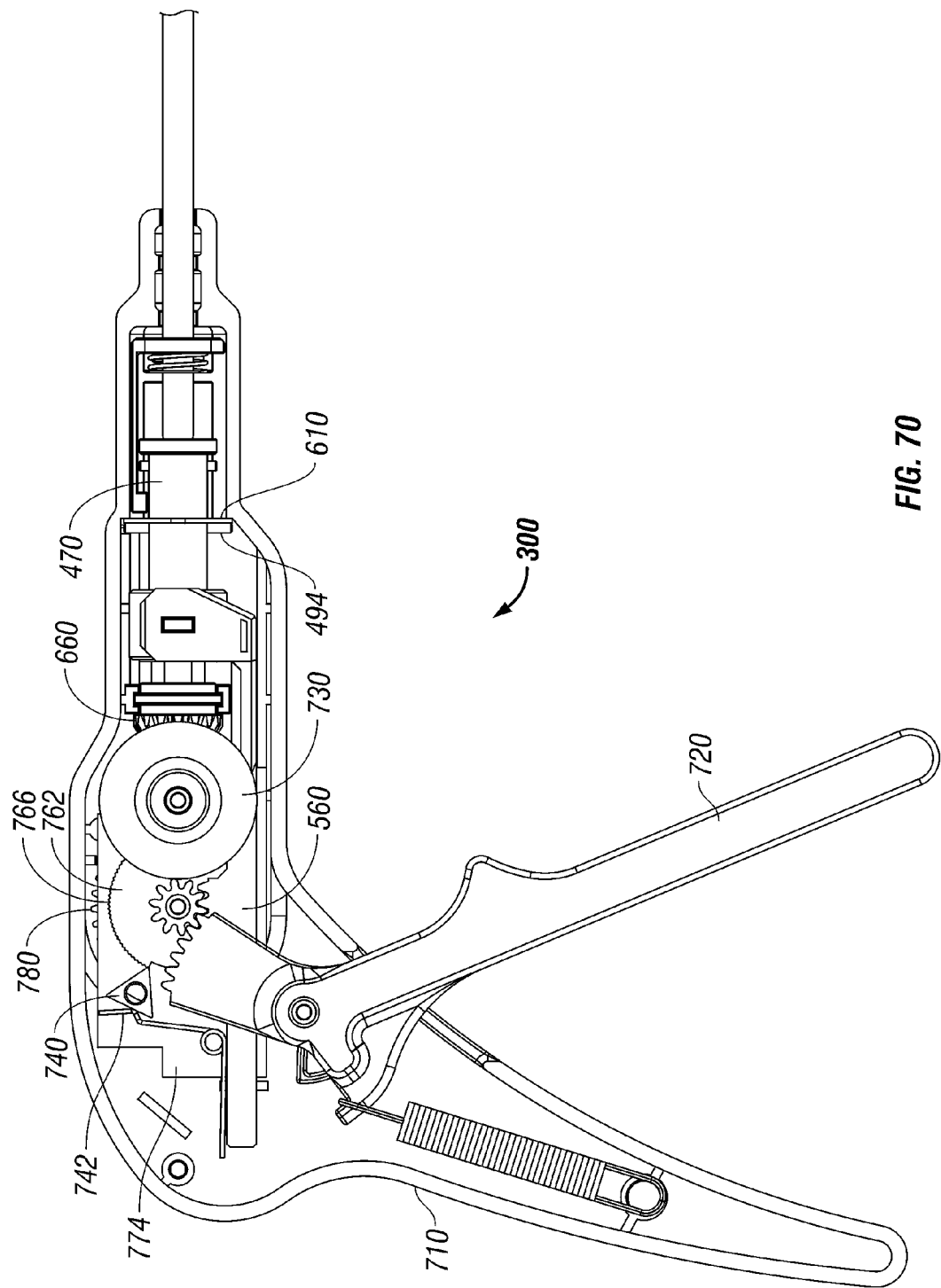
FIG. 70 is a side view of the multi-fire surgical instrument of FIGS. 46-69 illustrated with the lockout disengaged.

Planet pins 764a, 764b, 764c are disposed on a second side 761b of planetary carrier 762, as illustrated in FIGS. 60 and 60a. Planet pins 764a, 764b, 764c extend through bores (not explicitly shown) of planets 770a, 770b, 770c, respectfully, such that planets 760 are rotatable with respect to planetary gear carrier 762. Ratchet 766 is disposed on an edge of planetary gear carrier 762 for interaction with a pawl 740 (FIG. 70). As planetary gear carrier 762 begins to rotate, pawl spring 742 biases pawl 740 such that pawl 740 rides over ratchet 766 of planetary gear carrier 762. Engagement of pawl 740 with ratchet 766 prevents planetary gear carrier 762 and other gears, as discussed below, from reversing before movable handle 720 has been fully squeezed.

Figure 69:
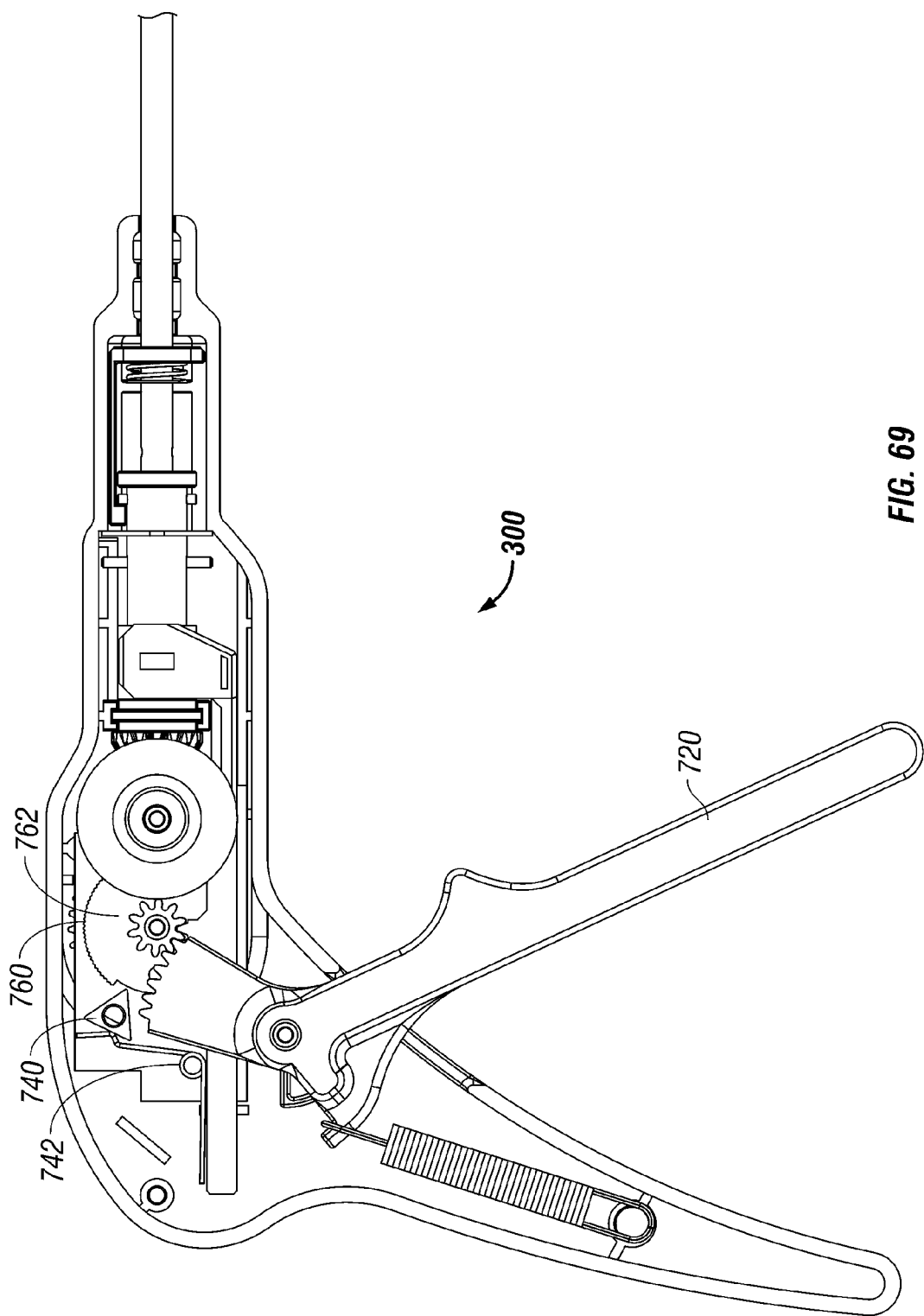
FIG. 69 is a side view of the multi-fire surgical instrument of FIGS. 46-68 illustrated prior to disengaging the lockout.

As illustrated in FIGS. 69, 70 and 73, planetary ring plate 774 mounts to a portion of housing 710, thus resulting in little or no relative movement of planetary ring plate 774 with respect to housing 710. Planetary ring plate 774 includes a first opening 776 (FIG. 60A) therein which allows planetary carrier pin 790 to pass therethrough and which allows planets 770a, 770b, 770c to be housed therein. More specifically, the thickness of planets 770, 770b, 770c may be substantially equal to the thickness of planetary ring plate 774, such that planets 770a, 770b, 770c do not protrude from planetary ring plate 774 when planetary ring plate 774 is abutted against planetary gear carrier 762 (see FIG. 63). Indentations 778 are disposed around the periphery of first opening 776 (FIG. 60a), which mechanically cooperate with teeth of planets 770a, 770b, 770c. Accordingly, rotation of planetary gear carrier 762 causes planets 770a, 770b, 770c to engage indentations 778 of planetary ring plate 774, and thus to rotate.

FIG. 61 illustrates planetary sun 780, which includes first planetary sun gear 782, second planetary sun gear 784 and a bore 786 disposed therethrough. With reference to FIG. 62, planetary carrier pin 790 extends through planetary gear carrier 762 (discussed above), through first opening 776 in planetary ring plate 774 (discussed above) and through bore 786 of planetary sun 780. This interaction between planetary sun 780 and planetary carrier pin 790 allows for rotation of planetary sun 780 with respect to planetary ring plate 774.

First planetary sun gear 782 is dimensioned to fit within first opening 776 of planetary ring plate 774 and to mechanically engage planets 770a, 770b, 770c. Thus, rotation of planets 770a, 770b, 770c, as discussed above, causes planetary sun 780 to rotate. As planetary sun 780 rotates, second planetary sun gear 784 rotates and mechanically engages spur gear 800 (FIG. 64).

As illustrated in FIGS. 63 and 64, spur gear 800 is rotationally disposed on a spur gear pin 802 which is disposed through a second opening 777 in planetary ring plate 774 (FIG. 60A). Spur gear 800 is in mechanical cooperation with second planetary sun gear 784, thus allowing rotational movement of spur gear 800 with respect to planetary ring plate 774.

Also illustrated in FIG. 63 are clutch 750 and a clutch spring 752. Clutch spring 752 is disposed between planetary ring plate 774 and clutch 750. Additionally, clutch spring 752 is configured to engage opening 804 of spur gear 800 (and may be connected thereto) at its first end and to engage clutch 750 at its second end. Alternatively, clutch spring 752 may be free at its first end and may be fastened to clutch 750 at its second end. As seen in FIGS. 63 and 64, clutch 750 is disposed on the opposite side of planetary ring plate 774 as spur gear 800. Clutch 750 includes a plurality of ramps 754 disposed thereon, which mechanically engage second bevel gear ramps 734 disposed on large bevel gear 730, discussed in more detail below.

Clutch spring 752 is designed to urge clutch 750 towards large bevel gear 730. The force exerted by clutch spring 752 is strong enough to cause clutch 750 to rotate large bevel gear 730 when movable handle 720 is depressed. Additionally, the force exerted by clutch spring 752 is weak enough to allow clutch 750 to "ramp over" (i.e., not rotate) second bevel gear ramps 734 when movable handle 720 is released from its depressed orientation. Thus, as is described below, inner tube 430 does not unscrew a fired fastener 10 after movable handle 720 is released or partially released and prior to firing another fastener 10.

With continued reference to FIG. 64, large bevel gear 730 is in mechanical engagement with small bevel gear 660. The axis of rotation A-A of small bevel gear 660 is transverse to the axis of rotation B-B of large bevel gear 730. More specifically, rotation of large bevel gear 730 about axis B-B results in rotation of small bevel gear 660 about axis A-A. This transverse rotation is facilitated by the orientation of the teeth of the gears 660, 730, which combine to form an approximate 90 degree angle. Rotation of small bevel gear 660 results in rotation of distal-most fastener 264.

A brief description of how multi-fire surgical instrument 300 of an embodiment of the present disclosure works is discussed below with reference to FIGS. 46-76. With specific reference to FIGS. 65-68, distal portion 664 of outer tube 640 of multi-fire surgical instrument 300 is placed against mesh M adjacent tissue T. Prior to disengaging lockout 620, movable handle 720 is unable to be depressed. To disengage lockout 620, a surgeon pushes multi-fire surgical instrument 300 against mesh M, thus embedding distal portion 664 into mesh M and disengaging lockout 620. It is contemplated that approximately two pounds of force is necessary for lockout 620 to be disengaged. It is also contemplated that outer tube 640 may be translated proximally a distance of about 0.060 inches to disengage lockout 620.

Once lockout 620 is disengaged, movable handle 720 is fully squeezed to place a single fastener 10 through mesh M and into underlying target tissue T. After movable handle 720 is fully squeezed, the surgeon releases movable handle 720 to allow movable handle 720 to move back to its original position, thus resetting the multi-fire surgical instrument 300. To re-engage lockout 620, the surgeon will relax the pressure of multi-fire surgical instrument 300 against mesh M (i.e., the multi-fir surgical instrument 300 is moved proximally). The surgeon can repeat these steps until the multi-fire surgical instrument 300 contains no more fasteners 10.

A more detailed discussion of how multi-fire surgical instrument 300 works is discussed with reference to FIGS. 65-68. As discussed in detail above, multi-fire surgical instrument 300 is prevented from being fired before lockout 620 is disabled. This ensures that multi-fire surgical instrument 300 cannot be actuated until outer tube 640 is pressed against tissue or mesh. This avoids any inadvertent ejection of fasteners 10 and ensures that the distal portion 644 of outer tube 640 is properly positioned against mesh and/or tissue.

FIG. 65 illustrates multi-fire surgical instrument 300 prior to lockout 620 being disengaged. In this stage, flared portion 652 of outer tube 640 has not forced bands 450a, 450b radially inward. Referring to FIG. 66, to disengage lockout 620, outer tube 640 is pushed against mesh M, thus causing outer tube 640 to move proximally with respect to handle assembly 700. Upon proximal movement of outer tube 640, flared portion 652 of outer tube 640 contacts bands 450a, 450b and urges distal faces 452a, 452b thereof radially inward such that distal faces 452a, 452b are abutting distal-most fastener 264. Accordingly, bands 450a, 450b are now in position to drive distal-most fastener 264 distally. As can be appreciated, prior to disengaging lockout 620, bands 450a, 450b are not in position to drive distal-most fastener 264.

Figure 67:
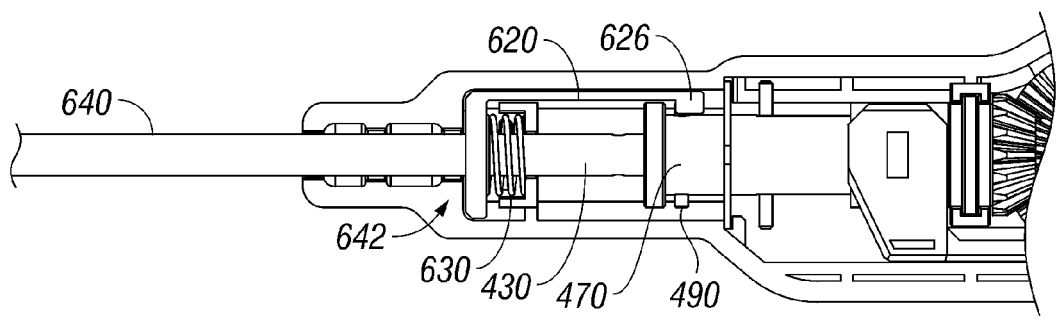
FIG. 67 is a side view of the multi-fire surgical instrument of FIGS. 46-66 illustrated prior to disengaging the lockout.
Figure 68:
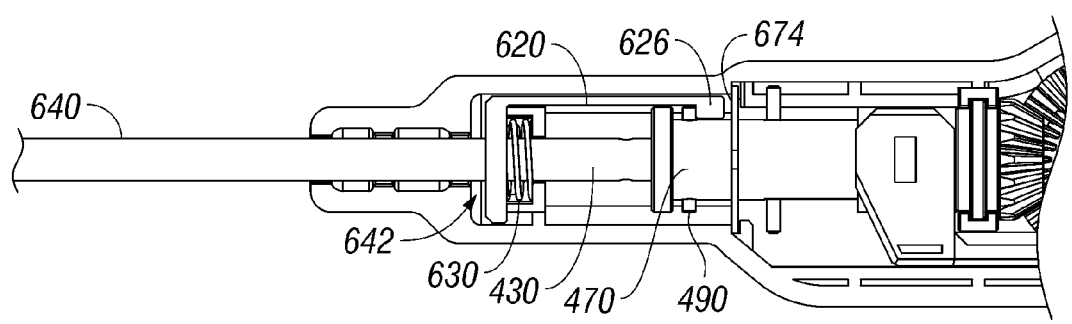
FIG. 68 is a side view the multi-fire surgical instrument of FIGS. 46-67 illustrated with the lockout disengaged.

FIGS. 67 and 68 illustrate proximal portion 642 of outer tube 640 before disengaging lockout 620 and after disengaging lockout 620, respectfully. Referring to FIG. 67, prior to disengaging lockout 620, a slot in a finger 626 of lockout 620 covers torque pin 490, thus restricting rotational movement of torque pin 490 (and thus socket 470 and inner tube 430) with respect to lockout 620. Linear movement socket 470 is also restricted when torque pin 490 is engaged with lockout 620 because as socket 470 is rotated, it is also urged distally (i.e., socket 470 rotates and travels distally at the same time). Thus, prior to disengaging lockout 620, distal-most fastener 264 cannot travel distally and cannot be rotated about axis A-A, as defined above. FIG. 68 illustrates proximal portion 642 of outer tube 640 after lockout 620 has been disengaged (i.e., after outer tube 640 has been pushed against mesh M). In this configuration, lockout spring 630 is at least partially compressed and the slot of lockout 620 has been translated proximally past torque pin 490, thus allowing socket 470 and inner tube 430 to rotate and distally translate. It is envisioned that outer tube 640 and lockout 620 may need to proximally travel about 0.06 inches for lockout 620 to pass over torque pin 490. Additionally, in the illustrated embodiment, second housing rib 674 is disposed on housing 670, which limits proximal movement of lockout 620.

Once the lockout 620 has been disengaged, the multi-fire surgical instrument 300 is ready to fire. The firing process is discussed with reference to FIGS. 69-76. FIG. 69 illustrates multi-fire surgical instrument 300 before movable handle 720 is squeezed. In this orientation, pawl 740 is not in mechanical engagement with ratchet 766 of planetary gear carrier 762.

Figure 71:
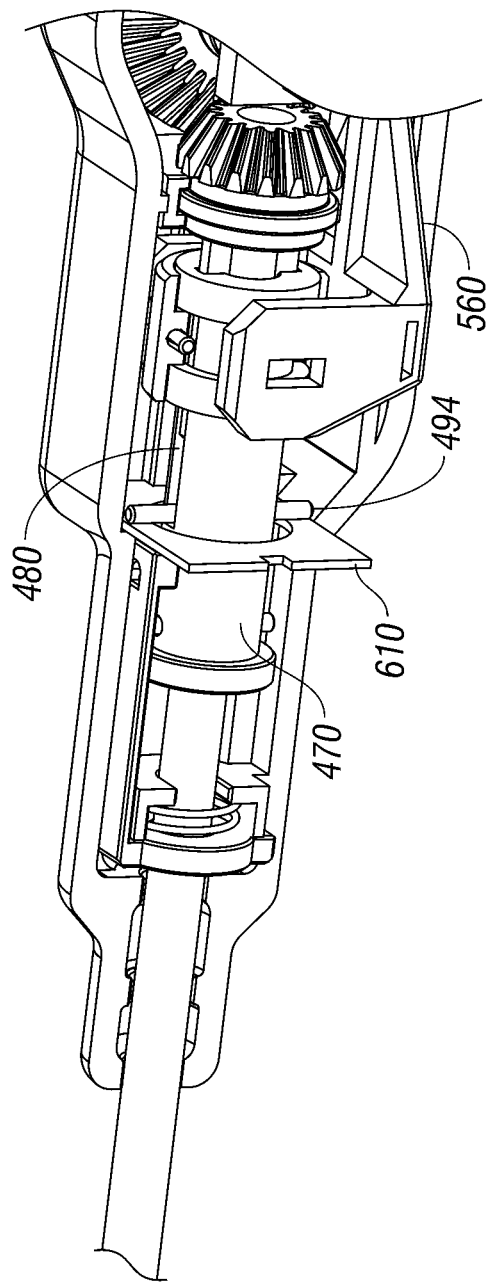
FIG. 71 is a perspective view of the multi-fire surgical instrument of FIGS. 46-70 illustrating the needle pin contacting the needle plate.
Figure 72:
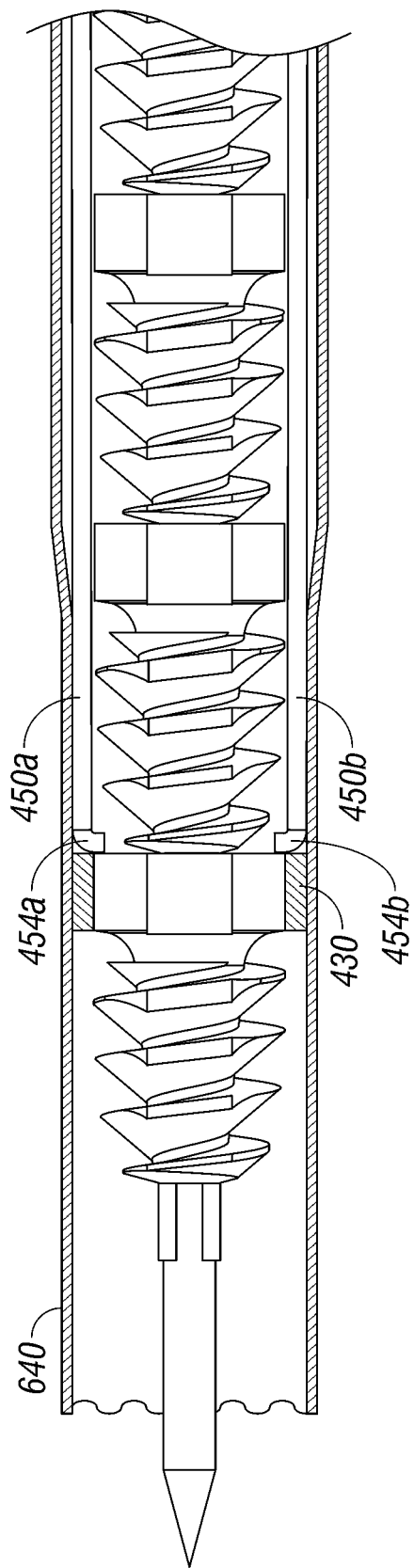
FIG. 72 is a partial cross-sectional view of the distal end of the multi-fire surgical instrument of FIGS. 46-71 illustrating the needle extending beyond the distal end of the outer tube.

FIGS. 70 and 71 illustrate multi-fire surgical instrument 300 while movable handle 720 is being squeezed. At this stage of actuation, pawl 740 is in mechanical engagement with ratchet 766 of planetary gear carrier 762. Actuating movable handle 720 thus causes planetary gear carrier 762 to rotate, which then causes rotation of planets 770a, 770b, 770c (not explicitly shown in these figures), planetary sun 780, spur gear 800 (not explicitly shown in these figures) and large bevel gear 730, collectively referred to as "gear train," hereinafter, as described above. Gear train consequently rotates small bevel gear 660. It is contemplated for the various gear ratios to causes small bevel gear 660 to rotate 11 times each time movable handle 720 is squeezed. Further, it is contemplated that squeezing movable handle 720 approximately 30° causes small bevel gear 660 to rotate 11 times, thus causing distal-most fastener 264 to rotate 11 times. Because small bevel gear 660 is in mechanical cooperation with socket 470, socket 470 is also rotated.

Further, the rotation of planetary gear carrier 762 caused by squeezing of movable handle 720 (as discussed above), causes rack 560 and thus socket 470 to be translated distally. Thus, socket 470 is simultaneously rotated by small bevel gear 660 and driven distally by rack 560. As socket 470 is rotated and driven distally, inner tube 430, which is pinned to socket 470 and coupling 410 via torque pin 490, is also rotated and driven distally (a limited distance as defined by length of slot 420 of coupling 410) towards mesh M. Further, coupling 410 (which is pinned to socket 470 via needle pin 494) and needle 330 (which is coupled to socket 470, see FIG. 47) are also rotated and driven distally (a limited distance as defined by the distance between needle pin 494 and needle plate 610, e.g., approximately 3.5 mm) towards mesh M. That is, when movable handle 720 is squeezed, socket 470, inner tube 430, coupling 410, needle 330 and fasteners 10 (including distal-most fastener 264) are rotated and translated distally until needle pin 494 contacts needle plate 610. Upon such contact between needle pin 494 and needle plate 610, coupling 410, needle 330 and non-lead fasteners 10 cease rotation and distal movement, while socket 470, inner tube 430 and distal-most fastener 264 continue rotating and translating distally. More specifically, this amount of pressure forces distal-most fastener 264 over needle retention feature 338, as discussed above, and into mesh M.

Figure 74:
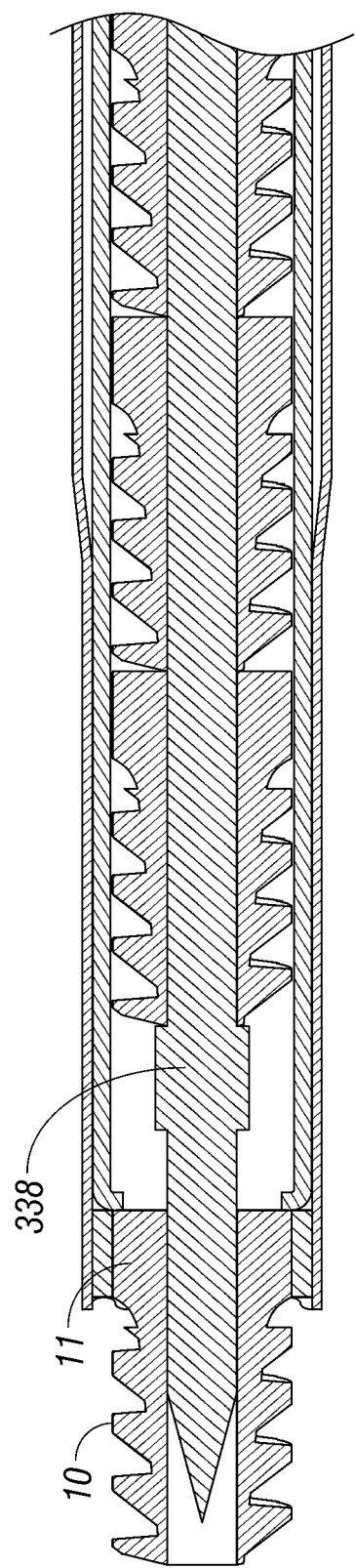
FIG. 74 is a cross-sectional view of the distal end of the multi-fire surgical instrument of FIGS. 46-73 illustrated with the movable handle fully squeezed.

Distal translation of rack 560 and fasteners 10 is described in further detail with reference to FIG. 71. During the actuation of movable handle 720, once rack 560 has traveled a predetermined distance, e.g., about 3.5 mm, needle pin 494 contacts needle plate 610 (as shown). At this point, distal travel of coupling 410 and needle 330 ceases. Upon continued actuation of movable handle 720, slot 480 allows socket 470 to continue distal movement. Therefore, distal-most fastener 264 is able to be forced distally over needle retention feature 338 of stationary needle 330 (FIG. 74). The remaining fasteners 10 remain within inner tube 430 proximally of needle retention feature 338. At this point, as shown in FIG. 73, movable handle 720 is fully squeezed, rack 560 is fully extended and pawl 740 is released from ratchet 766. Additionally, multi-fire surgical instrument 300 is designed and configured so inner tube 430 and head 11 of fasteners 10 do not travel past mesh M when multi-fire surgical instrument 300 is fired. With reference to FIG. 75, after the final fastener 10 is fired, needle retention feature 338 prevents pusher 340 from traveling farther distally.

After the firing stroke is complete, the surgeon releases movable handle 720, thus returning multi-fire surgical instrument 300 to its pre-fired position. Trigger spring 724 returns movable handle 720 to its pre-fired position, thus causing pawl 740 to ride back over ratchet 766 and return to its pre-fired position. Additionally, the return of movable handle 720 to its pre-fired position causes spur teeth 726 to reverse gear train (with the exception of large bevel gear 730) and rack 560 to retract, such that the components are in their pre-fired position. Specifically, as socket 470 is forced proximally by rack 560, inner tube 430 is also forced proximally. As a result, socket 470 moves needle pin 494 proximally, which causes needle 330 to also move proximally. As discussed above, the compression force of clutch spring 752 is weak enough to allow clutch 750 to "ramp over" (i.e., not rotate) ramps 734 of second bevel gear 730 when movable handle 720 is released from its squeezed orientation. Therefore, inner tube 430 does not unscrew fastener 10. Further, to return lockout 620 of multi-fire surgical instrument 300 to its unengaged position, the pressure exerted on outer tube 640 is released (e.g., multi-fire surgical instrument 300 is moved proximally). This release of pressure also returns bands 450 to their starting position and in place to drive the next fastener 10.

Figure 76:
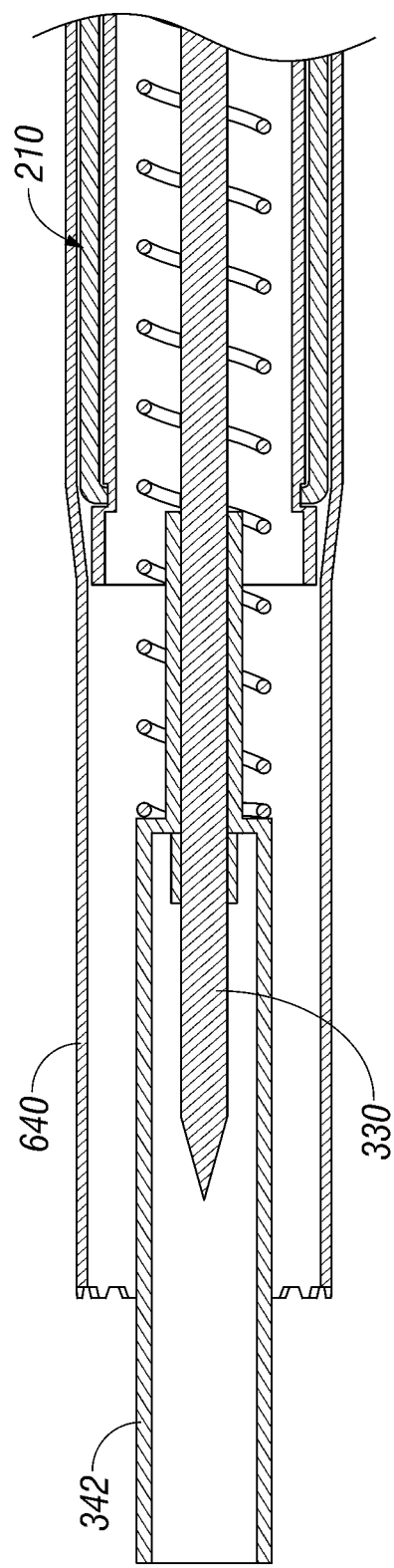
FIG. 76 is a cross-sectional view of the distal end of the multi-fire surgical instrument of FIGS. 46-75 illustrating an elongated pusher, in accordance with an embodiment of the present disclosure.

In an embodiment of the present disclosure illustrated in FIG. 76, multi-fire surgical instrument 300 includes an elongated pusher 342. Elongated pusher 342 is dimensioned and configured to extend distally beyond outer tube 640 (e.g., about 0.2 inches beyond outer tube 640) after the final fastener 10 has been ejected and after the pressure exerted on outer tube 640 has been released. This extension of elongated pusher 342 beyond outer tube 640 is a visual indicator, showing that the last fastener 10 has been ejected and that the elongate tubular member or cartridge subassembly 210 includes no fasteners 10 therein.

It will be understood that various modifications may be made to the embodiments disclosed herein. For example, as noted hereinabove, the disclosed surgical fasteners may include other means for rotation into tissue such as, for example, noncircular holes extending therethrough, alternative structure on the head of the surgical fastener, etc. Further, as indicated above, alternative methods of limiting the linear motion of the outer tubular member, including affixing the outer tubular member to the link and pins sliding in slots in the housing are contemplated. Therefore, the above description should not be construed as limiting, but merely as exemplifications of particular embodiments. Those skilled in the art will envision other modifications within the scope and spirit of the claims appended hereto.

The invention claimed is:

1. A surgical instrument for delivering a fastener, the surgical instrument comprising:
   a housing including:
      an actuation assembly operatively connected to a movable handle; and
      a gear assembly operatively connected to the actuation assembly;
   an elongate tubular member extending distally from the housing and being configured to receive at least one fastener therein, the elongated tubular member including an inner tube, an outer tube and at least one band, the elongate tubular member defining a central longitudinal axis;
   at least one fastener disposed within the elongate tubular member, each fastener defining a central lumen therethrough; and
   an introducer disposed at least partially within the elongate tubular member, the introducer advanceable from the elongate tubular member and configured to extend through the lumen of each fastener,
   wherein advancement of a distal face of the band, into contact with a flared portion of the outer tube, causes at least one fastener to advance distally along the introducer.

2. The surgical instrument of claim 1, wherein the housing further includes a fixed handle, the movable handle pivotably attached to the fixed handle, wherein actuation of the movable handle relative to the fixed handle actuates the actuation assembly to move a distal-most fastener distally along the introducer.

3. The surgical instrument of claim 2, wherein the gear assembly further includes a rack in mechanical cooperation with the movable handle and at least a portion of the actuation assembly for providing a mechanical connection therebetween.

4. The surgical instrument of claim 1, wherein the gear assembly is actuable to rotate the elongate tubular member and a distal-most fastener.

5. The surgical instrument of claim 1, wherein the housing includes a fixed handle, the movable handle pivotably attached to the fixed handle, wherein actuation of the movable handle towards the fixed handle actuates the actuation assembly and the gear assembly to move a distal-most fastener distally and to rotate the distal-most fastener, whereby a complete actuation stroke is defined by moving the movable handle a sufficient distance to eject the distal-most fastener from the elongate tubular member.

6. The surgical instrument of claim 5, wherein the gear assembly includes a planetary gear and a plurality of planets disposed in mechanical engagement therewith, the planetary gear and the plurality of planets enable the distal-most fastener to be rotated a plurality of times in response to a complete actuation stroke.

7. The surgical instrument of claim 6, wherein the planetary gear and the plurality of planets enable the distal-most fastener to be rotated approximately 11 times in response to a complete actuation stroke.

8. The surgical instrument of claim 5, wherein the actuation assembly returns to a pre-actuated position when the movable handle returns to a pre-fired position.

9. The surgical instrument of claim 8, further including a pawl disposed in mechanical cooperation with a portion of the gear assembly and which prevents the movable handle from moving to the pre-fired position until a complete actuation stroke has been performed.

10. The surgical instrument of claim 8, further including a clutch in mechanical engagement with a portion of the gear assembly and which prevents at least a portion of the elongate tubular member from rotating in an opposite direction when the movable handle returns to the pre-fired position.

11. The surgical instrument of claim 1, further including a lockout disposed in mechanical cooperation with the elongate tubular member, the lockout being movable from a first position where the lockout prevents proximal movement of the movable handle to a second position where the lockout allows proximal movement of the movable handle, and whereby applying a predetermined amount of pressure in a proximal direction against the elongate tubular member causes the lockout to move from the first position to the second position.

12. The surgical instrument of claim 1, further including a visual indicator showing that the elongate tubular member includes no fasteners therein.

13. A surgical instrument for delivering a fastener, the surgical instrument comprising:
a housing including:
an actuation assembly;
a gear assembly; and
a handle assembly including a fixed handle and a movable handle, the movable handle being movable between a pre-fired position and an actuated position;
an elongate tubular member extending distally from the housing and including an outer tube and an inner tube, the elongate tubular member being configured to receive at least one fastener therein;
an introducer disposed at least partially within the elongate tubular member, the introducer advanceable from the elongate tubular member and configured to receive at least one fastener thereon;
a lockout disposed in mechanical cooperation with the elongate tubular member, the lockout being movable from a first position where it prevents relative movement between the movable handle and the fixed handle to a second position where it allows relative movement of the movable handle with respect to the fixed handle, and whereby moving the outer tube proximally a predetermined distance causes the lockout to move from the first position thereof to the second position thereof; and
wherein moving the movable handle from the pre-fired position thereof towards the actuated position thereof actuates the actuation assembly which:
forces a distal-most fastener to move distally over the introducer and actuates the gear assembly; and
causes the distal-most fastener to rotate; and
wherein a complete actuation stroke is defined by moving the movable handle a sufficient distance to eject the distal-most fastener from the elongate tubular member.

14. The surgical instrument of claim 13, wherein the elongate tubular member is configured to carry at least one band having a first position for allowing the passage of at least one fastener and at least a second position for engaging a distal-most fastener, and wherein actuation of the actuation assembly forces a distal face of the at least one band towards the distal-most fastener thus forcing the distal-most fastener to move distally over the introducer.

15. The surgical instrument of claim 13, wherein the gear assembly includes a planetary gear and a plurality of planets disposed in mechanical engagement therewith, the planetary gear and the plurality of planets enable the distal-most fastener to be rotated a plurality of times in response to a complete actuation stroke.

16. The surgical instrument of claim 13, further including a pawl disposed in mechanical cooperation with a portion of the gear assembly and which prevents the movable handle from moving to the pre-fired position thereof until a complete actuation stroke has been performed.

17. The surgical instrument of claim 13, further including a clutch in mechanical engagement with a portion of the gear assembly, the clutch preventing the elongate tubular member from rotating in an opposite direction when the movable handle returns to the pre-fired position thereof.

18. The surgical instrument of claim 13, wherein the movable handle is biased in the pre-fired position thereof.

19. The surgical instrument of claim 13, wherein the gear assembly includes a first bevel gear disposed on a first axis and a second bevel gear disposed on a second axis, the first axis being transverse to the second axis.

20. The surgical instrument of claim 13, further including a visual indicator showing that the elongate tubular member includes no fasteners therein.

* * * * *